United States Patent
Silva et al.

(10) Patent No.: US 10,835,513 B2
(45) Date of Patent: Nov. 17, 2020

(54) METHODS AND TREATMENTS FOR THE LEARNING AND MEMORY DEFICITS ASSOCIATED WITH NOONAN SYNDROME

(71) Applicant: The Regents of the University of California, Oakland, CA (US)

(72) Inventors: Alcino Silva, Sherman Oaks, CA (US); Yong-Seok Lee, Los Angeles, CA (US); Dan Ehninger, Bonn (DE)

(73) Assignee: The Regents of the University of California, Oakland, CA (US)

( * ) Notice: Subject to any disclaimer, the term of this patent is extended or adjusted under 35 U.S.C. 154(b) by 519 days.

(21) Appl. No.: 14/900,907

(22) PCT Filed: Jun. 27, 2014

(86) PCT No.: PCT/US2014/044709
§ 371 (c)(1),
(2) Date: Dec. 22, 2015

(87) PCT Pub. No.: WO2014/210538
PCT Pub. Date: Dec. 31, 2014

(65) Prior Publication Data
US 2016/0158194 A1    Jun. 9, 2016

Related U.S. Application Data

(60) Provisional application No. 61/840,643, filed on Jun. 28, 2013.

(51) Int. Cl.
| | |
|---|---|
| *A61P 25/28* | (2006.01) |
| *A61K 31/22* | (2006.01) |
| *A61K 45/06* | (2006.01) |
| *A61K 31/366* | (2006.01) |
| *A61K 31/4418* | (2006.01) |
| *A61K 31/277* | (2006.01) |
| *A61K 31/505* | (2006.01) |
| *A61K 31/40* | (2006.01) |
| *A61K 31/404* | (2006.01) |

(52) U.S. Cl.
CPC ............ *A61K 31/366* (2013.01); *A61K 31/22* (2013.01); *A61K 31/277* (2013.01); *A61K 31/40* (2013.01); *A61K 31/404* (2013.01); *A61K 31/4418* (2013.01); *A61K 31/505* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 8,222,293 B2* | 7/2012 | Silva | A61K 31/366 |
| | | | 514/307 |
| 2003/0176651 A1 | 9/2003 | Grant et al. | |
| 2007/0299096 A1 | 12/2007 | Silva et al. | |
| 2010/0120720 A1 | 5/2010 | Levy et al. | |
| 2011/0184056 A1 | 7/2011 | Munoz et al. | |

FOREIGN PATENT DOCUMENTS

| | | | | |
|---|---|---|---|---|
| WO | 2012019113 A2 | 2/2012 | | |
| WO | WO 2012019113 A2 * | 2/2012 | ........... | A61K 31/353 |
| WO | 2012054724 A1 | 4/2012 | | |
| WO | WO 2012054724 A1 * | 4/2012 | ........... | A61K 31/366 |
| WO | 2012117334 A1 | 9/2012 | | |

OTHER PUBLICATIONS

Nyström et al., Noonan syndrome and neurofibromatosis type I in a family with a novel mutation in NF1, Clin Genet. Dec. 2009;76(6):524-34. doi: 10.1111/j.1399-0004.2009.01233.x. Epub Oct. 21, 2009, printed from https://www.ncbi.nlm.nih.gov/pubmed/19845691, abstract only, 2 pages.*
Wu et al, MEK-ERK pathway modulation ameliorates disease phenotypes in a mouse model of Noonan syndrome associated with the Raf1(L613V) mutation, J Clin Invest. Mar. 2011;121(3):1009-25. doi: 10.1172/JCI44929. Epub Feb. 21, 2011, printed from https://www.ncbi.nlm.nih.gov/pubmed/21339642, Abstract only, 2 pages.*
Epilepsy Action Australia, Memory, printed from https://www.epilepsy.org.au/about-epilepsy/living-with-epilepsy/lifestyle-issues/memory/ on Dec. 20, 2017, 6 pages.*
International Search Report and Written Opinion received in PCT/US2014/044709, dated Oct. 10, 2014.
Romano et al., "Noonan Syndrome: Clinical Features, Diagnosis, and Management Guidelines", Sep. 27, 2010, pp. 746-759, vol. 126, No. 4, Publisher: Pediatrics.
Tartaglia, et al., "Noonan Syndrome: Clinical Aspects and Molecular Pathogenesis", Jan. 15, 2010, pp. 2-26, vol. 1, Publisher: Mol Syndromol.
Verhoeven, et al., "Noonan Syndrome: Psychological and Psychiatric Aspects", 2008, pp. 191-196, vol. 146A, Publisher: American Journal of Medical Genetics Part A.
Wingbermuhle, et al., "Neuropsychological and Behavioral Aspects of Noonan Syndrome", Dec. 22, 2009, pp. 15-23, vol. 72, No. suppl 2, Publisher: Horm Res.

* cited by examiner

*Primary Examiner* — Gigi G Huang
(74) *Attorney, Agent, or Firm* — Suzannah K. Sundby, Esq.; Canady + Lortz LLP

(57) ABSTRACT

Disclosed herein are methods and compositions for treating learning and memory deficits associated with Noonan Syndrome.

15 Claims, 29 Drawing Sheets a b

METHODS AND TREATMENTS FOR THE LEARNING AND MEMORY DEFICITS ASSOCIATED WITH NOONAN SYNDROME

CROSS-REFERENCE TO RELATED APPLICATIONS

This application claims the benefit of U.S. Patent Application Ser. No. 61/840,643, filed 28 Jun. 2013, which is herein incorporated by reference in its entirety.

ACKNOWLEDGEMENT OF GOVERNMENT SUPPORT

This invention was made with Government support under AG013622 and NS038480, awarded by the National Institutes of Health, and DAMD17-02-1-0637, awarded by the U.S. Army Medical Research and Materiel Command. The Government has certain rights in the invention.

BACKGROUND OF THE INVENTION

1. Field of the Invention

The present invention generally relates to methods and compositions for treating learning and cognitive deficits associated with Noonan Syndrome.

2. Description of the Related Art

Noonan syndrome (NS) is an autosomal dominant genetic disorder with an incidence of about 1 in 2,500 live births characterized by facial abnormalities, short stature, motor delay, and cardiac defects[1, 2]. Importantly, 30% to 50% of NS patients show cognitive deficits[3-6]. NS patients also show clumsiness, motor delay, hearing loss, problems in spatial knowledge, planning, and social/emotional problems[3, 4, 7]. Recent studies showed that NS patients show a deficit in hippocampus-dependent memory task[4, 8, 9].

Germline mutations in genes involved in Ras-Erk signaling such as PTPN11, SOS1, KRAS, NRAS, RAF1, BRAF, SHOC2, MEK1, and CBL have been also reported to cause NS[1, 10]. Among those, the mutations in the PTPN11 gene which encodes the non-receptor protein tyrosine phosphatase SHP2 account for ~50% of NS cases[1]. SHP2 is a positive regulator for Ras-Erk signaling[11] which is critically involved in many cellular processes including learning and memory[12]. The PTPN11 mutations found in NS patients result in gain-of-function alleles that up-regulate this signaling cascade[11, 13-15]. Cognitive problems such as learning disabilities and memory impairments are common in NS[3, 5, 6]. However, little is known about the role of PTPN11 in synaptic plasticity and learning and memory in the mammalian brain. Furthermore, there is no available treatment for cognitive deficits associated with this common genetic disorder.

SUMMARY OF THE INVENTION

In some embodiments, the present invention is directed to a method of treating a subject with a cognitive deficit, which comprises administering an effective amount of one or more hydroxymethylglutaryl CoA (HMG CoA) reductase inhibitors to a subject afflicted with a cognitive disorder associated with Noonan Syndrome. In some embodiments, the one or more HMG CoA inhibitors comprises a statin. In some embodiments, the statin is selected from the group consisting of atorvastatin, cerivastatin, fluvastatin, lovastatin, pravastatin, pitavastatin, rovustatin, simvastatin, and mixtures thereof. In some embodiments, the effective amount does not significantly lower total serum cholesterol level in the subject. In some embodiments, the method further comprises administering a farnesyl transferase inhibitor to the subject. In some embodiments, the method further comprises administering a geranylgeranyl transferase inhibitor to the subject. In some embodiments, the method further comprises administering an inhibitor of γ-aminobutyric acid (GABA) mediated inhibition to the subject. In some embodiments, the inhibitor comprises an inhibitor of GABA receptor activity. In some embodiments, the inhibitor of GABA receptor activity is selective for $GABA_A$. In some embodiments, the inhibitor of GABA receptor activity is selective for $GABA_B$. In some embodiments, the administering is by adjunctive administration. In some embodiments, the adjunctive administration is simultaneous administration. In some embodiments, the adjunctive administration is sequential administration. In some embodiments, the subject has a normal cholesterol level. In some embodiments, the subject is a human. In some embodiments, the subject has been diagnosed as having Noonan Syndrome.

In some embodiments, the present invention is directed to treating a subject with a cognitive deficit which comprises administering an effective amount of an inhibitor of a mitogen-activated protein kinase kinase enzyme (MEK), such as MEK1 or MEK2 to a subject afflicted with a cognitive disorder associated with Noonan Syndrome. In some embodiments, the present invention provides a method of treating cognitive deficits in hippocampal long-term potentiation (LTP) in a subject which comprises administering to the subject an effective amount of an inhibitor of MEK. In some embodiments, the present invention provides a method of treating Ras-ERK over-activation and/or reducing Ras-ERK activation and/or deregulation of Ras-ERK signaling in a subject in need thereof which comprises administering to the subject an effective amount of an inhibitor of MEK. In some embodiments, the present invention provides a method of reversing the AMPA:NMDA current ratio or the mEPSC frequency in a subject having a cognitive disorder associated with Noonan Syndrome which comprises administering to the subject an effective amount of an inhibitor of MEK. In some embodiments, the MEK inhibitor is Trametinib (GSK1120212), Selumetinib, Binimetinib or MEK162, PD-325901, Cobimetinib or XL518, CI-1040, PD035901, or SL237. In some embodiments, the subject is diagnosed as having Noonan Syndrome. In some embodiments, the methods further comprise administering to the subject a hydroxymethylglutaryl CoA (HMG CoA) reductase inhibitor before, during, and/or after administration of the inhibitor of MEK.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein.

littermates (n=11) selectively searched in the target quadrant in a probe trial given after 3 days of training (Ptpn11$^{N308D/+}$, F(3, 32)=13.83, *P<0.0001; WT, F(3, 40)=48.48, *P<0.0001; one-way ANOVA). However, Ptpn11$^{N308D/+}$ mice spent significantly less time in the target quadrant than WT mice (Ptpn11$^{N308D/+}$, 41.85±4.30%; WT, 57.87±4.83%, *P<0.05; t-test). Two-way ANOVA for quadrant occupancy with genotype as between-subjects factor and pool quadrant as within-subjects factor, genotype×pool quadrant interaction: F(3,54)=4.091, *P<0.05. Pool quadrants; target (T), adjacent right (AR), opposite (O), and adjacent left (AL) quadrant. Panel b) Searches of Ptpn11$^{N308D/+}$ mice were significantly further from the target platform than WT mice (WT, 32.53±2.26; Ptpn11$^{N308D/+}$, 40.18±2.05, *P<0.05; t-test). Panel c) Quadrant occupancy for the probe trial conducted after 3 days of training reveals that Ptpn11$^{D61G/+}$ mice (n=10) did not show preference for the target quadrant, but their WT littermates (n=15) did (F(3,36)=2.029, P=0.127 and F(3,56)=23.51, *P<0.0001 for Ptpn11$^{D61G/+}$ and WT, respectively; one-way ANOVA). In addition, Ptpn11$^{D61G/+}$ mice spent significantly less time in the target quadrant than did WT mice (Ptpn11$^{D61G/+}$, 27.44±2.04%; WT, 37.14±2.09, P<0.01; t-test). Two-way ANOVA for quadrant occupancy with genotype as between-subjects factor and pool quadrant as within-subjects factor, genotype×pool quadrant interaction: F(3, 69)=2.884, *P<0.05. n.s., not significant (P>0.05). Panel d) Ptpn11$^{D61G/+}$ showed significantly longer proximity to the target platform than WT mice in a probe trial given after 3 days training (Ptpn11$^{D61G/+}$, 52.43±2.14 cm; WT, 46.23±1.29 cm, *P<0.05; t-test). Data represent mean±s.e.m.

Figure 2:
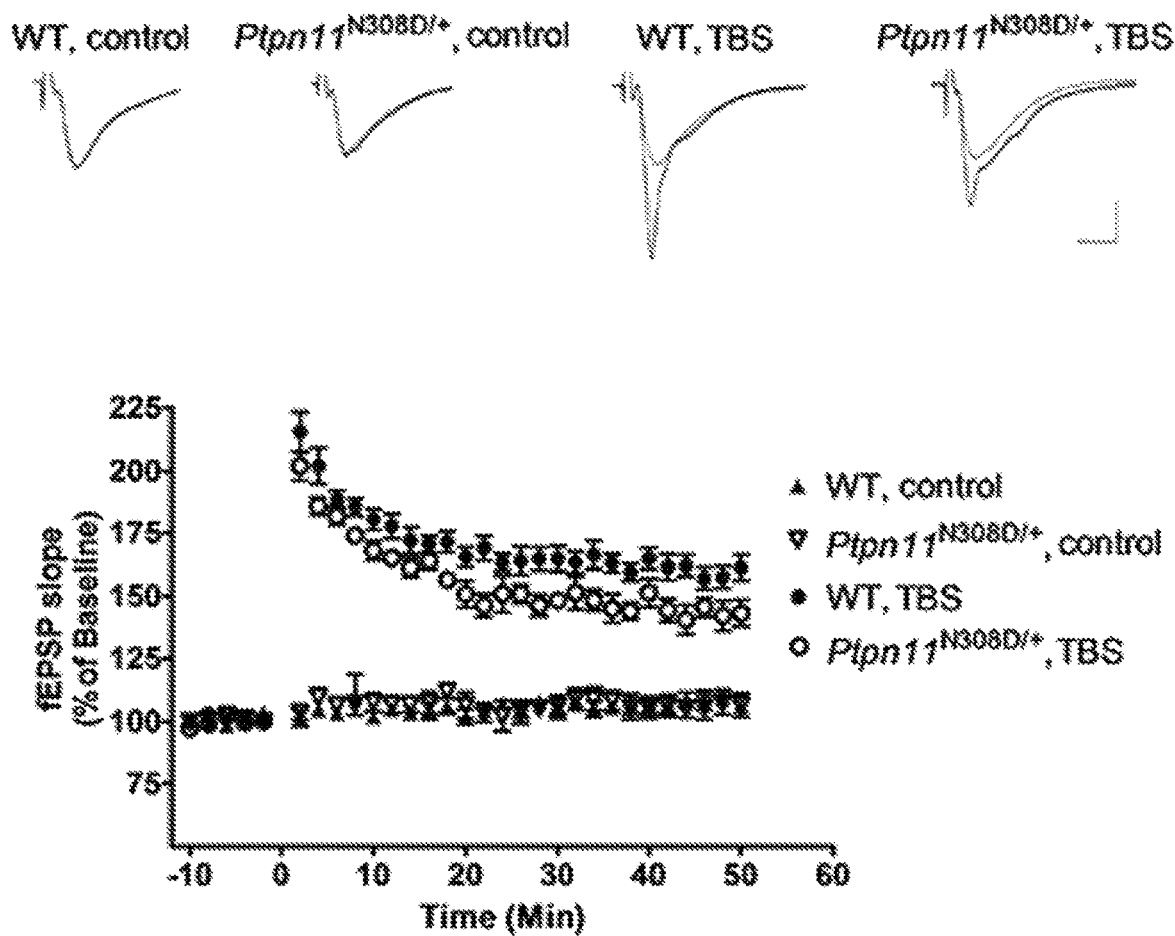
Figure 2:
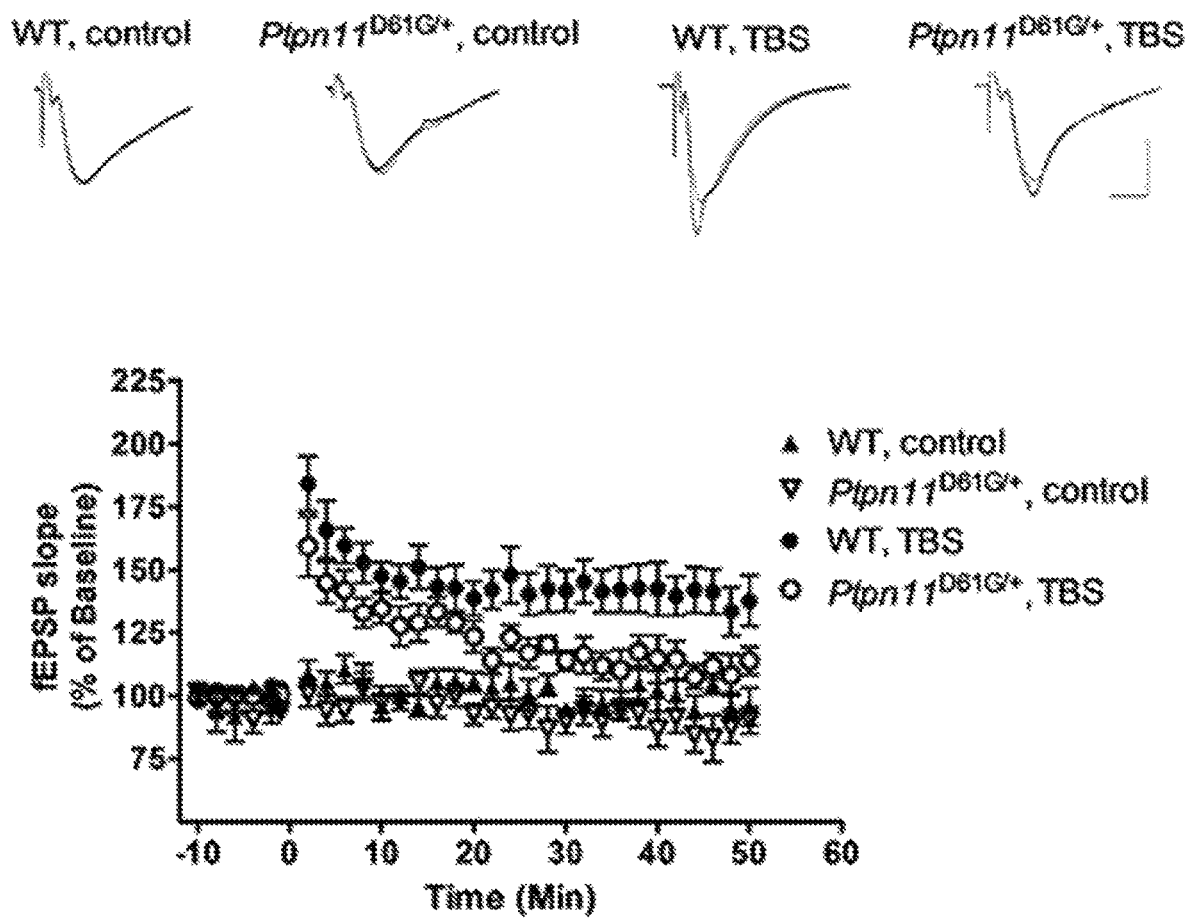

FIG. 2 provides graphs showing that NS mice exhibit hippocampal long-term potentiation (LTP) deficits. Panel a) LTP induced by a 5 TBS (each burst consists of four stimuli at 100 Hz, 200 ms inter-burst interval) was reduced significantly in hippocampal slices from Ptpn11$^{N308D/+}$ mice compared with their WT littermates (WT, n=6 slices from 6 mice; Ptpn11$^{N308D/+}$, n=6 slices from 6 mice; Repeated-measures ANOVA: F(1, 10)=7.893, P<0.05; last 10 min of recording, WT, 159.5±4.23%, Ptpn11$^{N308D/+}$, 143.4±4.81%, t-test, P<0.05). Panel b) LTP induced by a 5 TBS protocol was reduced in hippocampal slices from Ptpn11$^{D61G/+}$ mice compared with those from WT mice (WT, n=7 slices from 7 mice; Ptpn11$^{D61G/+}$ n=7 slices from 6 mice; Repeated-measures ANOVA: F(1,12)=5.828, P<0.05. Last 10 min of recording, WT, 139.2±8.41%, Ptpn11$^{D61G/+}$, 110.8±6.30%, t-test, P<0.05). The LTP deficit in Ptpn11$^{D61G/+}$ mice is more severe than the deficit in Ptpn11$^{N308D/+}$ mice (ANOVA, F(1, 22)=16.95, P<0.001). fEPSP slopes normalized to the average baseline response before LTP induction (at time 0) are plotted in 2-min blocks. Sample traces show responses during baseline (gray) and the last 10 min (black) of the recording (average of ten recording traces). Scale: vertical bar, 0.5 mV; horizontal bar, 4 ms. Error bars represent s.e.m.

Figure 3:
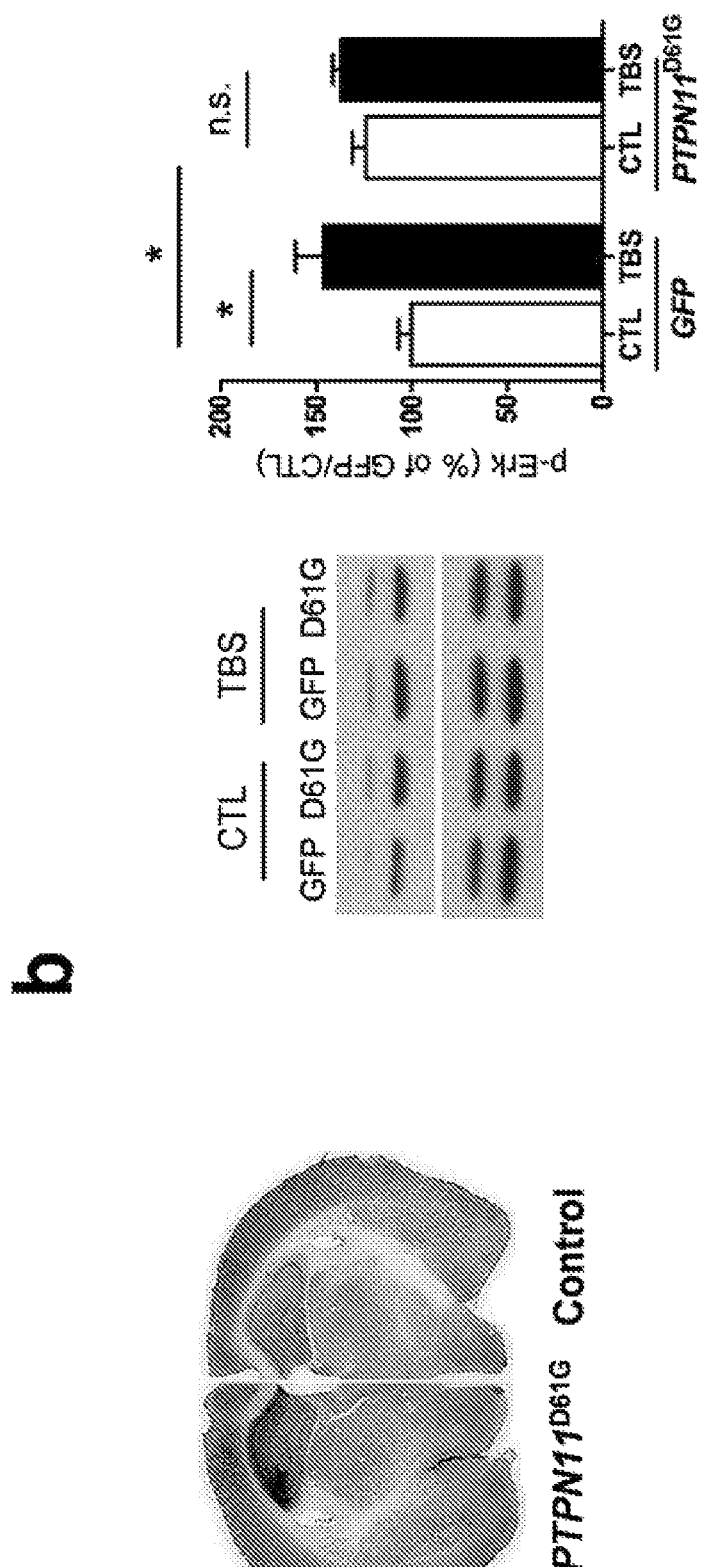
Figure 3:
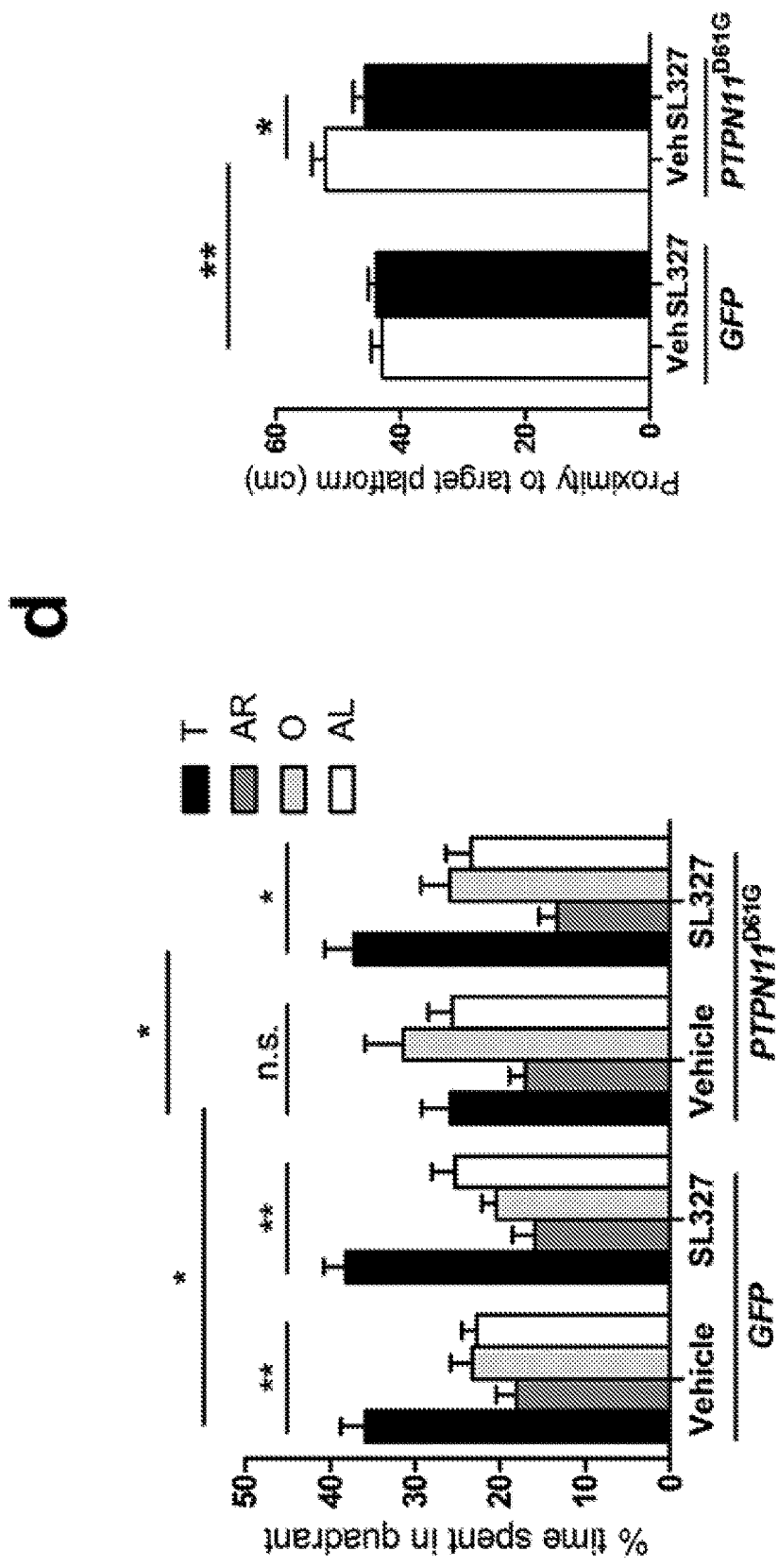
Figure 3:
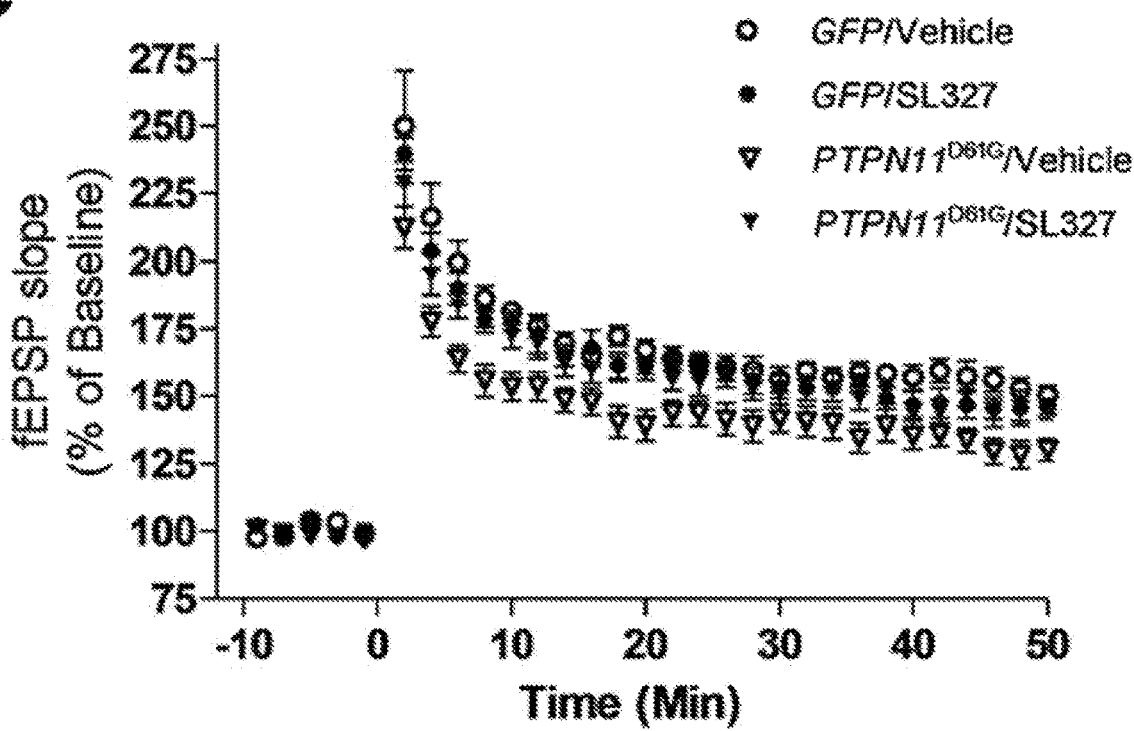
Figure 3:
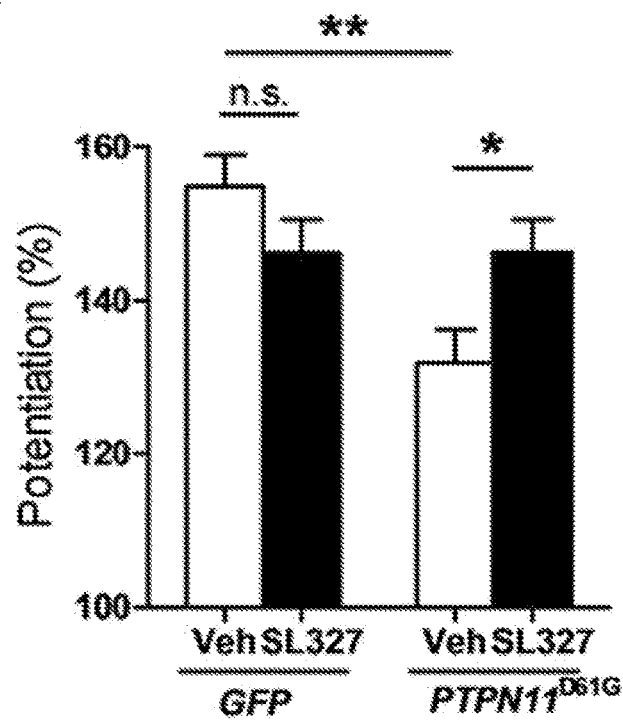

FIG. 3 are graphs showing that PTPN11$^{D61G}$ overexpression induces learning and memory and LTP deficits that can be reversed by MEK inhibition. Panel a) AAV5-PTPN11$^{D61G}$ infection results in overexpression of SHP2$^{D61G}$. Anti-SHP2 immunohistochemistry shows robust overexpression of SHP2 in the hippocampus of AAV5-PTPN11$^{D61G}$-infused brain (left) compared with AAV-GFP infused brain (right). Panel b) PTPN11$^{D61G}$ overexpression increases basal Erk activity (phospho-Erk level) and prevents further Eric activation in response to TBS. Left, Representative immunoblot showing p-Erk (upper) and total Eric (lower) in PTPN11$^{D61G}$-expressing slices and GFP-expressing slices. Slices were prepared 1 hr after TBS. Right, Bar graph displays normalized p-Erk levels (mean±s.e.m.). n=5 for each group. t-test, *P<0.05. Panels c and d) MEK inhibitor SL327 (CAS 305350-87-2) reverses spatial memory deficits in PTPN11$^{D61G}$-overexpressing mice. Panel c) Quadrant occupancy analysis for the probe trail reveals that PTPN11$^{D61G}$/veh mice showed no preference for the target quadrant (TQ vs. other quadrants, Dunnett's Multiple Comparison Test after one-way ANOVA, P>0.05). PTPN11$^{D61G}$/veh mice also spent significantly less time in the target quadrant compared with GFP/veh mice (PTPN11$^{D61G}$/veh, 25.89±3.38%, n=10; GFP/veh, 35.88±2.95%, n=13; t-test, P<0.05). PTPN11$^{D61G}$/SL327 groups selectively searched in the target quadrant (one-way ANOVA, F(3, 36)=10.44, P<0.001; TQ vs. other quadrants, Dunnett's Multiple Comparison Test, *P<0.05). SL327 treatment significantly increased the time spent in the target quadrant in PTPN11$^{D61G}$-expressing mice compared with vehicle-treated PTPN11$^{D61G}$ mice (PTPN11$^{D61G}$/SL327, 37.25±3.50%, n=10, t-test, P<0.05). Panel d) Proximity analysis reveals that the spatial memory deficit in PTPN11$^{D61G}$ group can be reversed by SL327 treatment (GFP/veh, 42.95±1.75 cm, n=13; GFP/SL327, 43.75±1.45 cm, n=8; PTPN11$^{D61G}$/veh, 52.12±2.12 cm, n=10; PTPN11$^{D61G}$/SL327, 45.52±2.14 cm, n=10; Two-way ANOVA, with viral treatment as between subjects factor, F(1, 37)=7.800, **P<0.01. Bonferroni post-tests reveal that SL327 only affects the PTPN11$^{D61G}$ groups, *P<0.05). Panels e and f) MEK inhibitor SL327 reverses LTP deficits caused by PTPN11$^{D61G}$ overexpression. Panel e) PTPN11$^{D61G}$ overexpression significantly impaired 5 TBS-induced LTP, and bath application of SL327 reversed the deficit (Repeated-measures ANOVA, F(3, 72)=140.2, P<0.0001). SL327 (1 μM) was applied for 1 hr before LTP induction, and then maintained in the bath throughout recording. Panel f) Average % fEPSP changes (last 10 minutes of recording) shows a significant LTP deficit in vehicle-treated PTPN11$^{D61G}$ group compared with vehicle-treated GFP group (GFP/veh, 154.8±4.18%, n=7; PTPN11$^{D61G}$/veh, 131.9±4.38, n=10; t-test, **P<0.01) and significant reversal by SL327 treatment (PTPN11$^{D61G}$/SL327, 146.1±4.36%, n=10; t-test, *P<0.05). SL327 did not affect LTP in GFP group (GFP/SL327, 146.2±4.37%, n=7; t-test, P=0.183). Two-way ANOVA with viral treatment as between-subjects factor, F(1, 30)=6.526, *P<0.05. Bonferroni post-test reveals significant effect of SL327 treatment only on the PTPN11$^{D61G}$ group (*P<0.05).

Figure 4:
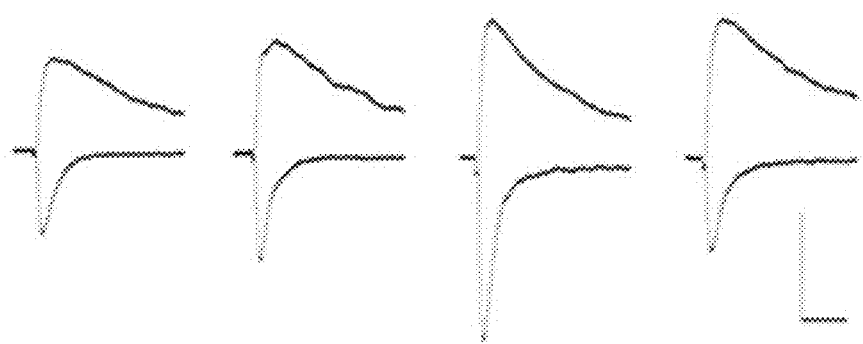
Figure 4:
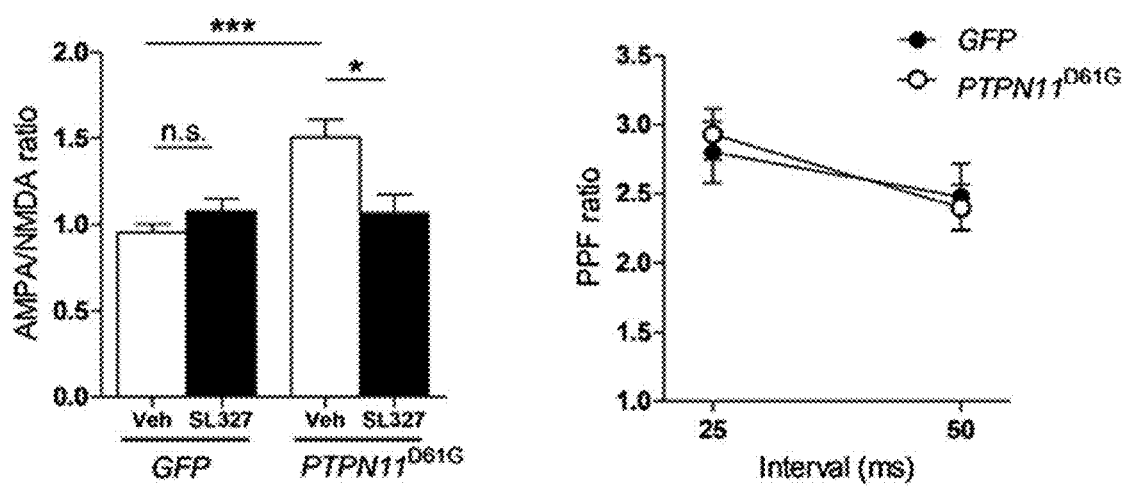
Figure 4:
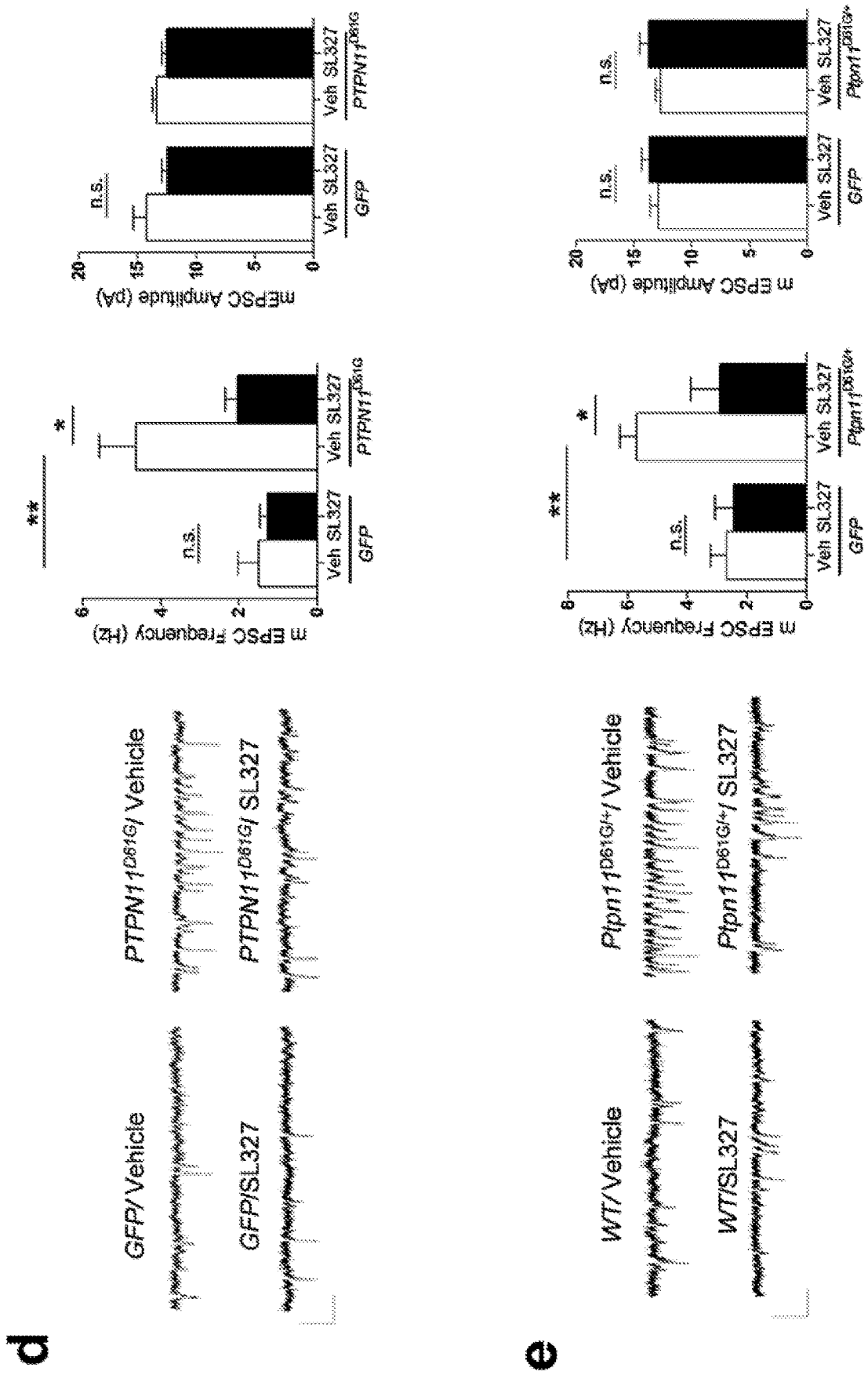

FIG. 4 are graphs showing PTPN11$^{D61G}$ overexpression enhances excitatory synaptic function through increased Ras-Erk signaling. Panel a) AMPA receptor-mediated currents were measured at the peak of the currents at −65 mV, and NMDA currents were measured 50 ms after onset at +40 mV. The average of 15 traces is shown. Scale, 100 pA and 40 ms. Panel b) Group data showing the increased AMPA:NMDA current ratio in AAV-PTPN11$^{D61G}$ mice (1.51±0.11, n=10 cells from 5 mice) compared with AAV-GFP mice (0.96±0.05, n=10 cells from 5 mice, t-test, ***P<0.001). SL327 treatment (1 μM, 1 hr) significantly reversed the AMPA:NMDA current ratio in the PTPN11$^{D61G}$ group without affecting GFP-expressing mice (PTPN11$^{D61G}$/SL327, 1.07±0.11, n=7 cells from 6 mice; GFP/SL327, 1.08±0.07, n=8 cells from 6 mice; PTPN11$^{D61G}$/Veh vs. PTPN11$^{D61G}$/SL327, t-test, *P<0.05). Two-way ANOVA, interaction between viral treatment and drug, F(1, 31)=10.53, P<0.01. Bonferroni post-test reveals significant effect of SL327 treatment only on PTPN11$^{D61G}$ group (P<0.01). Panel c) Paired-pulse facilitation ratio is unaffected by PTPN11$^{D61G}$. There was no significant difference at 25 ms or 50 ms intervals between two groups (AAV-PTPN11$^{D61G}$, n=12 cells from 5 mice; AAV-GFP, n=11 cells from 5 mice). Repeated-measures ANOVA, F(1, 21)=0.010, P=0.921. Panel d) PTPN11$^{D61G}$ overexpression increases excitatory synaptic function. mEPSC frequency was increased in AAV-PTPN11$^{D61G}$-infected mice compared with AAV-GFP mice, and was reversed by SL327 (1 µM) treatment without affecting on the AAV-GFP group. mEPSC frequency: GFP/Veh, 1.50±0.53, n=9; PTPN11$^{D61G}$/Veh, 4.64±0.94, n=9; GFP/SL327, 1.28±0.19, n=7; PTPN11$^{D61G}$/SL327, 2.02±0.32, n=9; Two-way ANOVA with viral treatment as between-subjects factor, F(1, 30)=10.31, P<0.01. GFP/Veh vs. PTPN11$^{D61G}$/Veh, t-test, P<0.01; PTPN11$^{D61G}$/Veh vs. PTPN11$^{D61G}$/SL327, t-test, P<0.5. mEPSC amplitudes were not significantly different among groups. Two-way ANOVA with viral treatment as between-subjects factor, F(1, 30)=0.470, P=0.498. Scale, 20 pA and 200 ms. Panel e) Excitatory synaptic function is increased in Ptpn11$^{D61G/+}$ mice and reversed by SL327 treatment. mEPSC frequency was increased in Ptpn11$^{D61G/+}$ mice compared with WT littermates, and was reversed by SL327 (1 µM) treatment. mEPSC frequency: WT/Veh, 2.68±0.55, n=9; Ptpn11$^{D61G/+}$/Veh, 5.71±0.56, n=10; WT/SL327, 2.46±0.63, n=9; Ptpn11$^{D61G/+}$/SL327, 2.87±1.02, n=9; Two-way ANOVA with genotype as between-subjects factor, F(1, 33)=5.914, *P<0.05. WT/Veh vs. Ptpn11$^{D61G/+}$/Veh, t-test, **P<0.01; Ptpn11$^{D61G/+}$/Veh vs. Ptpn11$^{D61G/+}$/SL327, t-test, *P<0.05. mEPSC amplitudes were not significantly different among groups. Two-way ANOVA with genotype as between-subjects factor, F(1, 33)=0.418, P=0.839. Scale, 20 pA and 200 ms.

Figure 5:
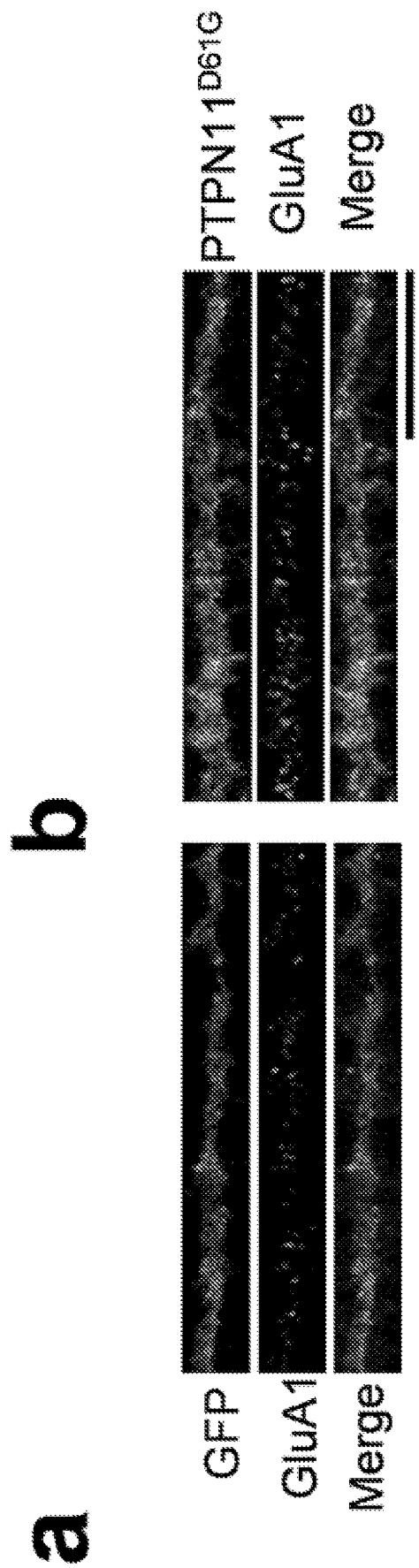
Figure 5:
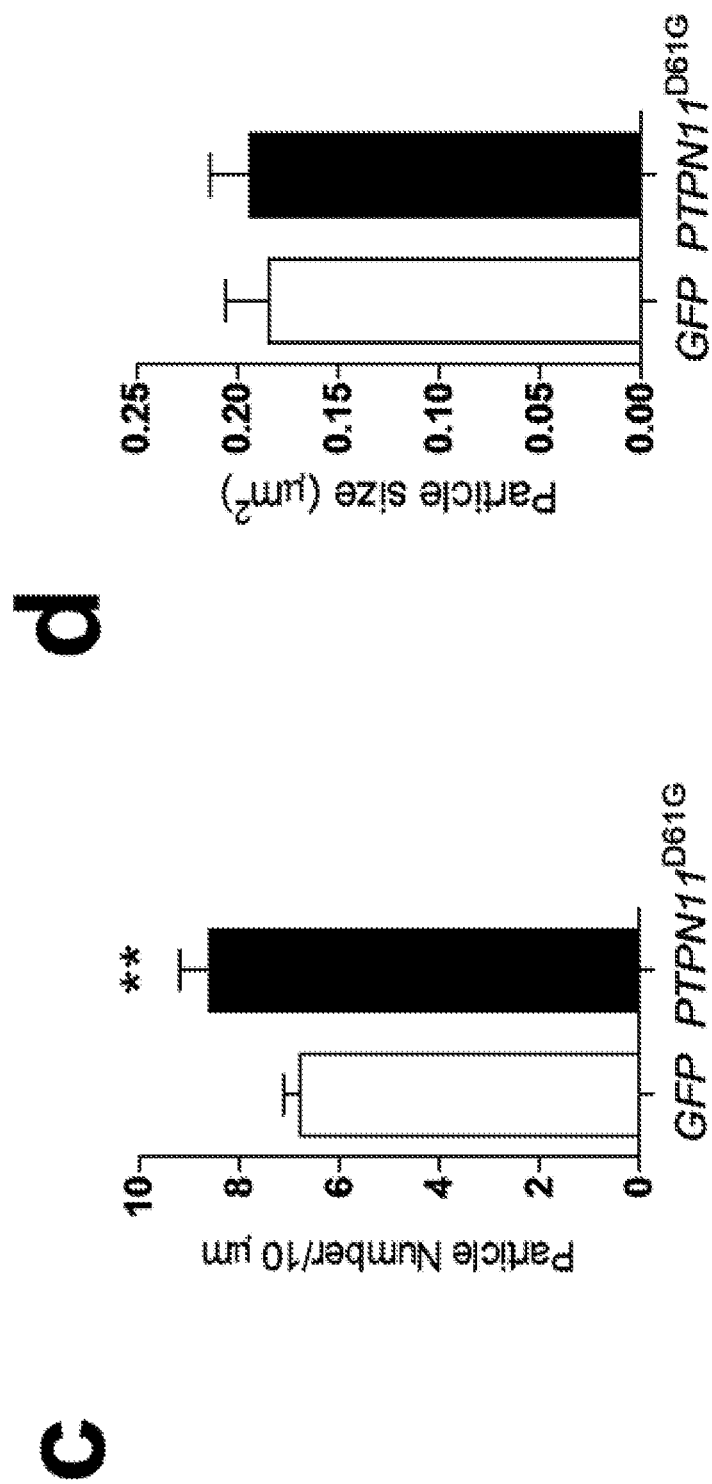

FIG. 5 are graphs showing PTPN11$^{D61G}$ overexpression increases surface AMPAR expression. Panels a-b) GFP alone (Panel a) or PTPN11$^{D61G}$ and GFP (Panel b) were co-expressed by using bicistronic Sindbis viral vector in cultured hippocampal neurons (DIV21). Scale, 20 µm. Panel c) The number of GluA1 clusters was significantly increased in PTPN11$^{D61G}$ infected neurons compared with GFP-infected control neurons. GluA1 particle number/10 µm: PTPN11$^{D61G}$, 8.60±0.59, n=20 neurons, 1,432.6 µm of dendrites; GFP, 6.76±0.34, n=22 neurons, 1759.6 µm of dendrites; t-test, **P<0.01. Panel d) The size of GluA1 clusters was not affected by PTPN11$^{D61G}$ expression. GluA1 particle size (µm$^2$): PTPN11$^{D61G}$, 0.19±0.02, n=20 neurons, 1,432.6 µm of dendrites; GFP, 0.18±0.02, n=22 neurons, 1759.6 µm of dendrites; t-test, P=0.751.

Figure 6:
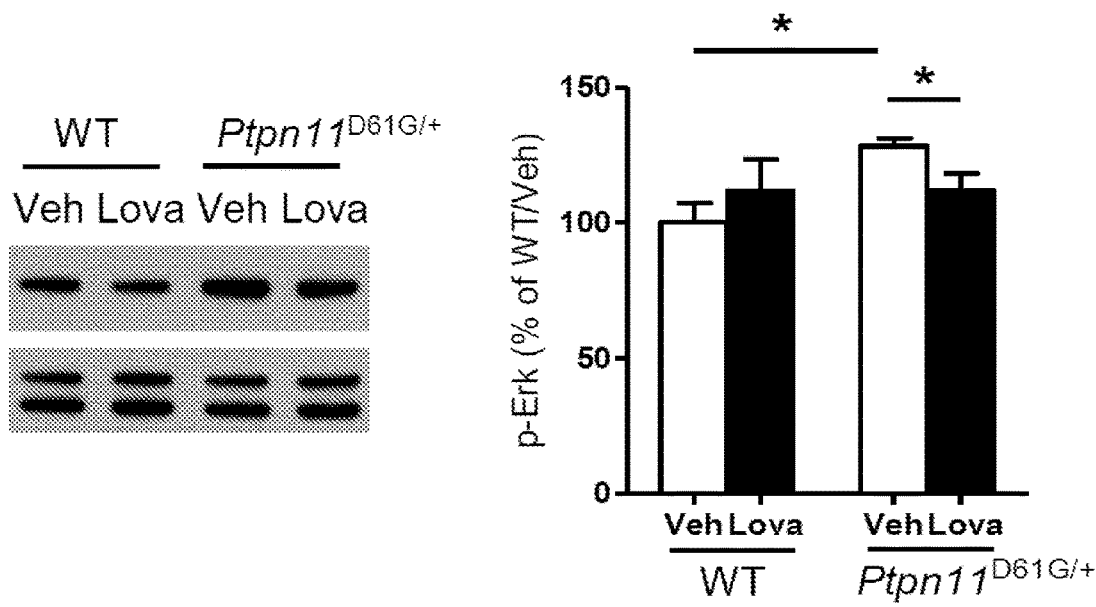
Figure 6:
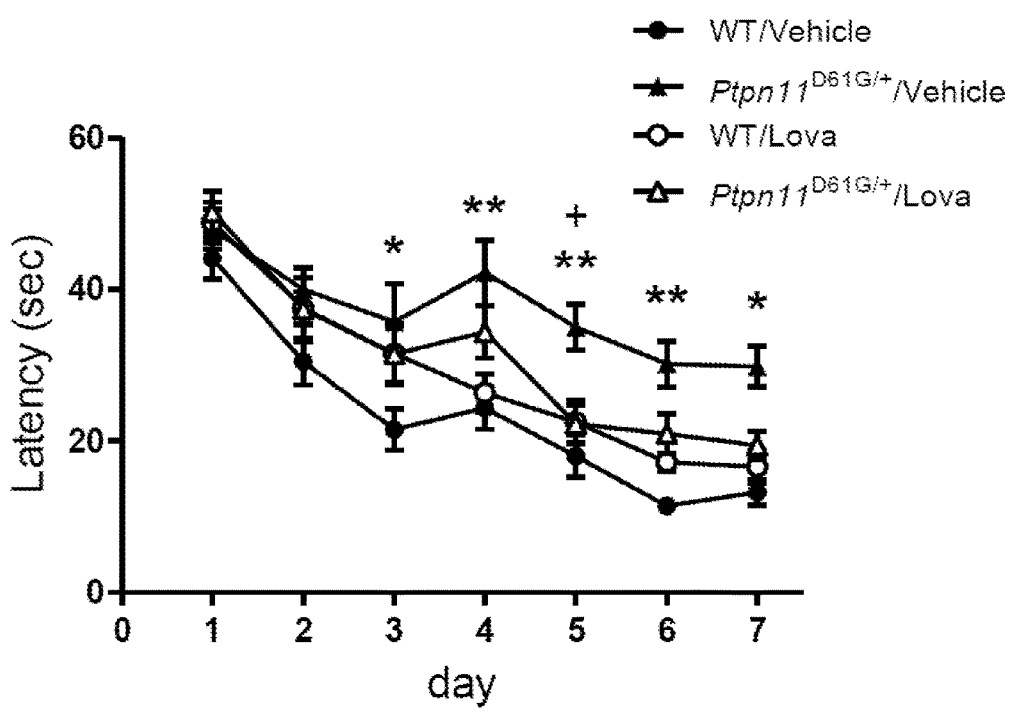
Figure 6:
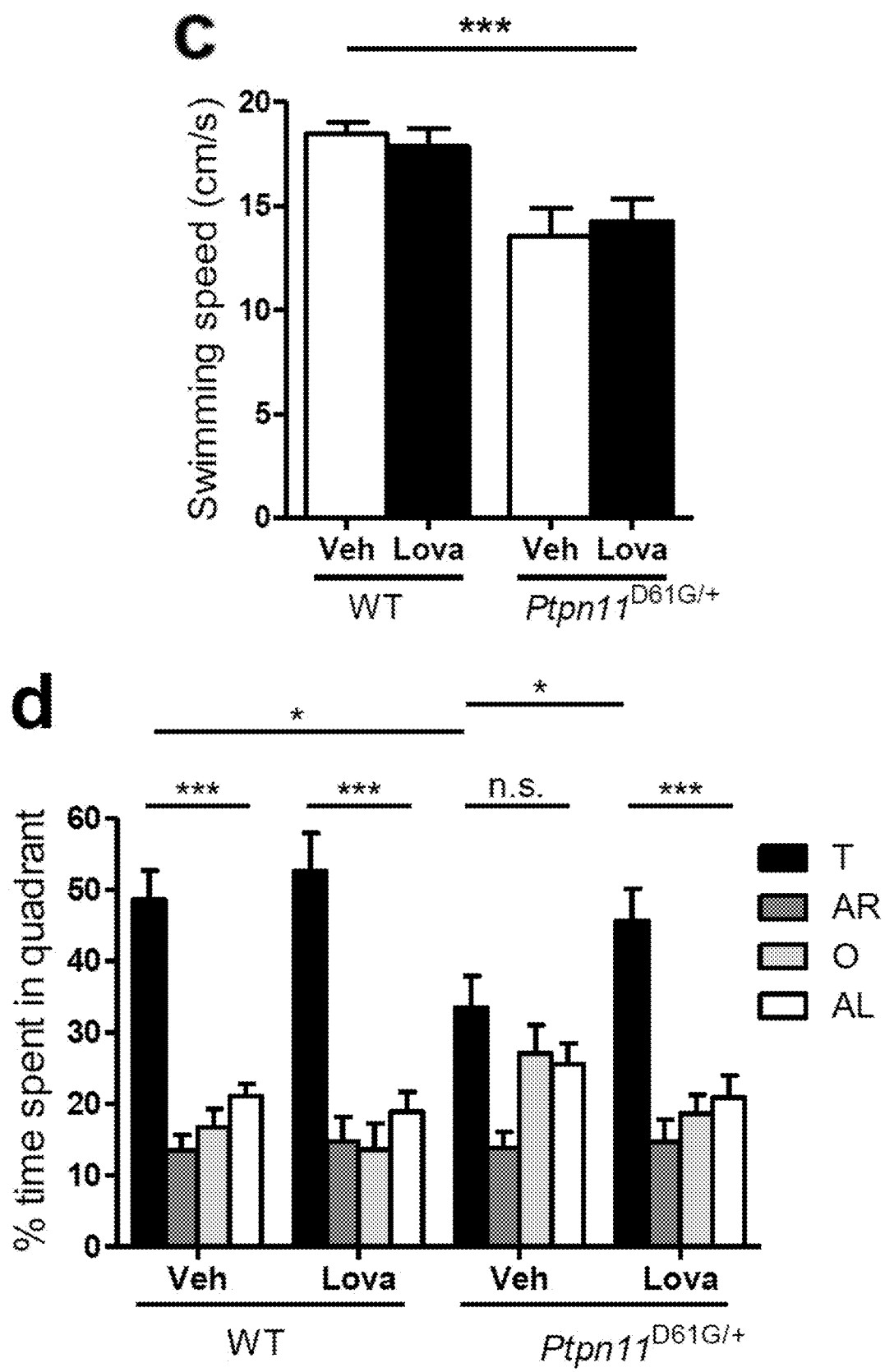
Figure 6:
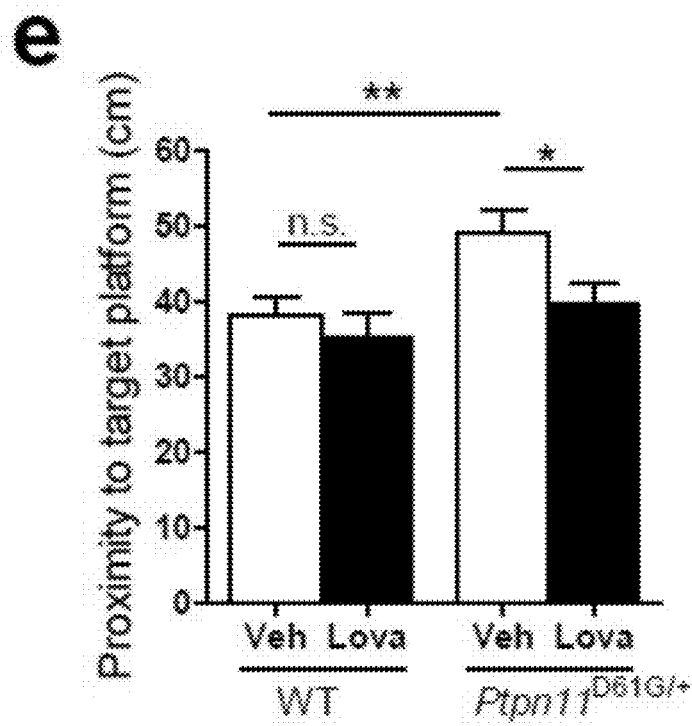
Figure 6:
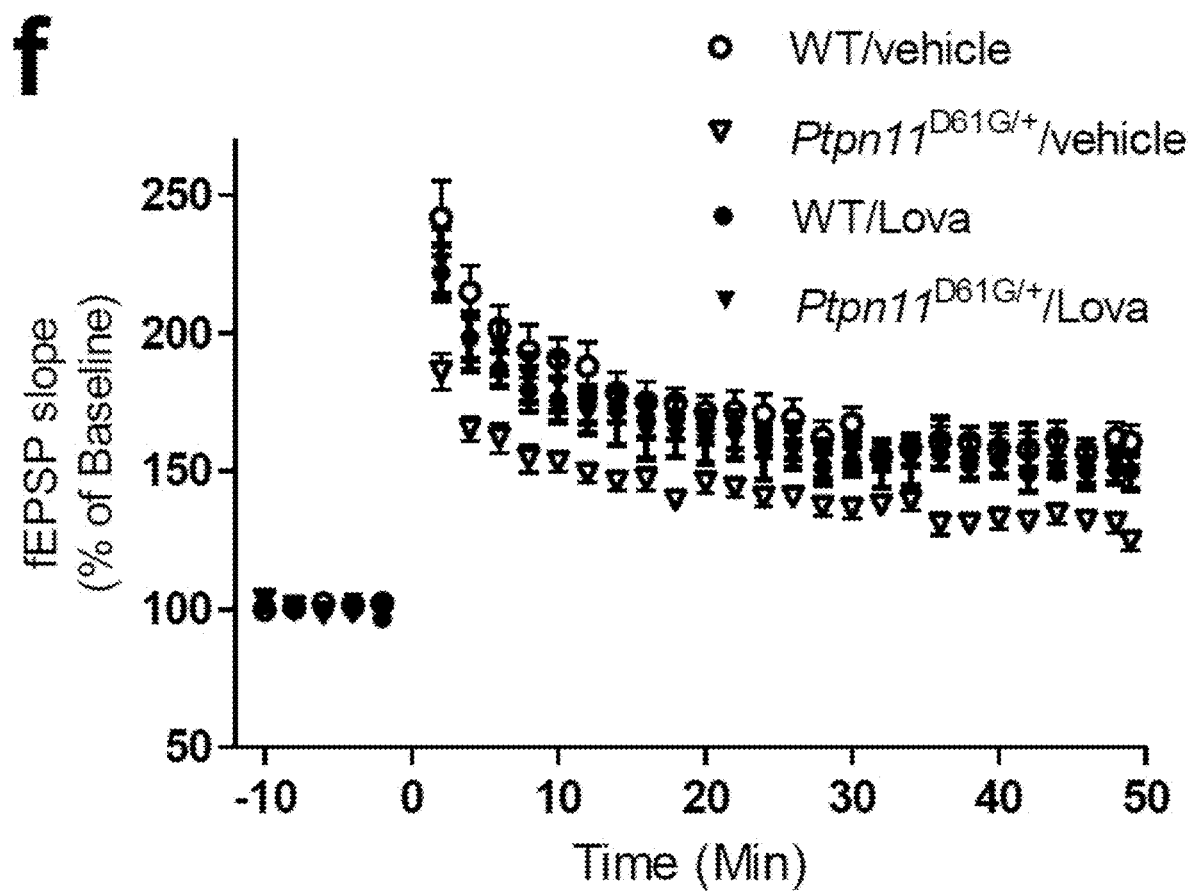
Figure 6:
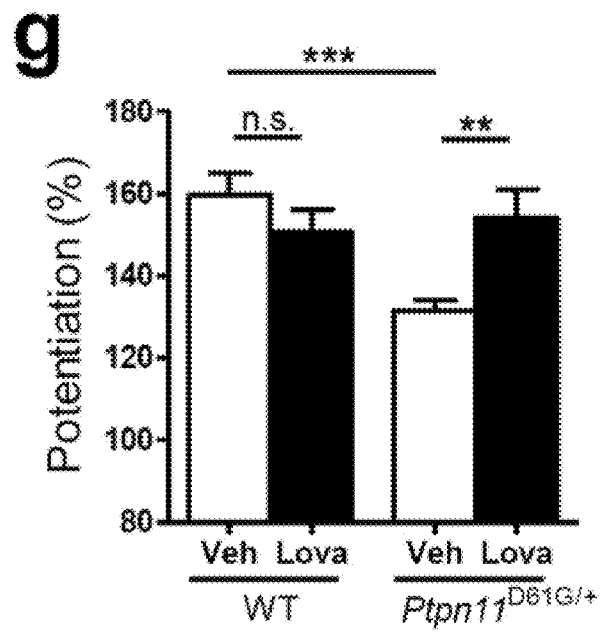

FIG. 6 are graphs showing that Lovastatin treatment reverses spatial learning and memory and LTP deficits in Ptpn11$^{D61G/+}$ mice. Panel a) Lovastatin treatment reverses increased Erk activation in Ptpn11$^{D61G/+}$ hippocampi. Left, Representative immunoblot showing p-Erk (upper) and total Erk (lower) levels in Ptpn11$^{D61G/+}$ mice and WT. Hippocampi were dissected 6 hr after the 4th day of lovastatin injection (subcutaneous (s.c.) injections, 10 mg/kg). Right, Bar graph displaying normalized p-Erk levels (mean±s.e.m.). n=7-8 per group. t-test, *P<0.05. Panel b) Vehicle-treated mutant mice showed significantly longer latency to the hidden platform during training sessions compared with vehicle-treated WT mice. Lovastatin-treated Ptpn11$^{D61G/+}$ mice showed comparable latency to WT mice. Two-way ANOVA followed by Bonferroni post-test, WT/Veh vs. Ptpn11$^{D61G/+}$/Veh, *P<0.05, P<0.01; Ptpn11$^{D61G/+}$/Veh vs. Ptpn11$^{D61G/+}$/Lova, +P<0.05. Panel c) Lovastatin treatment did not improve swimming speed (WT/veh, 18.5±0.6 cm/s, n=14; D61G/veh, 13.6±1.3 cm/s n=11; WT/lova, 17.9±0.8 cm/s, n=13; D61G/lova, 14.2±1.1 cm/s, n=11). Two-way ANOVA with genotype as between-subjects factor and drug treatment as within-subjects factor, effect of genotype: F(1, 45)=19.79, *P<0.0001, interaction: F (1,45)=0.4489, P=0.506. Panels d and e) Lovastatin treatment (10 mg/kg) reverses spatial memory deficits in Ptpn11$^{D61G/+}$ mice at a concentration that does not affect WT controls. Panel d) Quadrant occupancy analysis for the probe trail reveals that Ptpn11$^{D61G/+}$/veh showed no preference for the target quadrant (TQ vs. other quadrants, Dunnett's Multiple Comparison Test after one-way ANOVA, P>0.05). By contrast, the Ptpn11$^{D61G/+}$/Lova group selectively searched for the target quadrant, suggesting that lovastatin treatment reversed the spatial memory deficit in Ptpn11$^{D61G/+}$ mice (TQ vs. other quadrants, Dunnett's Multiple Comparison Test after one-way ANOVA, ***P<0.0001). The Ptpn11$^{D61G/+}$/Lova group also spent significantly more time in the target quadrant compared with Ptpn11$^{D61G/+}$/veh mice (Ptpn11$^{D61G/+}$/Lova, 45.70±4.43%, n=11; Ptpn11$^{D61G/+}$/veh, 33.48±4.44%, n=11; t-test, *P<0.05). Panel e) Proximity analysis reveals that the spatial memory deficit in Ptpn11$^{D61G/+}$ mice can be reversed by lovastatin treatment (WT/veh, 38.26±2.33 cm, n=14; WT/Lova, 35.28±3.26 cm, n=13; Ptpn11$^{D61G/+}$/veh, 49.05±3.15 cm, n=11; Ptpn11$^{D61G/+}$/Lova, 39.82±2.53 cm, n=11; t-test, *P<0.05, P<0.01). Panels f-g) Lovastatin treatment reverses LTP deficits in Ptpn11$^{D61G/+}$ mice at concentrations that do not affect WT littermates. Panel f) Ptpn11$^{D61G/+}$ mice showed deficit in 5 TBS-induced LTP that was reversed by systemic administrations of lovastatin (Repeated-measures ANOVA, F(3, 96)=14.38, P<0.0001). Panel g) Average % fEPSP changes (last 10 minutes of recordings) show that lovastatin treatment significantly rescued LTP deficit in Ptpn11$^{D61G/+}$ mice (WT/veh, 159.6±5.33%, n=7; WT/Lova, 150.7±5.49%, n=6; Ptpn11$^{D61G/+}$/veh, 131.7±2.31%, n==9; Ptpn11$^{D61G/+}$/Lova, 154.2±6.88%, n=7; t-test, P<0.01, ***P<0.001). Two-way ANOVA with genotype as between-subjects factor reveals significant effect of genotype, F(1, 25)=5.936, *P<0.05. Bonferroni post-test reveals significant effect of lovastatin treatment only on Ptpn11$^{D61G/+}$ group (**P<0.01).

Figure 7:
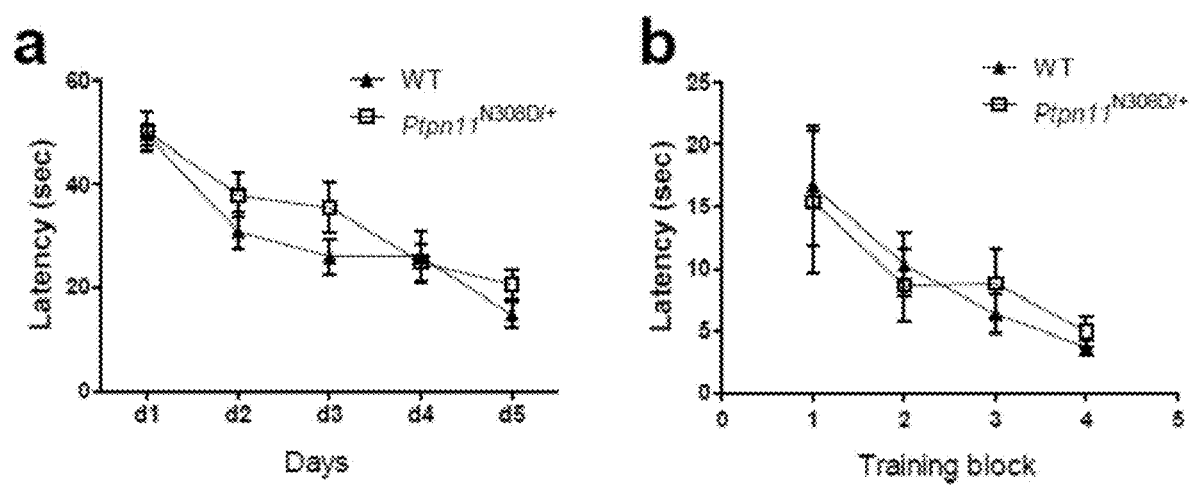
Figure 7:
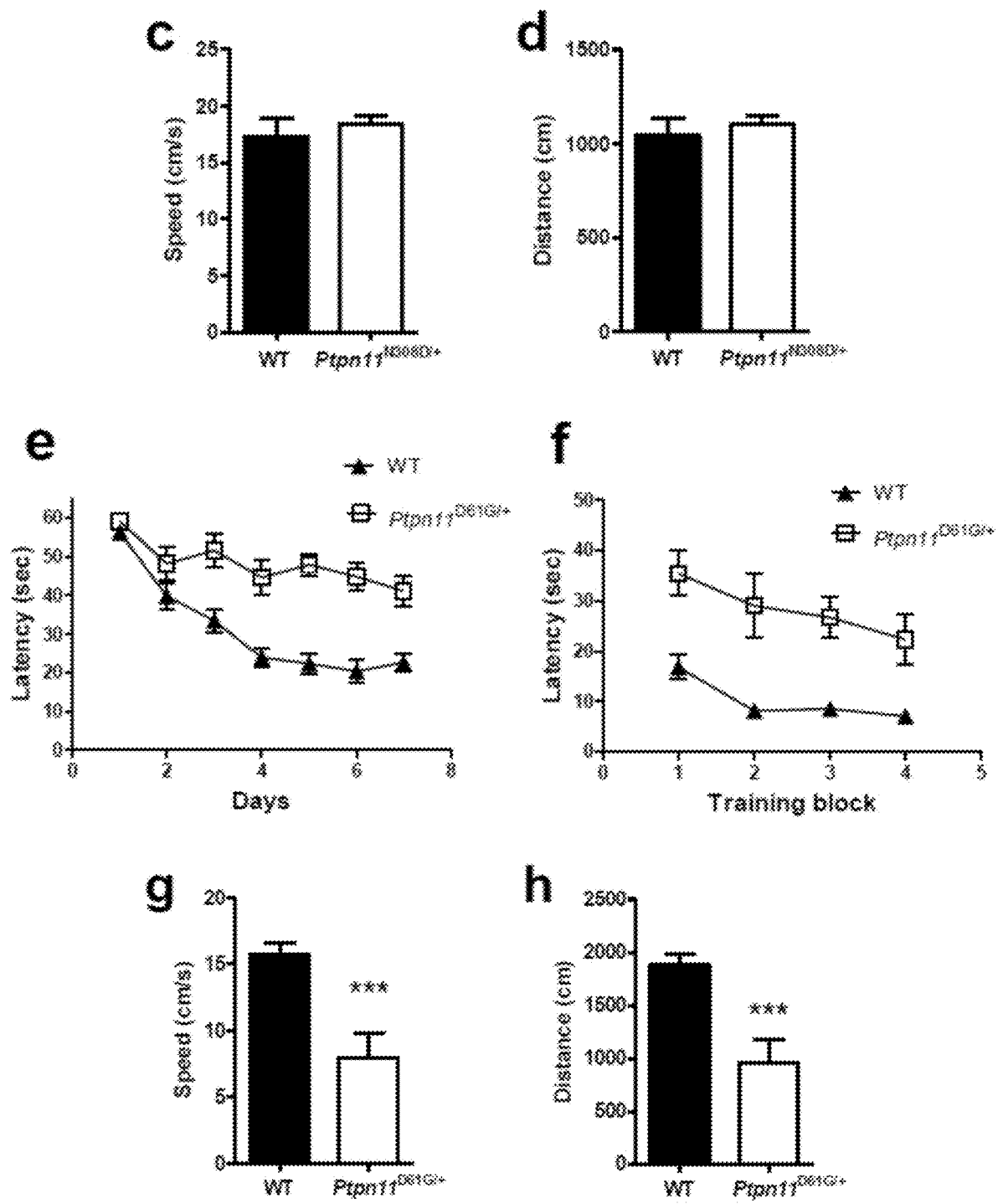

FIG. 7 are graphs showing the basal activity of Ptpn11$^{N308D/+}$ and Ptpn11$^{D61G/+}$ mutants. Panels a-d) Ptpn11$^{N308D/+}$ mutants and WT controls show comparable latencies to the target platform in the hidden and visible-version of water maze training. Panel a) Escape latencies of mutant mice (n=9) and WT littermates (n=11) were not different in the hidden platform version of the water maze. Repeated measures ANOVA with genotype as between-subjects factor, F(1, 18)=2.078, P=0.167. Panel b) Ptpn11$^{N308D/+}$ mice and WT showed comparable performance in the visible platform version of the water maze. F(1, 18)=0.003, P=0.954. c) Ptpn11$^{N308D/+}$ mutants and WT mice show comparable swimming speeds. t-test, P=0.586. Panel d) Total swimming distance during the probe trial was comparable between Ptpn11$^{N308D/+}$ mutants and WT controls. t-test, P=0.589. Panels e-f) Ptpn11$^{D61G/+}$ mutants are hypoactive. Panel e) Ptpn11$^{D61G/+}$ mutants showed significantly longer latency to the platform during training compared with WT controls in the hidden-platform version of the water maze. Repeated measures ANOVA with genotype as between-subjects factor, F(1, 23)=38.54, P<0.0001. Panel f) Ptpn11$^{D61G/+}$ mutants showed significantly longer latency to the platform during training compared to WT controls in the visible version of water maze. Repeated measures ANOVA with genotype as between-subjects factor, F(1, 23)=32.99, P<0.0001. Panels g-h) In an open field analysis (20 min duration), Ptpn11$^{D61G/+}$ mutant mice (n=10)

showed significantly slower speed and less travel distance than WT controls (n=15). t-test, ***P<0.0001.

Figure 8:
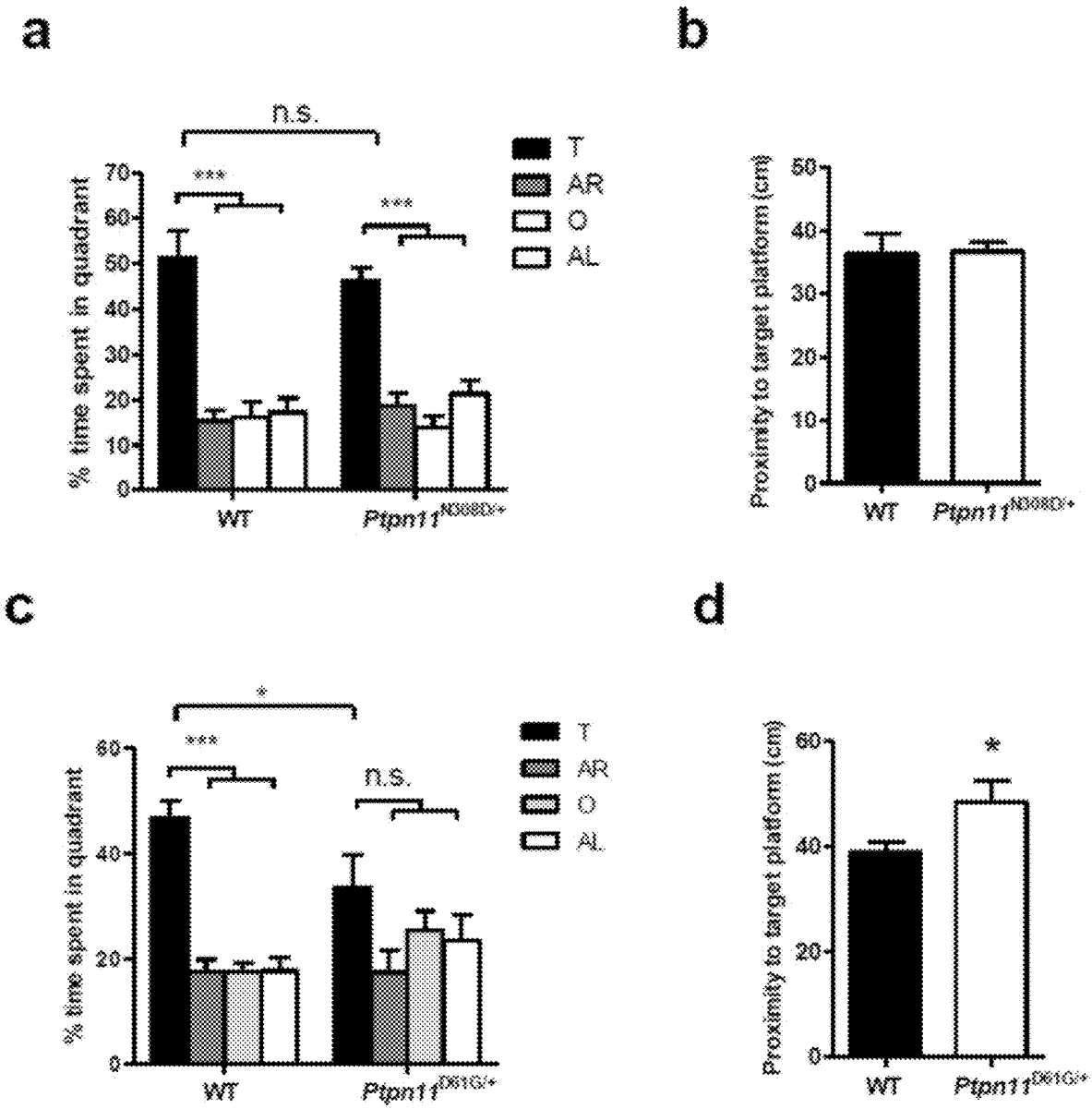

FIG. 8 show probe trials after extended trainings Panels a-b) Ptpn11$^{N308D/+}$ and WT controls show comparable memory after extended training. Quadrant occupancy (Panel a) and proximity analysis (Panel b) for the probe trial conducted after 5 days of training shows that there is no significant difference between Ptpn11$^{N308D/+}$ mutants and WT controls. Panels c-d) Ptpn11$^{D61G/+}$ show spatial memory deficits even with the additional trainings. Panel c) Quadrant occupancy for the probe trial conducted after 7 days of training reveals that Ptpn11$^{D61G/+}$ mice (n=10) show no preference for the target quadrant, unlike their WT littermates (n=15) ($F(3,36)=1.824$, P=0.160 and $F(3,56)=36.04$, ***P<0.0001 for Ptpn11$^{D61G/+}$ and WT, respectively; one-way ANOVA). In addition, Ptpn11$^{D61G/+}$ mice also spent significant less time in the target quadrant than WT mice (Ptpn11$^{D61G/+}$, 33.50±6.27%; WT, 46.79±3.17, *P<0.05; t-test). Pool quadrants; target (T), adjacent right (AR), opposite (O), and adjacent left (AL) quadrant. Panel d) Ptpn11$^{D61G/+}$ showed significantly longer proximity to the target platform than WT mice in the probe trial given after 7 days training (Ptpn11$^{D61G/+}$, 48.34±4.11 cm; WT, 38.77±2.01 cm, *P<0.05; t-test).

Figure 9:
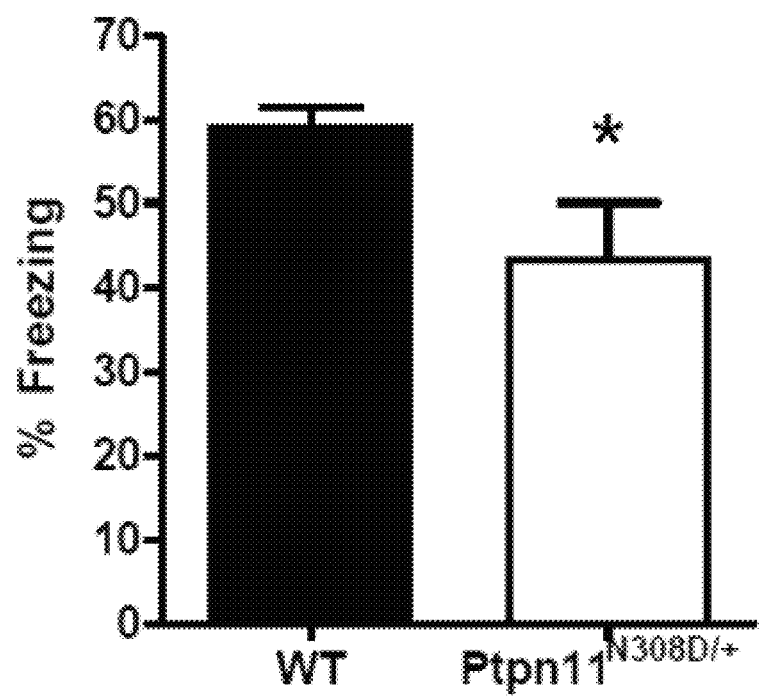

FIG. 9 shows Ptpn11$^{N308D/+}$ mutants exhibit deficit in contextual fear conditioning. Mice were trained with two shocks (0.5 mA, 2 sec, 1 hr interval) for two days and contextual fear memory was assessed for 3 min in the training chamber on the 3$^{rd}$ day. Freezing (%): WT, 58.91±2.50, n=20; Ptpn11$^{N308D/+}$, 43.20±6.82, n=15; *P<0.05; t-test.

Figure 10:
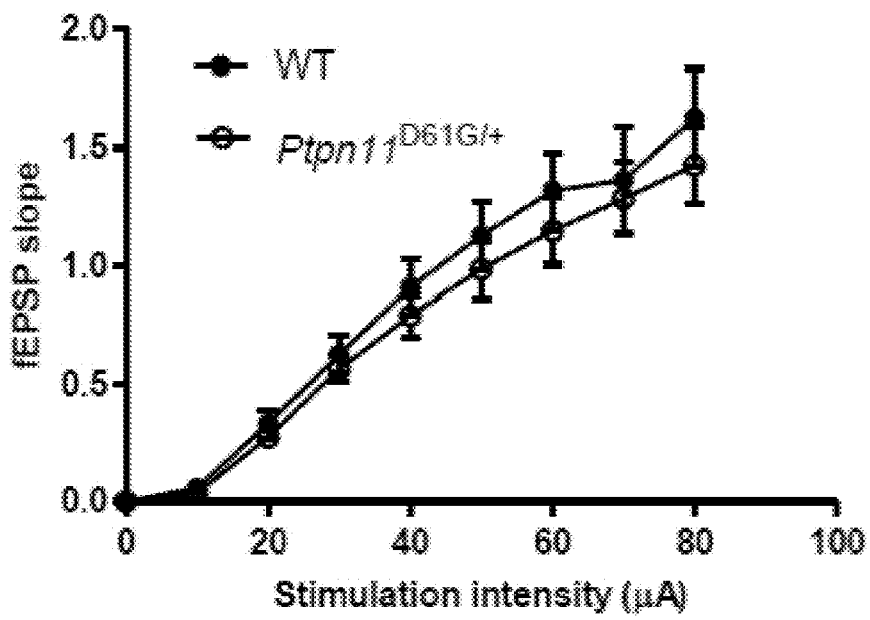
Figure 10:
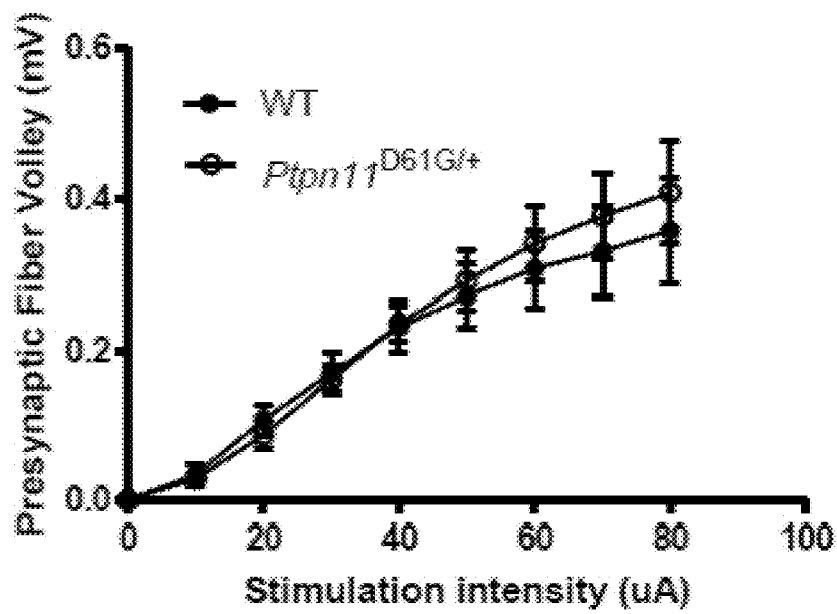
Figure 10:
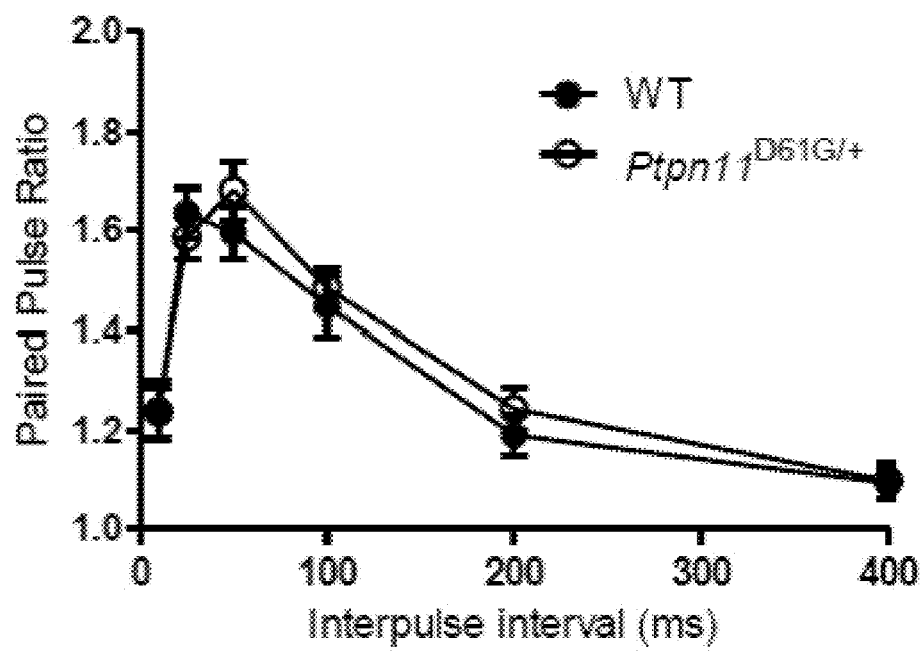
Figure 10:
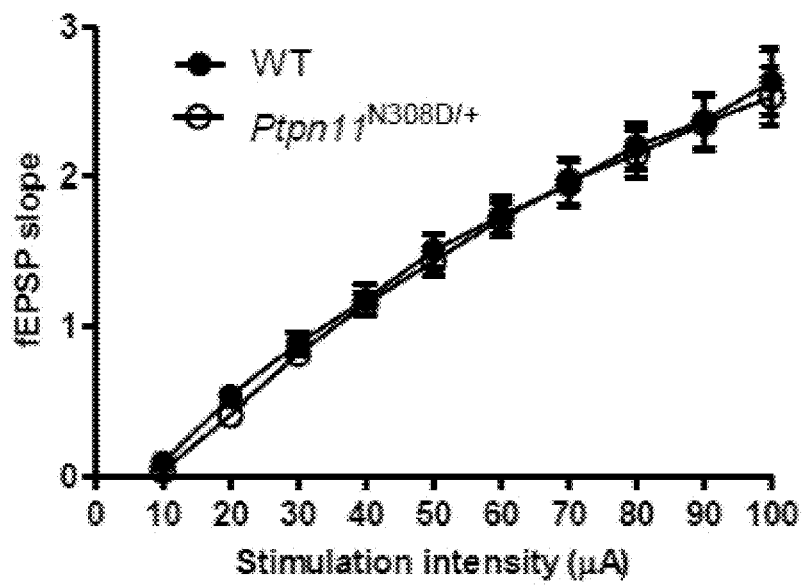
Figure 10:
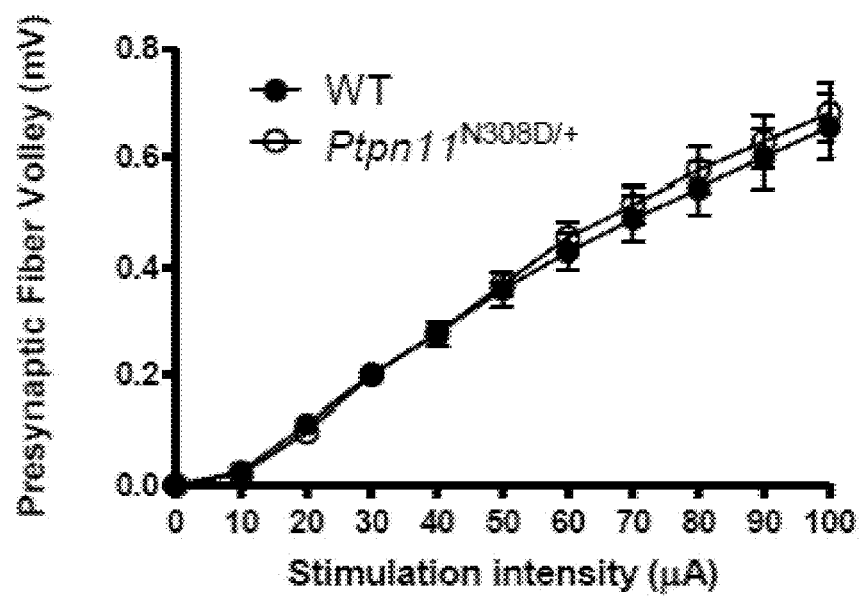
Figure 10:
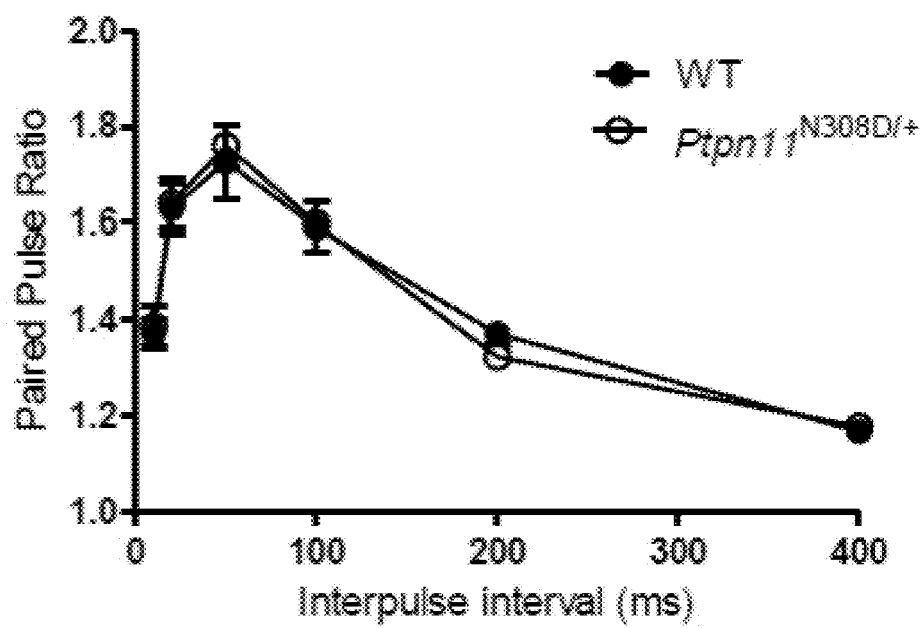

FIG. 10 show the basal synaptic transmission and paired-pulse facilitation in NS mice. Panel a) Basal synaptic transmission was not changed in Ptpn11$^{D61G/+}$ mice (wild type, n=9 slices from 7 mice; Ptpn11$^{D61G/+}$, n=9 slices from 6 mice; Repeated-measures ANOVA, $F(1, 16)=0.502$, P=0.489). Plot shows the fEPSP slope as a function of stimulation intensity. Panel b) Presynaptic fiber volley sizes were not different between WT and Ptpn11$^{D61G/+}$ mice. Repeated-measures ANOVA, $F(1, 16)=0.104$, P=0.751. Plot shows the fiber volley size as a function of stimulation intensity. Panel c) Paired-pulse facilitation was not changed in Ptpn11$^{D61G/+}$ mice. Repeated-measures ANOVA, $F(1, 15)=0.183$, P=0.674. Panel d) Basal synaptic transmission was normal in Ptpn11$^{N308D/+}$ mice (wild type, n=13 slices from 7 mice; Ptpn11$^{N308D/+}$, n=11 slices from 6 mice). Panel e) Presynaptic fiber volley sizes were not different between WT and Ptpn11$^{N308D/+}$ mice. Repeated-measures ANOVA, $F(1, 21)=0.107$, P=0.747. Plot shows the fiber volley size as a function of stimulation intensity. Panel f) Paired-pulse facilitation was normal in Ptpn11$^{N308D/+}$— mice for different inter-stimulus intervals (wild type, n=8 slices from 6 mice; Ptpn11$^{N308D/+}$, n=9 slices from 5 mice).

Figure 11:
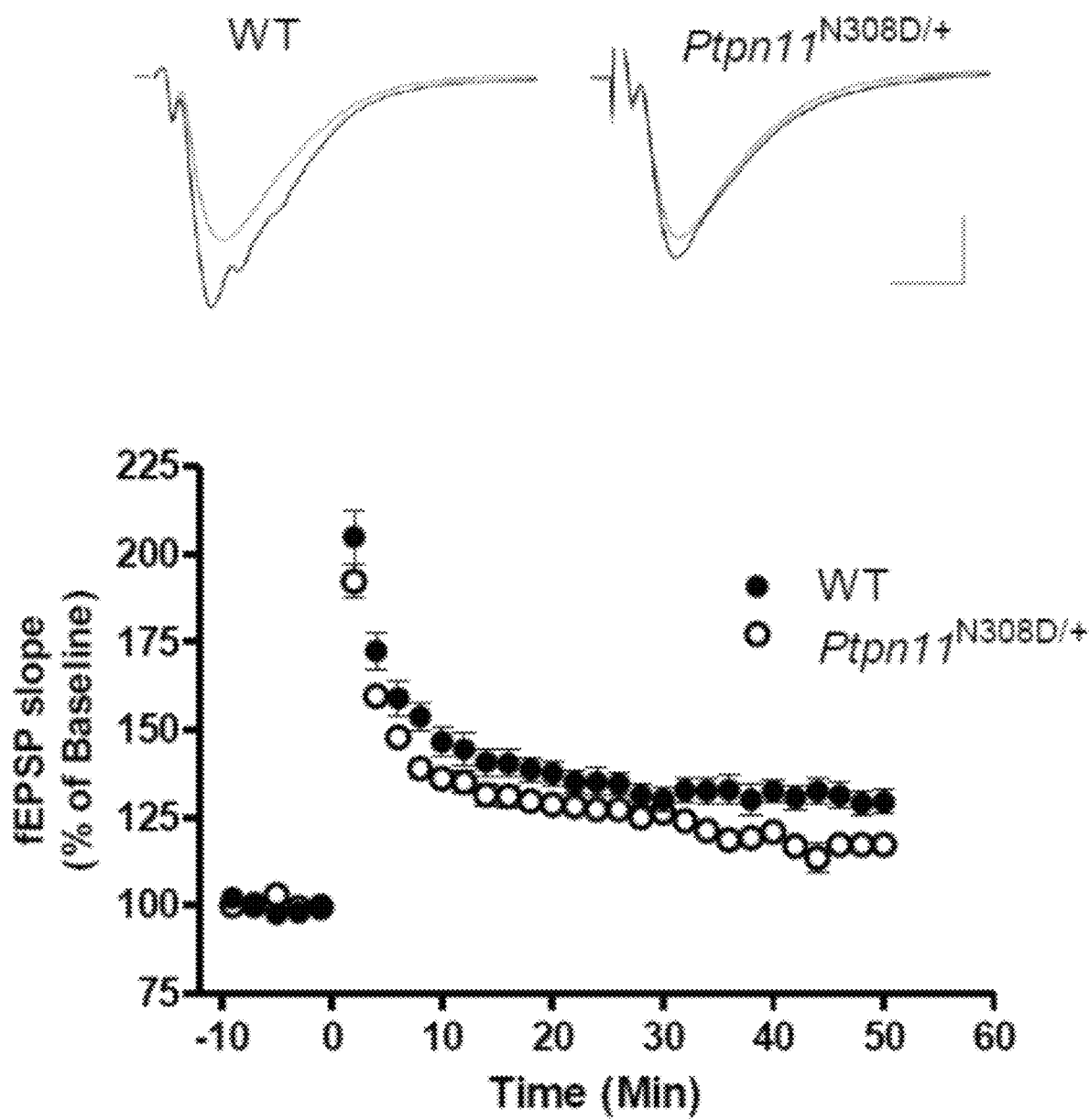

FIG. 11 show that Ptpn11$^{N308D/+}$ mutants exhibit LTP deficits with 2 TBS induction protocol. LTP induced by a 2 TBS protocol was significantly reduced in the hippocampal slices from Ptpn11$^{N308D/+}$ mice compared with their WT littermates (WT, n=10 slices from 7 mice; Ptpn11$^{N308D/+}$, n=11 slices from 6 mice; Repeated-measures ANOVA: $F(1, 19)=7.448$, P<0.05; last 10 min of recording, WT, 131.3±3.36%, Ptpn11$^{N308D/+}$, 117.0±2.02%, t-test, P<0.01). fEPSP slopes normalized to the average baseline response before LTP induction (at time 0) are plotted in 2-min blocks. Sample traces show responses during baseline (gray) and the last 10 min (black) of the recording (average of ten traces). Scale: vertical bar, 0.5 mV; horizontal bar, 4 ms. Error bars represent s.e.m.

Figure 12:
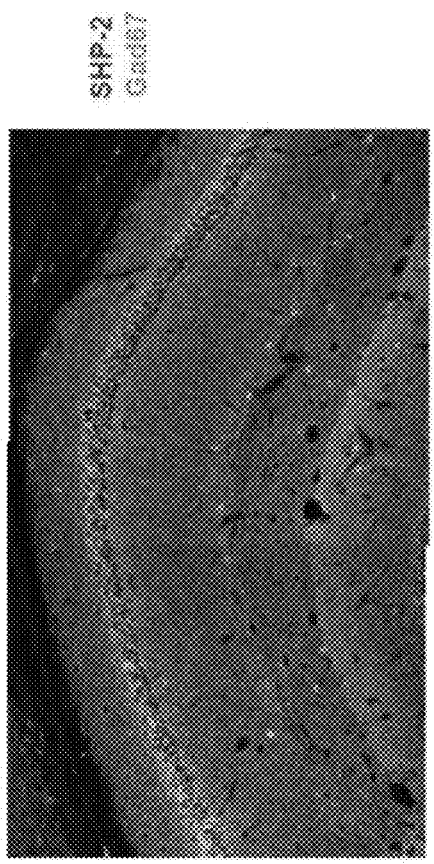
Figure 12:
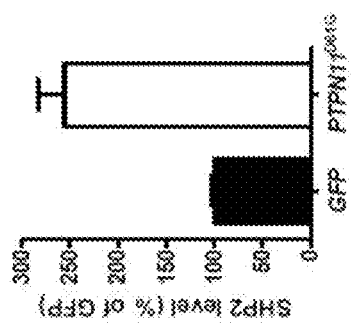
Figure 12:
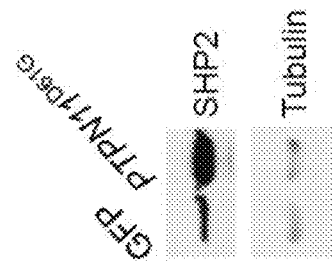

FIG. 12 the viral overexpression of AAV-PTPN11$^{D61G}$. Panel a) Western blot analysis confirmed the overexpression of SHP2 (255.6±27.69% in PTPN11$^{D61G}$-expressing hippocampus compared to GFP-expressing hippocampus, n=5 per group, P<0.001). Panel b) PTPN11$^{D61G}$-expressing slice was stained with SHP2 antibody together with Gad67 antibody as an inhibitory neuronal marker. Most of the SHP2 staining (dark grey) did not overlap with Gad67 (light grey).

Figure 13:
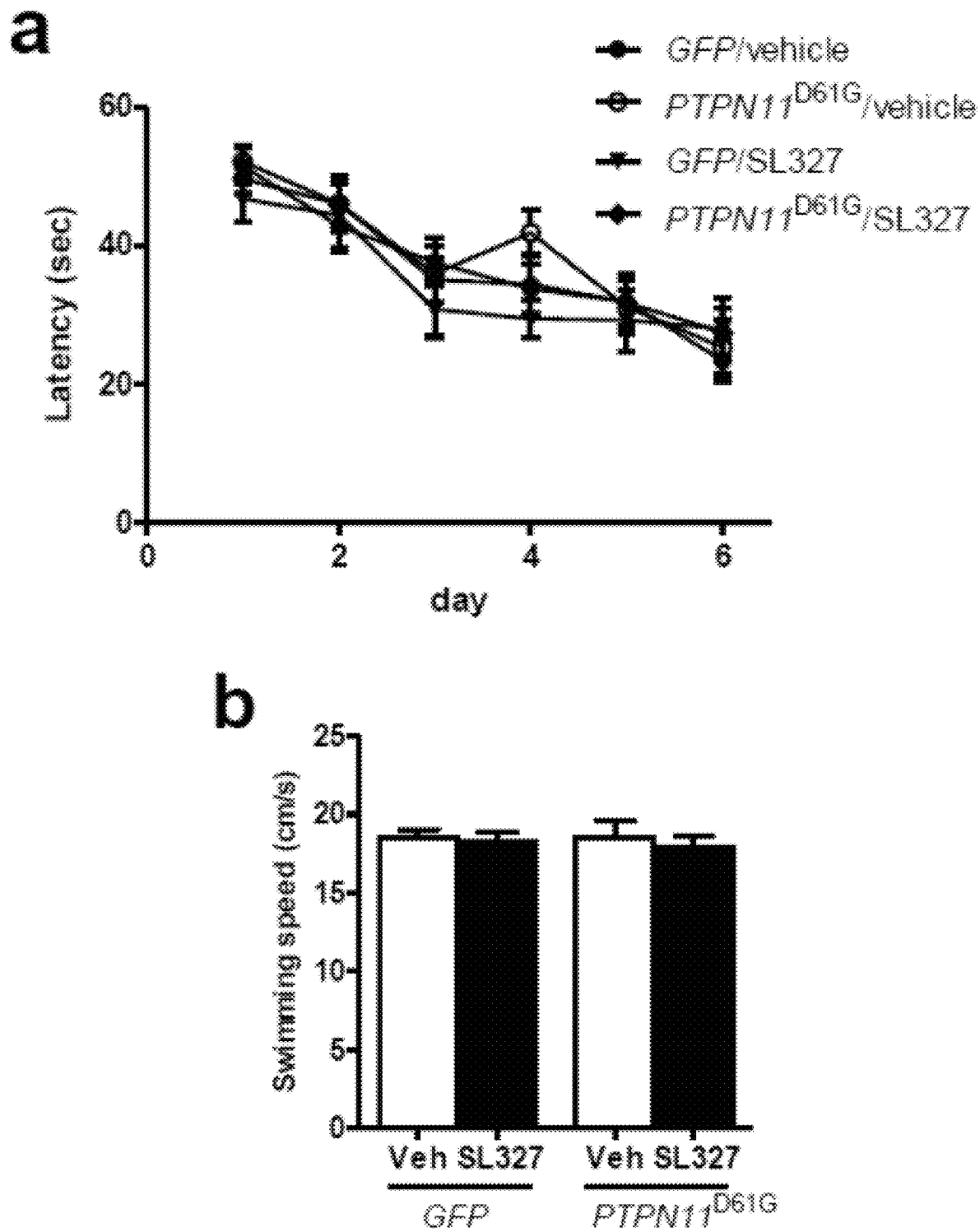
Figure 13:
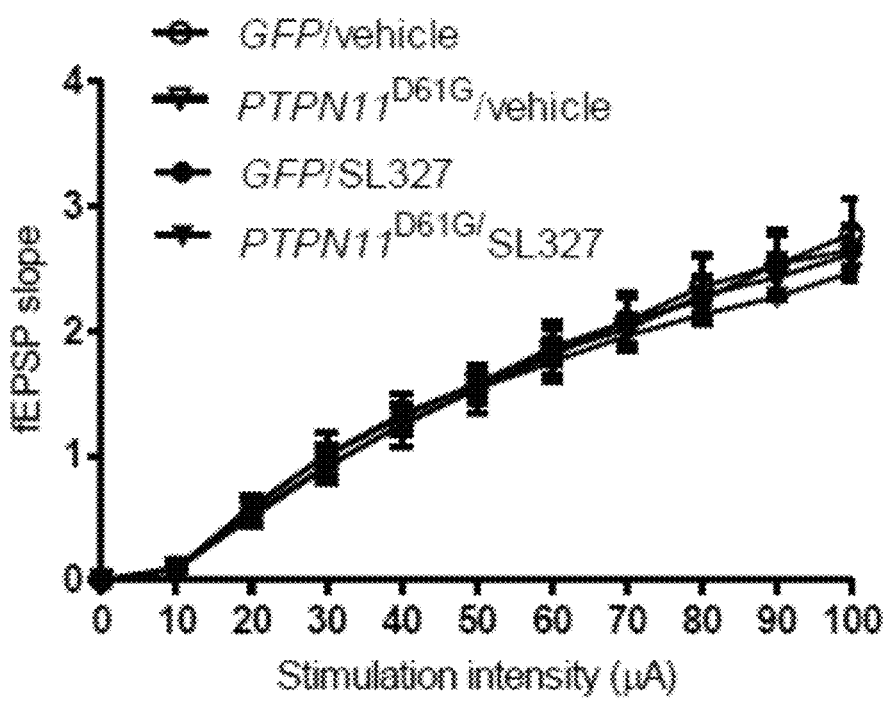
Figure 13:
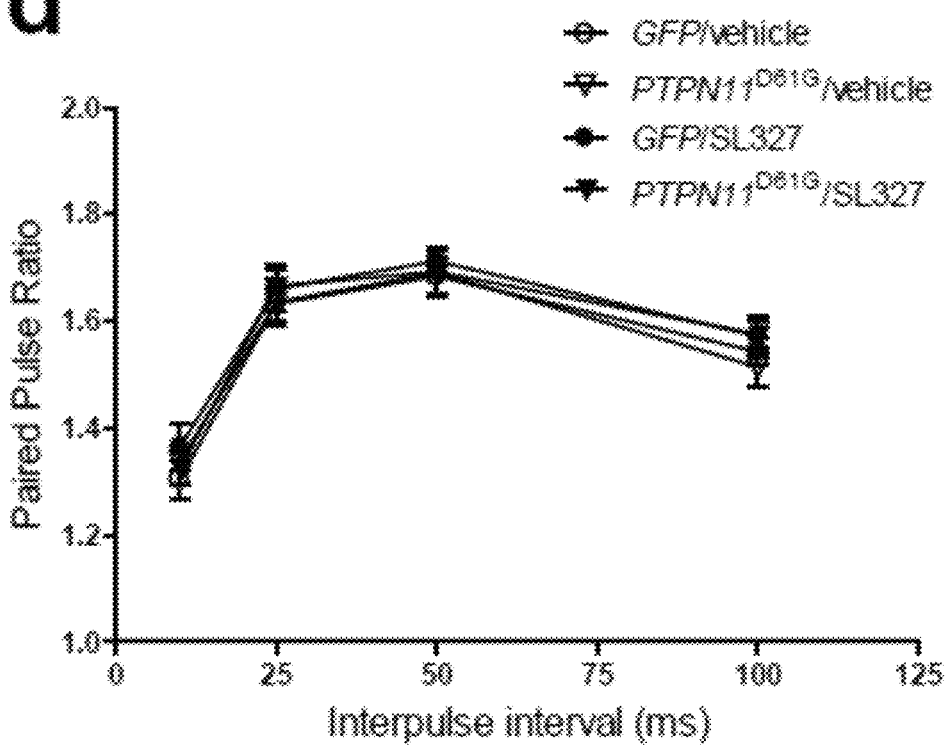

FIG. 13 show the effect of PTPN11$^{D61G}$ overexpression and SL327 treatment on behavior and basal synaptic transmission. Panels a-b) Effects on the acquisition of water maze or swimming speed. Panel a) For the latency to the platform during training, repeated-measures ANOVA revealed no difference among the groups ($F(3, 34)=0.618$, P=0.608). Panel b) Neither mutant PTPN11 overexpression nor SL327 treatment affect swimming speed in the probe trial (effect of virus, $F(1, 37)=0.054$, P=0.818; effect of treatment, $F(1, 37)=0.240$, P=0.627). Panels c-d) Basal synaptic transmission and paired-pulse facilitation in PTPN11$^{D61G}$ overexpressing slices. Panel c) Overexpression of PTPN11$^{D61G}$ or SL327 treatment did not affect the basal synaptic transmission in CA3-CA1 synapses. Repeated-measures ANOVA, $F(3, 36)=0.175$, P=0.912. Panel d) Paired-pulse facilitation was not affected by either PTPN11$^{D61G}$ overexpression or SL327 treatment. Repeated-measures ANOVA, $F(3, 35)=0.356$, P=0.785.

Figure 14:
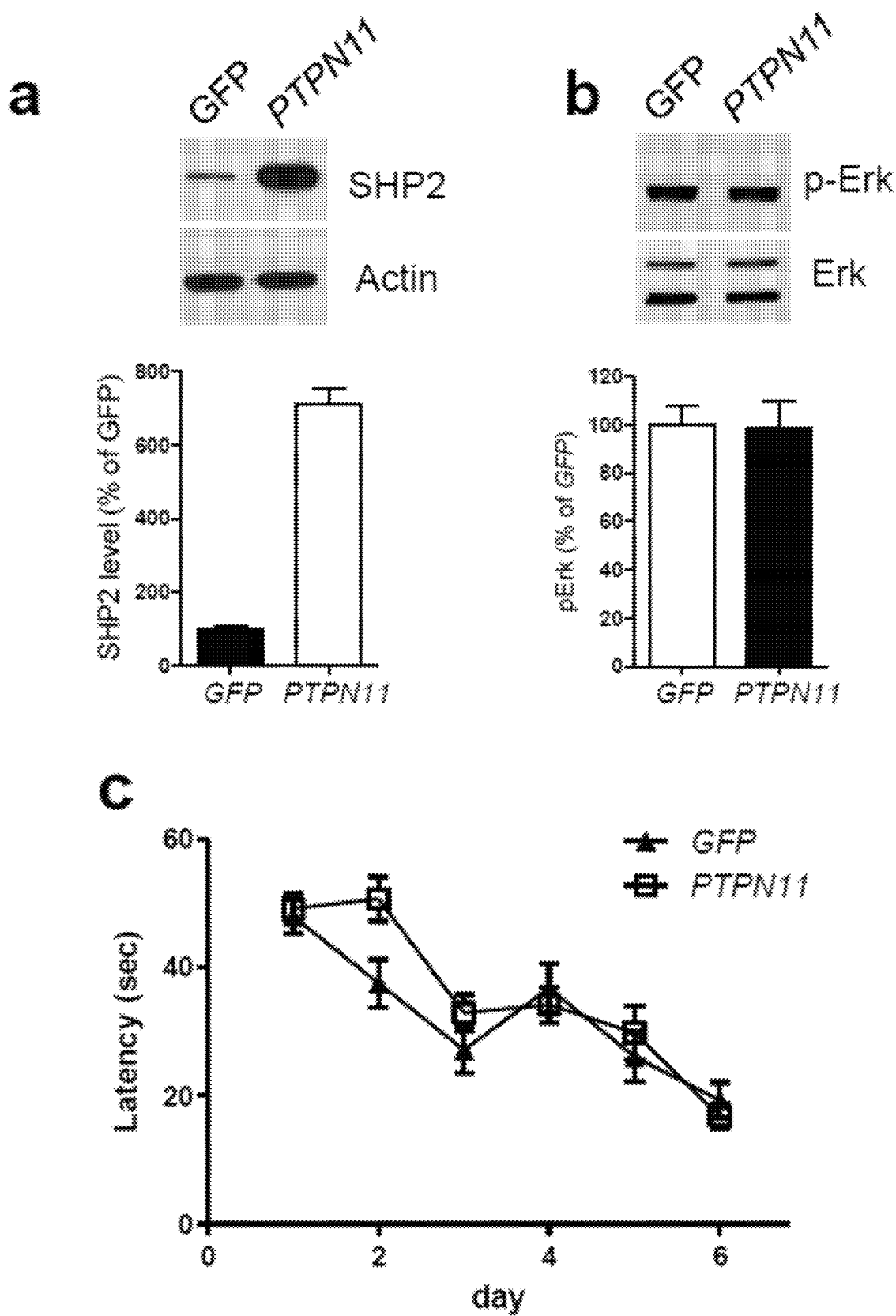
Figure 14:
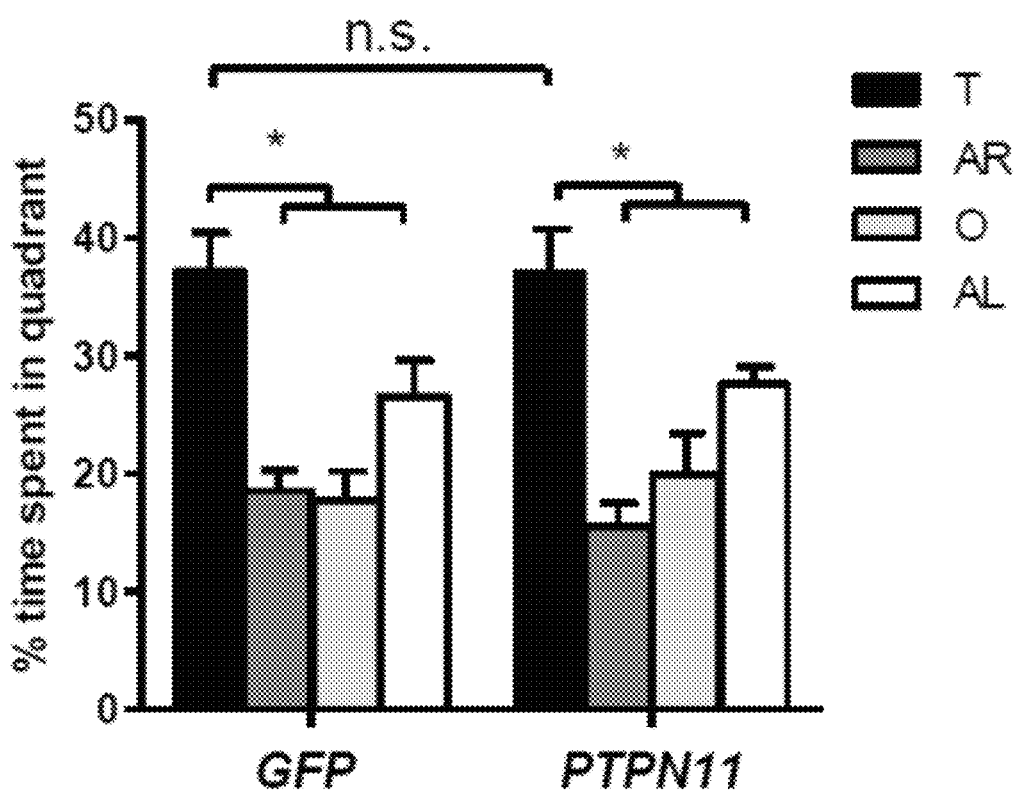
Figure 14:
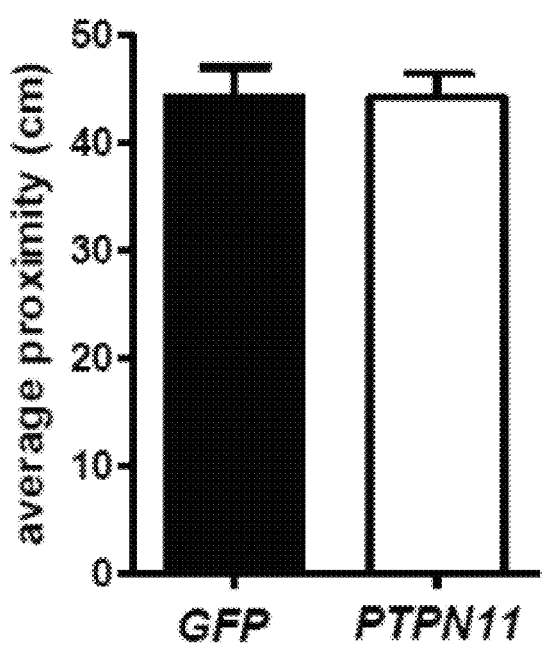

FIG. 14 show that wild-type PTPN11 overexpression does not affect either basal p-Erk level or learning and memory in water maze. Panel a) Western blot analysis confirmed the overexpression of SHP2 (711.4±42.2% in wild type PTPN11-expressing hippocampus compared to GFP-expressing hippocampus, n=5 per group, P<0.001). Panel b) Wild-type PTPN11 overexpression does not affect basal p-Erk level in the hippocampus. (Normalized p-Erk: PTPN11, 98.44±11.48%, n=5; WT, 100.00±7.53%, n=4). Panel c) For the latency to the platform during training in the hidden-platform version of Morris water maze, repeated-measures ANOVA revealed no difference between GFP (n=9) and PTPN11-overexpressing (n=12) mice ($F(1, 19)=1.518$, P=0.233). Panels d-e) Wild-type PTPN11- and GFP-expressing controls show comparable memory in the probe trial. Quadrant occupancy (Panel d) and proximity analysis (Panel e) shows that there is no significant difference between PTPN11- and GFP-expressing controls.

Figure 15:
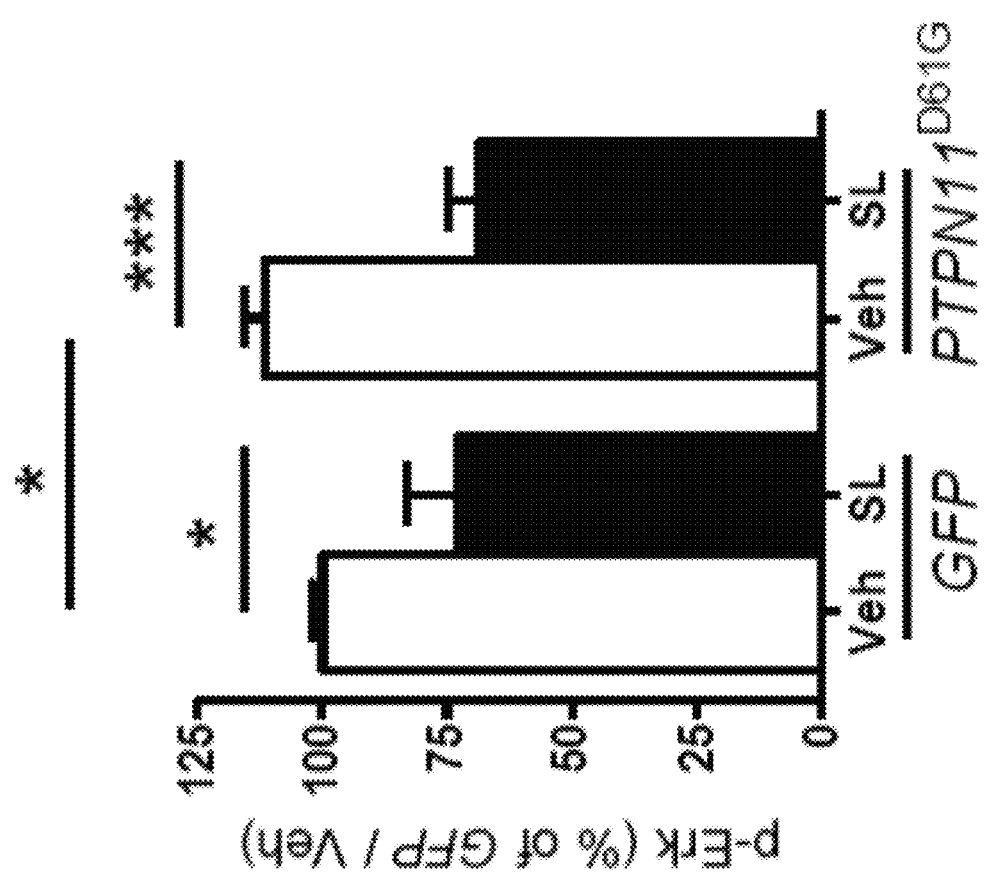
Figure 15:
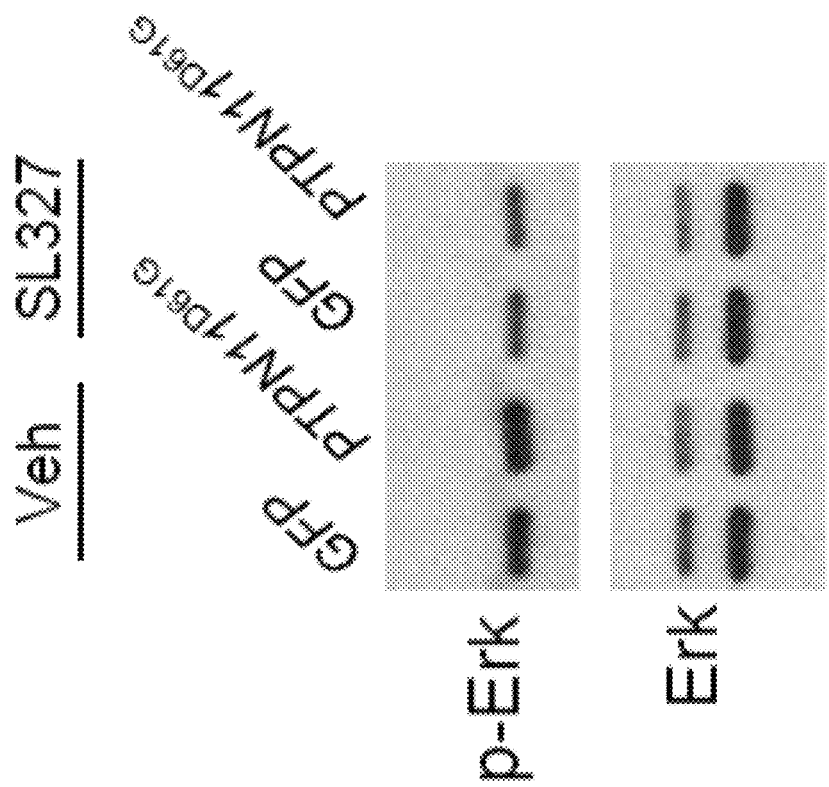

FIG. 15 shows the effects of SL327 treatment on p-Erk level in the hippocampus. SL327 treatment reverses increased Erk activation in PTPN11$^{D61G}$-expressing hippocampi. Left, Representative immunoblot showing p-Erk (upper) and total Erk (lower) in PTPN11$^{D61G}$-expressing and GFP-expressing hippocampi. Right, Bar graph displaying normalized p-Erk levels (mean±s.e.m). n=7-8 per group. t-test, *P<0.05.

Figure 16:
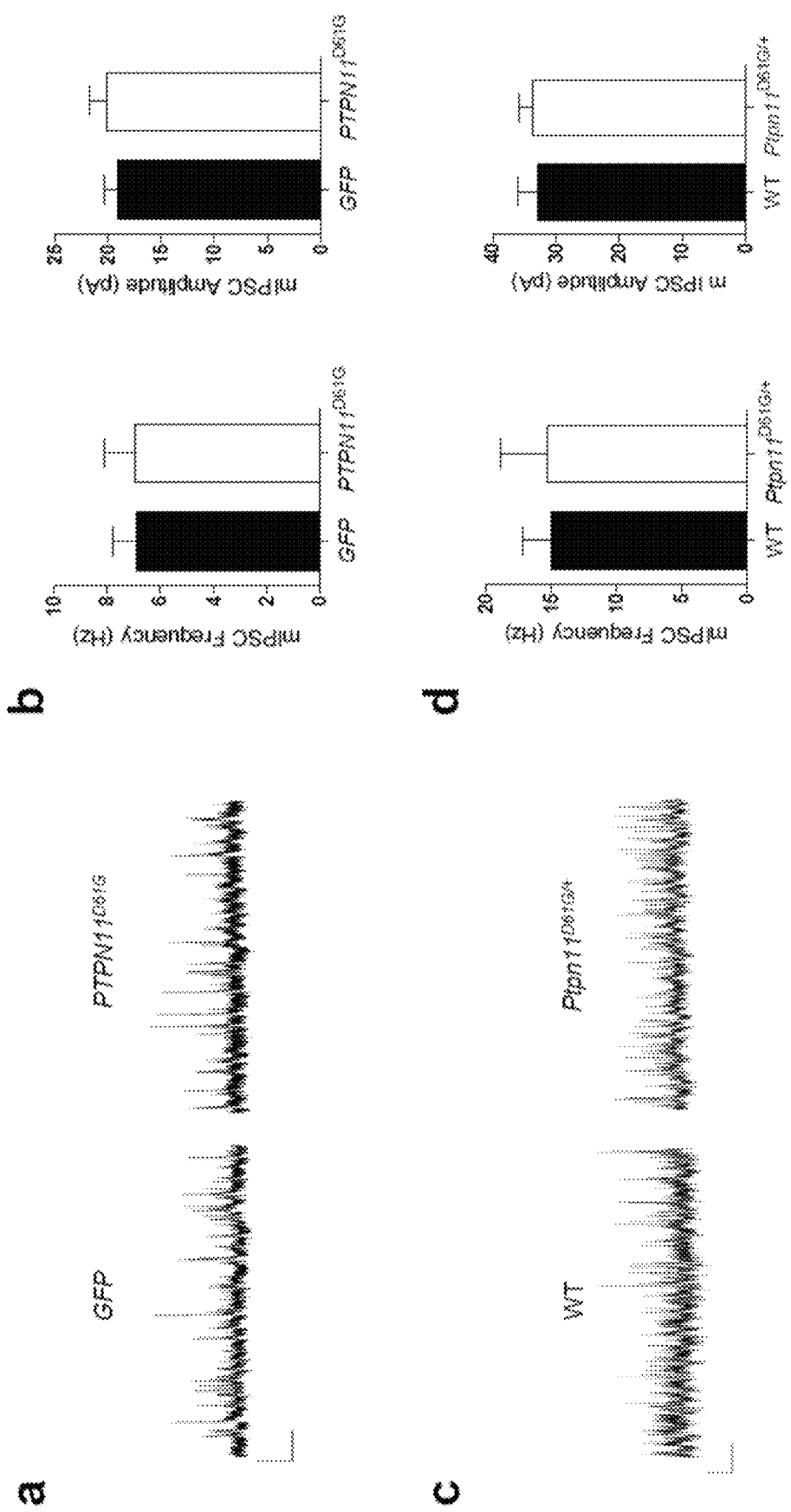

FIG. 16 show that mIPSC was not changed in either PTPN11$^{D61G}$-infected mice or Ptpn11$^{D61G/+}$ mutants. Panel a) Representative traces of mIPSC recordings from GFP or PTPN11$^{D61G}$-expressing hippocampus. Panel b) Neither frequency nor amplitude of mIPSC was differed significantly in GFP (n=9) versus PTPN11$^{D61G}$ (n=7) mice. Frequency, t-test, P=0.983; Amplitude, t-test, P=0.634. Panel c) Representative traces of mIPSC recordings from Ptpn11$^{D61G/+}$ mutant or wild type littermates. Panel d) Either frequency of amplitude of mIPSC was significantly different between wild-type and Ptpn11$^{D61G/+}$ mutant mice. Frequency: WT, 15.06±2.08 pA, n=7; Ptpn11$^{D61G/+}$,15 0.35±3.50, n=8, t-test, P=0.947. Amplitude: WT, 32.91±3.06, n=7; Ptpn11$^{D61G/+}$, 33.59±2.32, n=8, t-test, P=0.860. Scale, 20 pA and 1 s.

DETAILED DESCRIPTION OF THE INVENTION

In Noonan Syndrome (NS) 30% to 50% of subjects show cognitive deficits of unknown etiology and with no known treatment. As provided herein, knock-in mice expressing either of two NS-associated Ptpn11 mutations show hippocampal-dependent spatial learning impairments and deficits in hippocampal long-term potentiation (LTP). In addition, viral overexpression of the PTPN11$^{D61G}$ in adult hippocampus results in increased baseline excitatory synaptic function, deficits in LTP and spatial learning, which can all be reversed by a MEK inhibitor. Furthermore, brief treatment with lovastatin reduces Ras-Erk activation in the brain, and normalizes the LTP and learning deficits in adult Ptpn11$^{D61G/+}$ mice. The results herein demonstrate that increased basal Erk activity and corresponding baseline increases in excitatory synaptic function are responsible for the LTP defects and, consequently, the learning deficits in mouse models of NS. These data also suggest that lovastatin or MEK inhibitors may be useful for treating the cognitive deficits in NS.

In the present study, whether NS mutant mice have deficits in learning and memory and synaptic plasticity was first examined. Then whether increasing SHP2 activity in adult brain affects synaptic function, LTP and learning and memory was analyzed. Finally, whether the LTP and learning deficits of NS mutant mice could be rescued in adults was evaluated.

The present disclosure provides methods of treating cognitive deficits by use of inhibitors of hydroxymethylglutaryl CoA (HMG CoA) reductase. Cognitive deficits that may be treated by the methods herein include those associated with known genetic abnormalities and cognitive deficits displaying clinical symptoms similar to, and in many cases overlapping with the identified genetic causes of the cognitive dysfunction.

The compounds and compositions for use in the methods herein comprise inhibitors of the enzyme HMG-CoA reductase, which catalyzes the conversion of HMG-CoA to mevalonate, the isoprenoid intermediate used for cholesterol biosynthesis. An important class of HMG CoA inhibitor compounds is statins, which are used to treat subjects with hypercholesterolemia to decrease serum cholesterol and reduce the risk of associated diseases, such as heart disease and atherosclerosis.

Although statins are generally administered for treating hypercholesterolemia, it is shown here that subjects suffering from cognitive deficits associated with specific disorders, but who do not display abnormal cholesterol levels, may benefit in improved cognitive function that is adversely affected in the particular disorder. Dose of statins comparable to the dosage generally prescribed for hypercholesterolemia is shown to have beneficial effects, and subjects with normal cognitive function are not affected upon treatment with statins, suggesting that the statins are affecting a physiological process that is abnormal or imbalanced in the afflicted subject. Moreover, the studies herein show that statins may cross the blood-brain barrier and have therapeutic effect on neuronal cells to improve cognitive function in subjects whose blood brain barrier may not be compromised by traumatic injury, or age related diseases such as Alzheimer's or other dementias.

Treatment of Cognitive Deficits

In accordance with the above, the methods disclosed herein comprise administration of a HMG-CoA reductase inhibitor to improve, enhance, or restore the cognitive function of subjects suffering from a cognitive deficit. "Cognitive function" as used herein refers to the performance of some cognitive activity, such as memory, perception, learning, and reasoning. "Learning" refers to acquisition of information and/or knowledge, and is typically evaluated by exposing a subject to a learning experience and observing changes in behavior arising from that experience. Learning may be categorized as non-associative and associative. Non-associative learning occurs when a subject is exposed to a single stimulus in the absence of any other connected stimulus. Habituation and sensitization are two examples of non-associative learning. Associative learning occurs when a subject is exposed to a stimulus in association with another stimulus or where a stimulus is associated with the organism's behavior. Examples of associative learning are classical conditioning or operant conditioning.

"Memory" refers to the storage and retrieval of information. Memory is generally classified into short term memory (also called working memory) and long term memory, where consolidation into long term memory is believed occur through a stage involving short term memory. Short-term memory lasts for period of seconds to minutes, up to several days but which is subject to disruption and loss. Long-term memory is durable and can last for years, up to the life of the subject. As further described below, a correlate of learning and memory at the cellular level is long term potentiation (LTP), which is an increase in synaptic strength (i.e., potentiation) that occurs following a train of stimuli of an afferent neural pathway. There are different components to LTP that mimic short term and long term memory. Short-term component of LTP typically follows a single train of stimuli, is durable for minutes, and is not blocked by inhibitors of protein synthesis. Long-term component of LTP (L-LTP) can be induced by multiple trains of stimuli, may last for hours to weeks, and requires transcription and protein synthesis. Modulation of LTP is associated with activation of glutamate receptors as well as activity of inhibitory GABA receptors (Remondes, M. et al., Learn Mem. 10(4):247-52 (2003)).

Correspondingly, "cognitive disorder" refers to a disorder that affects mental processes, including impairments of memory, learning, awareness, attention, communication, motor coordination, and/or intellectual capacity. "Impairment of cognition," or "cognitive deficits" as used herein, are associated with various disorders, including among others, developmental disabilities, such as mental retardation, autism, dyslexia, attention deficit/hyperactivity disorder, ischemic stroke, traumatic brain injury, Alzheimer's Disease, degenerative dementia, obsessive compulsive disorder, schizophrenia, and Noonan Syndrome. Such disorders are often accompanied by personality and behavioral differences. However, a cognitive deficit as used herein specifically excludes impaired cognitive abilities associated with age related disorders, such as Alzheimer's and degenerative dementias. An "age related disorder" refers to a disorder in which the subject exhibits normal cognitive abilities and function for an extended time period from birth, but where cognitive function declines with passage of time. For instance Alzheimer's is considered an age related disease where the affected subject has normal cognitive abilities for much of the individual's life until onset of the disease in late stages of life. Although genetic abnormalities may contribute to a familial form of Alzheimer's disease characterized by early onset, the time period for manifestation of cognitive decline still requires about 30-50 years.

Humans with intellectual disabilities are those who develop at a below average rate and experience difficulty in learning and social adjustment. Intellectual disabilities refers to significantly sub-average general intellectual functioning existing concurrently with deficits in adaptive behavior and manifested during the developmental period that adversely affects a subject's educational performance. General intellectual functioning is typically measured by an intelligence test that is adjusted for the developmental level to which the test subject is a member.

"Subject" as used herein refers to an animal or a patient for whom is intended the described treatment. Subjects include, ayes (e.g., chickens, pigeons, owls), and mammals, including by way of example and not limitation, members of rodentia (e.g., mouse, rat, guinea pig), lagomorpha (e.g., rabbits, hares), perissodactyla (e.g., horses, donkeys, etc.), artodactyla (e.g., pigs, cows, sheep), carnivora (e.g., cats, canines), and primates (e.g., apes, monkeys, baboons, and humans). Subjects also include animals modified using recombinant DNA and/or transgenic techniques, such as animals modified to inactivate, overexpress, or misexpress genes involved or suspected of involvement in cognitive function.

In some embodiments, subject as used herein specifically excludes those within a population for whom HMG CoA reductase inhibitors are medically prescribed for higher than normal cholesterol levels, or for elevated cholesterol levels that result in adverse effects on cognitive function. A normal level of cholesterol is a level that generally does not warrant therapeutic use of HMG CoA reductase inhibitors and/or a level that does not manifest itself in a cognitive deficit in a specified class of subjects or in the general population. This level will depend on the subject and variations in cholesterol levels observed with respect to age, sex, and the population type. Generally, cholesterol levels are measured when the subject is not suffering from an acute illness, not under stress, and for a woman, when not pregnant. The level of cholesterol as used herein refers to the total serum cholesterol level, which includes the combined cholesterol found in sera in the form of high density lipoprotein (HDL), intermediate density lipoprotein (IDL), low density lipoprotein (LDL), and very low density lipoprotein (VLDL).

An exemplary normal cholesterol level for a human is that below about the 95th percentile of the general population pool, below about the 85th percentile of the general population pool, below about the 75th percentile of the general population pool, below about the 50th percentile of the general population pool to about the 25th percentile of the general population pool. Thus, in some embodiments, a normal level for a human is below about 240 mg/dL, below about 220 mg/dL, below about 200 mg/dL, below about 190 mg/dL, below about 180 mg/dL, or below about 170 mg/dL, where the lower limit of cholesterol level is that considered healthy for the subject, such as about 120 mg/dL, 140 mg/dL, or 150 mg/dL, depending on various factors, such as the age and sex of the subject. A level consider healthy for a child or adolescent is between about 120 mg/dL and about 170 mg/dL. An exemplary normal level of serum cholesterol for a human adult is a range that is below about 240 mg/dL or below about 200 mg/dL to about 140 mg/dL. Thus, in some embodiments, the population of subjects treatable using the methods herein include children, adolescents, and adults who do not have abnormally elevated cholesterol levels and who have not manifested age related cognitive disorders, as described above.

In some embodiments, the cholesterol level may be based on the amount of cholesterol in the LDL fraction. Cholesterol and triglycerides found in sera fractionate into various components: HDL, IDL, LDL, and VLDL. The LDL fraction derives from VLDL, and elevated levels of total serum cholesterol and cholesterol in the LDL (c-LDL) fraction are correlated with increased risk of atherosclerosis. In some embodiments, the normal level of c-LDL for a human is that below about the 95th percentile of the general population pool, below about the 85th percentile of the general population pool, below about the 75th percentile of the general population pool, below about the 50th percentile of the general population pool, to about the 25th percentile of the general population pool. Thus, in some embodiments, the c-LDL level is less than about 160 mg/dL, less than about 130 mg/dL, or less than about 100 mg/dL with the lower limit being a level of c-LDL that is considered a healthy level.

In addition to subjects with above-normal levels of serum cholesterol who are prescribed HMG CoA reductase inhibitors, another class of subjects for whom the treatment is not intended is those with certain defects in cholesterol biosynthesis. Defects in synthesis of intermediates prior to formation of squalene are not indicated for treatment with statins. For instance, there is a single human genetic disorder arising from a deficiency of mevalonate kinase known to affect this portion of the cholesterol biosynthetic pathway. Subjects with defects in the cholesterol biosynthetic pathway downstream of the squalene intermediate are also generally excluded, although it is to be understood that the cognitive deficits arising from such disorders, such as Smith-Lemli-Opitz syndrome, might benefit from treatment from statins.

According to the present invention, the cognitive disorders, including memory, learning, and/or cognitive deficits, that may be treated using the inhibitor compounds described herein are those associated with Noonan Syndrome.

Symptoms of Noonan Syndrome include inner ear structural abnormalities, congenital heart problems, cerebrovascular abnormalities (e.g., arteriovenous malformations), short stature, delayed puberty, delayed gastrointestinal motor development, undescended testes in boys, lymphatic abnormalities, and spinal deformity. More than about ⅓ of subjects afflicted with Noonan Syndrome exhibit cognitive disorders. Such cognitive disorders include language problems, ADHD, lower IQ, executive deficits, delayed verbal recall problems, visual recognition memory deficits, and the like. Clumsiness/motor incoordination, as well as social and emotional recognition/expression problems, are common to subjects afflicted with Noonan Syndrome. In some embodiments, the subjects to be treated according to the invention herein have been diagnosed as having Noonan Syndrome. The diagnosis may be based on clinical observations/symptoms or the result of a genetic test for Noonan Syndrome. Such diagnostic methods are known in the art.

Treating the cognitive deficits associated with Noonan Syndrome comprises administering a HMG CoA reductase inhibitor to a subject in an amount effective to improve, enhance, or restore cognitive function. As used herein, an "HMG CoA Reductase inhibitor" is any compound or composition, including prodrugs, salts, solvates and hydrates thereof, which inhibits HMG CoA reductase activity. An inhibitor includes compound that act via competitive, non-competitive, or un-competitive mechanisms, as they are commonly known in the art. One important class of HMG CoA reductase inhibitors are generally known as statins, which are prescribed to treat hyperlipidemia characterized by elevated serum cholesterol levels.

Various HMG CoA reductase inhibitors, corresponding prodrugs, salts, solvates and hydrates, are known in the art and may be used for the methods herein. Atorvastatin and derivatives thereof are described in U.S. Pat. No. 5,273,995 and EP 409281 and are available commercially under the tradenames Lipitor®, Sortis®, Torvast®, Totalip®, and Xarator®. Cerivastatin and derivatives thereof are described in U.S. Pat. Nos. 5,006,530; 5,177,080, and EP 325130 and are available under the tradenames Rivastatin®, Baycol®, and Lipobay®. Although the levels of cerivastatin prescribed for hyperlipidemia has resulted in toxic side effects, lower non-toxic levels may be appropriate for treatment of cognitive deficits.

Another of these statin compounds is clofibrate and derivatives thereof, as described in U.S. Pat. No. 3,262,850 and GB 860303. Clofibrate is available under the tradenames Amotril®, Anparton®, Apolan®, Artevil®, Claripex®, Liprinal®, Normet®, Regelen®, Serotinex®, and Xyduril®. Inhibitor colestipol and derivatives thereof are described in U.S. Pat. Nos. 3,692,895 and 3,803,237 and published patents DE 1927336, and DE 2053585. Fluvastatin and derivatives thereof are described in U.S. Pat. No. 4,739,073 and WO 84/02131 and are available under the tradenames Fluindostatin®, XU 62-320, Lescol®, Lipaxan® and Primexin®. Gemfibrozil and derivatives thereof are described in U.S. Pat. Nos. 3,674,836 and 4,126,637, and published patent DEL 1925423, and are available under the tradenames Decrelip®, Genlip®, Gevilon®, Lipozid®, and Lopid®. Lovastatin and derivatives thereof are described in U.S. Pat. No. 4,231,938 and are available under the tradenames Altocar®, Lovalip®, Mevacor®, Mevinacor®, Nevlor®, and Sivlor®. Pitavastatin and derivatives thereof are described in EP65835 and U.S. Pat. No. 6,162,798 and are available under the tradenames Itabastatin®, Livalo®, NisvastatinO, Itavastatin®, and Zomaril®. Pravastatin and derivatives thereof are described in U.S. Pat. No. 4,346,227 and published patent DE 3122499, and are available under the tradenames Elisor®, Lipostat®, Liprevil®, Mevalotin®, Oliprevin®, Pravachol®, Pravasin®, Selectin®, and Vasten®. Rosuvastatin and derivatives thereof are described in U.S. Pat. Nos. 5,128,366, 6,589,959, and published application WO 521471, and are available under the tradename Crestor®. Simvastatin and derivatives thereof are described in U.S. Pat. No. 4,444,784 and EP 33538 and are available under the tradenames Denan®, Liponorm®, Simovil®, Sinvacor®, Sivastin®, Zocor®, and Zocord®.

It is to be understood that while a single inhibitor is typically prescribed to lower elevated cholesterol levels, mixtures of HMG CoA reductase inhibitors may be used for the uses described herein. Compatible mixtures may be made to enhance the efficacy and/or lower the toxicity of the inhibitors in treating the cognitive disorders.

In some embodiments, other compounds targeting the cholesterol biosynthetic pathway may be used to treat the cognitive deficit. Thus, in some embodiments, the compound is a modulator of farnesyl transferase, such as an inhibitor of farensyl transferase activity. As used herein, a farnesyl transferase inhibitor is an inhibitor of the enzyme responsible for transfer of farnesyl pyrophosphate onto protein substrates. Suitable farnesyl transferase inhibitors include, by way of example and not limitation, FTI-276 (Calbiochem, San Diego, Calif., USA); SCH66336 (Schering-Plough, (Kenilworth, N.J., USA); (B)-6-[amino(4-chlorophenyl)(1-methyl-1H-imidazol-5-yl)methyl]-4-(3-chlorophenyl)-1-methyl-2(1H)-quinolinone (also known as R115777, tipifarnib, and Zarnestra) (Johnson & Johnson); L-778,123; and FTI-2148.

In some embodiments, the other compound may be a modulator of geranylgeranyl transferase activity, such as an inhibitor of geranylgeranyl transferase. These compounds may be suitable for cognitive disorders that are associated with dysregulation of Rac or Rho activity since these proteins are modified by attachment of geranylgeranyl groups. Suitable geranylgeranyl transferase inhibitors include, by way of example and not limitation, GGTI-286 (Calbiochem, San Diego, Calif., USA); GGTI-297; GGTI-2154; and GGTI-2166. Compounds with inhibitory activities to both farnesyl transferase and geranylgeranyl transferases are described in Tucker T. J. et al, Bioorg. Med. Chem. Lett. 12(15):2027-30 (2002)).

In some embodiments, the compounds that inhibit inhibitory neuronal activity may be used. A number of different aspects of inhibitory neuronal activity may be targeted, including, among others, transport of inhibitory neurotransmitters into synaptic vesicles, degradation of the inhibitory neurotransmitter, receptors that are activated by binding to inhibitory neurotransmitters, and channel proteins that decrease the generation of action potentials.

In some embodiments, the inhibitors inhibit GABA mediated inhibition, and thus are inhibitors of GABA receptor activity. An "inhibitor of GABA receptor" as used herein refers to a compound that binds to but does not activate GABA receptors (i.e., antagonists), thereby blocking the actions of endogenous GABA and GABA agonists. Also encompassed within "inhibitor of GABA receptor" is an inverse agonist, which binds to a region of the GABA receptor different from the region that interacts with GABA but which results in inhibition of GABA or GABA agonist binding. Useful inhibitors may have general activity against various forms of GABA receptors, or are selective for different GABA receptor types. Compatible mixtures of selective GABA receptor inhibitors may be used to generate a general inhibitor of GABA receptor activity.

Accordingly, in some embodiments, the inhibitor used is selective for $GABA_A$. Exemplary embodiments of antagonist compounds selective for $GABA_A$ receptor include, by way of example and not limitation, picrotoxin; hydrastine; securinine; 6-(5,6,7,8-tetrahydro-6-methyl-1,3-dioxolo[4,5-g]isoquinolin-5-yl)furo[3,4-e]-1,3-benzodioxol-8(6H)-one (i.e., bicuculline); 6-Imino-3-(4-methoxyphenyl)-1(6H)-pyridazinebutanoic acid hydrobromide (i.e., gabazine); 4-(2-naphthylmethyl)-5-(4-piperidyl)-3-isoxazolol and analogs thereof (Frolund, B. et al., J. Med. Chem. 48(2):427-39 (2005)); β-carboline-3-carboxylate-t-butyl ester (Rowlett J, et al., CNS Spectr. 10(1):40-8 (2005). $GABA_A$ inverse agonists include the naturally occurring peptide Diazepam Binding Inhibitor (DBI); methyl-6,7-dimethoxy-4-ethyl-beta-carboline-3-carboxylate (DMCM); ethyl-beta-carboline-3-carboxylate (beta-CCE), N-methyl-beta-carboline-3-carboxamide (FG 7142); ethyl-8-azido-5,6-dihydro-5-methyl-6-oxo-4H-imidazo[1,5 alpha][1,4]-benzodiazepine-3-carboxylate (Ro 15-4513); (3-tert-Butyl-7-(5-methylisoxazol-3-yl)-2-(1-methyl-1H-1,2,4-triazol-5-ylmethoxy)pyrazolo[1,5-d][1,2,4]triazine; and 2-methoxy-3,8,9-trihydroxy coumestan (PCALC36). Other $GABA_A$ antagonists and inverse agonists applicable to the uses herein will be apparent to the skilled artisan.

In some embodiments, the inhibitor used is selective for the $GABA_B$ receptor. Some exemplary embodiments of antagonist compounds selective for receptor $GABA_B$ include by way of example and not limitation, 3-Amino-2-(4-chlorophenyl)propylphosphonic acid (i.e., phaclofen); 3-amino-2-(4-chlorophenyl)propylsulfonic acid (i.e., saclofen); 3-amino-2-(4-chlorophenyl)-2-hydroxypropylsulfonic acid (i.e., 2-hydroxysaclofen); 3-aminopropyl-diethoxymethylphosphinic acid (CGP 35348); 3-[[(3,4-dichlorophenyl)methyl]amino]propyl]diethoxymethyl)phosphinic acid (CGP 52432); (2S)-3-[[(1S)-1-(3,4-dichlorophenyl) ethyl]amino-2-hydroxypropyl](phenylmethyl)phosphinic acid (CGP 55845); 3-[[1-(S)-(3,4dichlorophenyl)ethyl] amino]-2-(S)-hydroxy-propyl]-cyclohexylmethyl phosplinic acid (CGP 54626); (3-aminopropyl)(cyclohexylmethyl)phosphinic acid (CGP 46381); and (2S)-(+)-5,5-dimethyl-2-morpholineacetic acid (SCH 50911). Other $GABA_B$ receptor inhibitors will be apparent to the skilled artisan.

In some embodiments, the inhibitors of HMG CoA reductase, farnesyl transferase inhibitors, and geranylgeranyl transferase, and inhibitors of inhibitory neuronal activity, (collectively referred to as "inhibitor compounds") may be used in combination to treat the cognitive disorder or modulate LTP. Combinations include a HMG CoA reductase inhibitor and a farnesyl transferase inhibitor, a HMG CoA reductase inhibitor and a geranylgeranyl transferase inhibitor, a farnesyl and geranylgeranyl transferase inhibitor, a HMG CoA reductase inhibitor in combination with farnesyl and geranylgeranyl tranferase inhibitors, or a HMG CoA reductase inhibitor in combination with an inhibitor of inhibitory neuronal activity. Other combinations will be apparent to the skilled artisan. While the combinations may be used generally for the cognitive disorders effectively treated by HMG CoA reductase inhibitors alone, some disorders may be treated with a specific combination where the molecular basis underlying the disorders is suggested as a farnesylated protein (e.g., RAS), a geranylgeranlylated protein (e.g., Rho or Rac), or a GABA receptor activity. For instance, learning disorders associated with NF-I may be treated with a combination of HMG CoA reductase inhibitor and a farnesyl transferase inhibitor or a HMG CoA reductase inhibitor and a $GABA_A$ receptor inhibitor.

The inhibitor compounds may be administered in the form of a composition. In some embodiments the inhibitor combinations are administered adjunctively, by the same route or by a different route. Adjunctive administration includes simultaneous or sequential administration of the inhibitor compounds.

The amounts of the inhibitor compounds to be administered will be determined empirically in accordance with conventional procedures. Generally, for administering the inhibitor compounds, the subject formulations are given at an effective amount. An "effective amount", "effective dose", "pharmacologically effective amount", or "pharmacologically effective dose" is an amount sufficient to produce the desired physiological effect or an amount capable of achieving the desired result, particularly for treating the disorder or condition, including reducing or eliminating one or more symptoms of the disorder or disease. Thus the compounds and compositions described herein may be administered therapeutically to achieve a therapeutic benefit or prophylactically to achieve a prophylactic benefit. By therapeutic benefit is meant eradication or ameliorating of the underlying disorder being treated, and/or eradication or amelioration of one or more of the symptoms associated with the underlying disorder such that the patient reports an improvement in cognitive function, notwithstanding that the patient may still be affected with the underlying disorder.

In the case of cognitive disorders, administration of the compounds and compositions to a patient suffering from the cognitive deficit provides a therapeutic benefit when there is improvement, enhancement, or restoration in the cognitive function. The compounds and compositions may also be administered prophylactically to a patient at risk of being afflicted with the cognitive disorder. For instance, these include individuals who have been diagnosed with an inherited disorder that has an associated disruption of normal cognitive function such that therapy may be initiated by early diagnosis (e.g., infancy).

A therapeutically effective dose of the inhibitor compounds is readily determined by methods well known in the art. Factors to consider in determining an appropriate dose include, but are not limited to, size and weight of the subject, the age and sex of the subject, the type of cognitive disorder, the severity of the cognitive disorder, method of delivery of the compounds and compositions, and half-life and efficacy of the inhibitor compounds.

An initial effective dose can be estimated initially from cell culture assays. For example, because the hippocampus is a model system for learning and memory, in vitro culture systems using hippocampal slices or cultures may be suitable for initial determination of an effective dose. The cells may be contacted with the inhibitor compounds and in the absence of inhibitor to determine the levels of drug useful for enhancing the cellular correlates of neural processes associated with cognitive function, such as LTP.

Following in vitro studies, a dose can then be formulated in experimental animal models to generate data on circulating concentration or tissue concentration, including that of the $IC_{50}$ (i.e., concentration sufficient to affect 50% of the activity being targeted or measured) as initially determined by the in vitro culture assays. Suitable experimental animals include, but are not limited to mouse, rat, guinea pigs, rabbits, pigs, monkeys, and chimpanzees. As with the in vitro studies, initial determination is made of an effective dose of the inhibitor compound (e.g., Cmax) and the corresponding pharmacokinetic profile. Useful in this regard are numerous identified animal model systems (e.g., pure bred animal lines) with associated cognitive disorder or transgenic (e.g., knockout) animals that mimic or approximate the genetic disorders that display the cognitive deficit. Behavioral tests can be conducted on these animal systems to determine an effective dose.

In accordance with the above, the dosages of the HMG CoA reductase inhibitors may be the standard dosages administered to treat hypercholesterolemia (i.e., an amount sufficient to lower serum cholesterol levels in a subject with hypercholesterolemia). Thus, an amount of inhibitor compound is used to lower the cholesterol level to those observed on or below the 95th percentile, on or below the 85th percentile, on or below the 75th percentile, on or below the 50th percentile of the subject population, to about 25th percentile of the subject population. In some embodiments, the amount of inhibitor compound is administered to lower the cholesterol level below about 240 mg/dL, below about 220 mg/dL, below about 200 mg/dL, below about 190 mg/dL, below about 180 mg/dL, or below about 170 mg/dL.

In some embodiments, an amount of HMG CoA reductase inhibitor is administered to lower the c-LDL levels to that below about the 95th percentile of the general population pool, below about the 85th percentile of the general population pool, below about the 75th percentile of the general population, below about the 50th percentile of the general population, to about the 25th percentile of the general population pool. Thus, in some embodiments, an amount of HMG CoA reductase inhibitor is administered to lower the c-LDL in a human subject to less than about 160 mg/dL, to less than about 130 mg/dL, to less than about 100 mg/dL, to less than about 70 mg/dL, with the lower limit being a level of LDL considered healthy, which may range from 40 mg/dL or 50 mg/dL for the human population.

Exemplary dosages for use of atorvastatin (Lipitor®) in the treatment of hypercholesterolemia are from about 10 mg to about 80 mg per day. For subjects of 45 to 100 kg body weight, this dosage corresponds to about 0.1 mg/kg/day to about 1.8 mg/kg/day. The recommended dosages of lovastatin (Mevacor®) is from about 10 mg to about 80 mg/day in one or two dosages, or about 0.1 mg/kg/day to about 1.8 mg/kg/day. The recommended dosage of rosuvastatin (Crestor®) is from about 5 mg to about 40 mg/day, or about 0.05 mg/kg/day to about 0.9/mg/kg/day. The recommended dosage for pravastatin (Pravachol®) is from about 10 mg to about 80 mg/day as a single dose, or about 0.1 mg/kg/day to about 1.0 mg/kg/day. The recommended dosage for simvastatin (Zocor®) is from about 5 mg to about 80 mg/day taken once per day, or about 0.05 mg/kg/day to about 1.8 mg/kg/day. Determining corresponding dosages for other HMG CoA reductase inhibitors are well within the skill of those in the art.

In some embodiments, dosages are lower than those prescribed to treat hypercholesterolemia or are dosages that do not result in significant lowering of serum cholesterol levels in the treated subject but which are effective in treatment of the cognitive deficit. These dosages are referred herein as "low dosages." In some embodiments, a significant lowering of cholesterol level is a change of about 5 percentile, 10 percentile, 15 percentile, 20 percentile, 30 percentile, 40 percentile of the cholesterol level in the general population. In some embodiments, a significant lowering of cholesterol level is change in serum or LDL cholesterol level of 20 mg/dL, 30 mg/dL, 50 mg/dL, 75 mg/dL or more. For atorvastatin or lovastatin, this may correspond to a dosage of from about 0.1 mg/kg/day to about 0.01 mg/kg/day or lower. For rosuvastatin and simvastatin, the lower dosage may correspond to a dosage of from about 0.05 mg/kg/day to about 0.005 mg/kg/day. Determining low dosages of all of the HMG CoA reductase inhibitors are well within the skill of those in the art.

The inhibitor compounds may be provided as various pharmaceutical compositions formulated in pharmaceutical compositions per se, or in the form of a hydrate, solvate, or pharmaceutically suitable salts thereof or with a suitable excipient. Accordingly, in one embodiment, the pharmaceutical compositions comprise a pharmaceutically acceptable carrier or vehicle and a pharmacologically effective amount of the inhibitor compound.

As described above, pharmaceutically acceptable salts are intended to include any art recognized pharmaceutically acceptable salt of the compound or inhibitor which is made with counter-ions understood in the art to be generally acceptable for pharmaceutical uses and which possesses the desired pharmacological activity of the parent compound. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, pharmaceutically acceptable vehicle or pharmaceutically acceptable carrier comprise any of standard pharmaceutically accepted carriers used by those skilled in the art for administering a pharmaceutical composition. Thus, the inhibitor compounds may be prepared as formulations in pharmaceutically acceptable excipients suitable for any mode of administration that include, but are not limited to, oral, topical, transdermal, cutaneous, subcutaneous, intravenous, intraperitoneal, intramuscular, nasal, transdermal, vaginal, buccal, and rectal (e.g., colonic administration) delivery. Choosing the appropriate route of administration is well within the skill of the art.

For oral administration, the pharmaceutical compositions may be prepared with pharmaceutically acceptable excipients such as binding agents (e.g., starch, carboxymethyl cellulose, hydroxylpropyl methyl cellulose), fillers (e.g., lactose, microcrystalline cellulose, calcium phosphate, etc.), lubricants (e.g., magnesium stearate, talc, silicon dioxide, etc.); disintegrants (potato starch and sodium starch glycolate); or wetting agents (e.g., sodium lauryl sulfate). Formulations for oral administrations may take various forms, including, but not limited to, tablets, capsules, lozenges, powders, etc. Pills, tablets, or capsules may have an enteric coating that remains intact in the stomach but dissolves in the intestine. Various enteric coatings are known in the art, a number of which are commercially available, including, but not limited to, methacrylic acid-methacrylic acid ester copolymers, polymer cellulose ether, cellulose acetate phathalate, polyvinyl acetate phthalate, hydroxypropyl methyl cellulose phthalate, and the like.

The inhibitors compounds may be in liquid form prepared in diluents for administration orally or by injection. These diluents include, by way of example and not limitation, saline, phosphate buffer saline (PBS), aqueous ethanol, or solutions of glucose, mannitol, dextran, propylene glycol, polyethylene glycol (e.g., PEG400), and mixtures thereof. Suitable diluents also include non-aqueous vehicles, including oils and other lipophilic solvents, such as various vegetable oils, animal oils, and synthetic oils (e.g., peanut oil, sesame oil, olive oil, corn oil, safflower oil, soybean oil, etc.); fatty acid esters, including oleates, triglycerides, etc.; cholesterol derivatives, including cholesterol oleate, cholesterol linoleate, cholesterol myristilate, etc.; liposomes; and the like. The compositions for injection may be prepared directly in a lipophilic solvent or preferably, as emulsions (see, e.g., Liu, F. et al., Pharm. Res. 12: 1060-1064 (1995); Prankerd, R. J. J., Parent. Sci. Tech. 44: 139-49 (1990); and U.S. Pat. No. 5,651,991). The formulations for injection may be presented in unit dosage form, e.g., in ampules or in multidose containers. The diluents may also contain suspending agents (e.g., soribitol solution, cellulose derivatives, or hydrogenated edible fats) and emulsifying agents (e.g., lecithin or acacia).

Formulations for rectal or vaginal administration may be in the form of salves, tinctures, crèmes, suppositories, enemas, or foams. Suppositories for rectal application may contain conventional suppository bases such as cocoa butter, carbowaxes, polyethylene glycols, or glycerides, which are solid or semi-solid at room temperature but liquid at body temperature.

Additionally, the pharmaceutical compositions may include bactericidal agents, stabilizers, buffers, emulsifiers, preservatives, flavoring, sweetening agents, and the like as needed or desired in the various formulations.

The pharmaceutical compositions comprising the inhibitor compounds may be manufactured in a manner well known to the skilled artisan, such as by conventional means of mixing, dissolving, granulating, levigating, emulsifying, encapsulating, entrapping, or lyophilization processes. Suitable pharmaceutical formulations and methods for preparing such compositions may be found in various standard references, such as Remington's Pharmaceutical Sciences, 17th edition, Mack Publishing Co., Philadelphia, Pa. (1985) and Handbook of Pharmaceutical Excipients, 3rd Ed, Kibbe, A. H. ed., Washington D.C., American Pharmaceutical Association (2000); hereby incorporated by reference in their entirety.

Additionally, the inhibitors, either separately or as a combination, may also be introduced or encapsulated into the lumen of liposomes for delivery and for extending lifetime of the compounds. As known in the art, liposomes can be categorized into various types: multilamellar (MLV), stable plurilamellar (SPLV), small unilamellar (SUV), or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids (see, e.g., U.S. Pat. No. 5,833,948).

Cationic lipids are also suitable for forming liposomes. Generally, the cationic lipids have a net positive charge and have a lipophilic portion, such as a sterol or an acyl or diacyl side chain. Preferably, the head group is positively charged. Typical cationic lipids include 1,2-dioleyloxy-3-(trimethylamino)propane; N-[1-(2,3-ditetradecycloxy)propyl]-N,N-dimethyl-N—N-hydroxyethylammonium bromide; N-[1-(2,3-dioleyloxy)propyl]-N,N-dimethyl-N-hydroxy ethylammonium bromide; N-[1-(2,3-dioleyloxy)propyl]-N,N,N-trimethylammonium chloride; 3-[N—(N',N'-dimethylaminoethane) carbamoyl] cholesterol; and dimethyldioctadecylammonium.

Of particular interest are fusogenic liposomes, which are characterized by their ability to fuse with a cell membrane upon appropriate change in physiological condition or by presence of fusogenic component, particularly a fusogenic peptide or protein. In one aspect, the fusogenic liposomes are pH and temperature sensitive in that fusion with a cell membrane is affected by change in temperature and/or pH (see for example, U.S. Pat. Nos. 4,789,633 and 4,873,089). Generally, pH sensitive liposomes are acid sensitive. Thus, fusion is enhanced in physiological environments where the pH is mildly acidic, for example the environment of a lysosome or endosome. This property allows direct release of the liposome contents into the intracellular environment following endocytosis of liposomes (Mizoue, T., Int. J. Pharm. 237: 129-137 (2002)).

Another form of fusogenic liposomes comprises liposomes that contain a fusion-enhancing agent. When incorporated into the liposome or attached to the lipids, the agents enhance fusion of the liposome with other cellular membranes, thus resulting in delivery of the liposome contents into the cell. The agents may be fusion enhancing peptides or proteins, including hemaggulutinin HA2 of influenza virus (Schoen, P., Gene Ther. 6: 823-832 (1999)); Sendai virus envelope glycoproteins (Mizuguchi, H., Biochem. Biophys. Res. Commun 218: 402-407 (1996)); vesicular stomatitis virus envelope glycoproteins (VSV-G) glycoprotein (Abe, A. et al., J. Virol. 72: 6159-63 (1998)); peptide segments or mimics of fusion enhancing proteins; and synthetic fusion enhancing peptides (e.g., Kono, K. et al., Biochim. Biophys. Acta. 1164: 81-90 (1993); Pecheur, E. I., Biochemistry 37: 2361-71 (1998); and U.S. Pat. No. 6,372,720).

Liposomes also include vesicles derivatized with a hydrophilic polymer, as provided in U.S. Pat. Nos. 5,013,556 and 5,395,619, hereby incorporated by reference, (see also, Kono, K. et al., J. Controlled Release 68: 225-35 (2000); Zalipsky, S. et al., Bioconjug. Chem. 6: 705-708 (1995)) to extend the circulation lifetime in vivo. Hydrophilic polymers for coating or derivation of the liposomes include polyethylene glycol, polyvinylpyrrolidone, polyvinylmethyl ether, polyaspartamide, hydroxymethyl cellulose, hydroxyethyl cellulose, and the like. In addition, as described above, attaching proteins that bind a cell surface protein which is endocytosed, e.g., capsid proteins or fragments thereof tropic for a particular cell types and antibodies for cell surface proteins which undergo internalization (see Wu et al, supra; Wagner et al., supra), may be used for targeting and/or facilitating uptake of the liposomes to specific cells or tissues.

Liposomes are prepared by ways well known in the art (see, e.g., Szoka, F. et al., Ann. Rev. Biophys. Bioeng. 9: 467-508 (1980)). One typical method is the lipid film hydration technique in which lipid components are mixed in an organic solvent followed by evaporation of the solvent to generate a lipid film. Hydration of the film in aqueous buffer solution, preferably containing the subject compounds and compositions, results in an emulsion, which is sonicated or extruded to reduce the size and polydispersity. Other methods include reverse-phase evaporation (see, e.g., Pidgeon, C. et al., Biochemistry 26: 17-29 (1987); Duzgunes, N. et al., Biochim. Biophys. Acta. 732: 289-99 (1983)), freezing and thawing of phospholipid mixtures, and ether infusion.

In some embodiments, the carriers are in the form of microparticles, microcapsules, microspheres and nanoparticles, which may be biodegradable or non-biodegradable (see, e.g., Microencapsulates: Methods and Industrial Applications, Drugs and Pharmaceutical Sciences, Vol 73, Benita, S. ed, Marcel Dekker Inc., New York, (1996); incorporated herein by reference). As used herein, microparticles, microspheres, microcapsules and nanoparticles mean a particle, which is typically a solid, containing the substance to be delivered. The substance is within the core of the particle or attached to the particle's polymer network. Generally, the difference between microparticles (or microcapsules or microspheres) and nanoparticles is one of size. Typically, microparticles have a particle size range of about 1 to about >1000 microns. Nanoparticles have a particle size range of about 10 to about 1000 nm.

A variety of materials are useful for making microparticles containing the inhibitor compound. Non-biodegradable microcapsules and microparticles include, but not limited to, those made of polysulfones, poly(acrylonitrile-co-vinyl chloride), ethylene-vinyl acetate, hydroxyethylmethacrylate-methyl-methacrylate copolymers. These are useful for implantation purposes where the encapsulated compound diffuses out from the capsules. In another aspect, the microcapsules and microparticles are based on biodegradable polymers, preferably those that display low toxicity and are well tolerated by the immune system. These include protein based microcapsulates and microparticles made from fibrin, casein, serum albumin, collagen, gelatin, lecithin, chitosan, alginate or poly-amino acids such as poly-lysine. Biodegradable synthetic polymers for encapsulating may comprise polymers such as polylactide (PLA), polyglycolide (PGA), poly(lactide-co-glycolide) (PLGA), poly(caprolactone), polydioxanone trimethylene carbonate, polyhybroxyalkonates (e.g., poly(b-hydroxybutyrate)), poly(g-ethyl glutamate), poly(DTH iminocarbony (bisphenol A iminocarbonate), poly (ortho ester), and polycyanoacrylate. Various methods for making microparticles containing the subject compounds are well known in the art, including solvent removal process (see for example, U.S. Pat. No. 4,389,330); emulsification and evaporation (Maysinger, D. et al., Exp. Neuro. 141: 47-56 (1996); Jeffrey, H. et al., Pharm. Res. 10: 362-68 (1993)), spray drying, and extrusion methods.

Another type of carrier is nanoparticles. Submicron and nanoparticles are generally made from amphiphilic diblock, triblock, or multiblock copolymers, as is known in the art. Polymers useful in forming nanoparticles include, but are not limited to, poly(lactic acid) (PLA; Zambaux et al., J. Control Release 60: 179-188 (1999)), poly(lactide-co-glycolide), blends of poly(lactide-co-glycolide) and polycarprolactone, diblock polymer poly(l-leucine-block-1-glutamate), diblock and triblock poly(lactic acid) (PLA) and poly(ethylene oxide) (PEO) (De Jaeghere, F. et al., Pharm. Dev. Technol. 5: 473-83 (2000)), acrylates, arylamides, polystyrene, and the like. As described for microparticles, nanoparticles may be non-biodegradable or biodegradable. In addition, nanoparticles may be made from poly(alkylcyanoacrylate), for example poly(butylcyanoacrylate), in which the compound to be delivered is absorbed onto the nanoparticles and coated with surfactants (e.g., polysorbate 80). Methods for making nanoparticles are similar to those for making microparticles and include, by way of example and not limitation, emulsion polymerization in continuous aqueous phase, emulsification-evaporation, solvent displacement, and emulsification-diffusion techniques (see, e.g., Kreuter, J., Nano-particle Preparation and Applications, In Microcapsules and nanoparticles in medicine and pharmacy, M. Donbrow, ed., pg. 125-148, CRC Press, Boca Rotan, Fla., 1991; incorporated herein by reference).

Hydrogels are also useful in delivering the subject agents into a host. Generally, hydrogels are crosslinked, hydrophilic polymer networks permeable to a wide variety of drug compounds. Hydrogels have the advantage of selective trigger of polymer swelling, which results in controlled release of the entrapped drug compound. Depending on the composition of the polymer network, swelling and subsequent release may be triggered by a variety of stimuli, including pH, ionic strength, thermal, electrical, ultrasound, and enzyme activities. Non-limiting examples of polymers useful in hydrogel compositions include, among others, those formed from polymers of poly(lactide-co-glycolide), poly(N-isopropylacrylamide); poly(methacrylic acid-g-polyethylene glycol); polyacrylic acid and poly(oxypropylene-co-oxyethylene) glycol; and natural compounds such as chrondroitan sulfate, chitosan, gelatin, or mixtures of synthetic and natural polymers, for example chitosan-poly(ethylene oxide). The polymers are crosslinked reversibly or irreversibly to form gels embedded with the inhibitor compound, or pharmaceutical compositions thereof (see, e.g., U.S. Pat. Nos. 6,451,346; 6,410,645; 6,432,440; 6,395,299; 6,361,797; 6,333,194; 6,297,337 Johnson, O. et al., Nature Med. 2: 795 (1996); incorporated by reference in their entirety).

Another pharmaceutical compositions may include those in the form of transdermal patches for delivery of the compounds through the skin by diffusion or electrically mediated transport (see, e.g., Banga, A. K. et al., Int J Pharm. 179(1):1-19 (1999); U.S. Pat. Nos. 5,460,821, 5,645,854, 5,853,751, 6,635,274, 6,564,093; all publications incorporated herein by reference.).

In some embodiments, the inhibitors may be provided as a depot, such as a slow release composition comprising particles, a polymer matrix (e.g., a collagen matrix, carbomer, etc.) that maintains release of compounds over an extended period of time, use of a pump which continuously infuses the inhibitor compounds over an extended period of time with a substantially continuous rate, and the like. These and other combinations of administering effective dosages will be apparent to those skilled in the art.

The inhibitor compounds may be provided in the form of a kit or packaged formulation. A kit or packaged formulation as used herein includes one or more dosages of an HMG CoA reductase inhibitor, or salts, solvates or hydrates thereof in a container holding the dosages together with instructions for administration to a host. For example, the package may contain the HMG CoA reductase inhibitors along with a pharmaceutical carrier combined in the form of a powder for mixing in an aqueous solution, which can be ingested by the afflicted subject. Another example of packaged drug is a preloaded pressure syringe, so that the compositions may be delivered intravenously or intramuscularly. The package or kit includes appropriate instructions, which encompasses diagrams, recordings (e.g., audio, video, compact disc), and computer programs providing directions for use of the combination therapy.

Methods of Measuring Cognitive Function

To determine whether a subject is afflicted with a cognitive deficit and/or to determine improvement or restoration of cognitive function, a variety of tests may be employed for both animal model systems and for assessing individual patients. These include tests ranging from assessments of general cognitive ability to measurement of specific physiological processes associated with cognitive function.

The global examination of cognitive deficits may employ those commonly used for diagnosing such disorders as described in various reference works, such as Diagnostic and Statistical Manual of Mental Disorders, 4th Ed., American Psychiatric Association; (2000) (acronym DSM) and the International Classification of Disease (ICD), 10th Revision, World Health Organization (WHO) (2003). The DSM provides a basis for selecting the disorder from a classification that best reflects the signs and symptoms displayed by the individual being evaluated (diagnostic classification); a set of diagnostic criteria that indicates what symptoms must be present (and for how long) in order to qualify for a diagnosis (i.e., inclusion criteria) as well as those symptoms that must not be present (i.e., exclusion criteria) in order for an individual to qualify for a particular diagnosis (diagnostic criteria sets); and a description of each disorder that includes diagnostic features, subtypes of the disorder, culture, age, and gender features, prevalence, course of the disorder, hereditary pattern, and differential diagnosis. For instance, in an exemplary embodiment for diagnosing ADHD, the DSM indicates a diagnosis when the subject suffers from 6 or more symptoms of inattention that persists for more than 6 months that is maladaptive and inconsistent with the developmental level, and/or 6 or more symptoms of hyperactivity-impulsivity that has persisted for more than 6 months that is maladaptive or inconsistent with the developmental level.

The ICD is a more general reference work for all diseases and includes classifications diseases and other health problems recorded on many types of health and vital records, including death certificates and hospital records. ICD provides descriptions of mental and behavioral disorders (Chapter V); diseases of the nervous system (Chapter IV); congenital malformations, and chromosomal abnormalities (Chapter XVII). The DSM and ICD systems provide a set of standard criteria for effectively and reliably diagnosing a broad range of cognitive disorders.

Exemplary tests for cognitive function may use any number of procedures used in the art. In some embodiments, the analysis of cognitive function may use that described in Roid, G., Stanford-Binet Intelligence Scale, 5th Ed., Riverside Publishing, which is a standardized test that assesses intelligence and cognitive abilities in children and adults, generally of ages of about 2-85+ years. The test measures four areas that include verbal reasoning, quantitative reasoning, visual-spatial processing, and working memory.

These areas are covered by subtests for measuring vocabulary, comprehension, verbal absurdities, pattern analysis, matrices, paper folding and cutting, copying, quantitative, number series, equation building, memory for sentences, memory for digits, memory for objects, and bead memory. The tests identify a distinct hierarchy of abilities from normal to affected patients.

In some embodiments, the test for cognitive function may use the Mini-Mental State Exam (MMSE) and variations thereof (Folstein, M. F. et al., J. Psych. Res. 12:189-198 (1975)). MMSE is a test of cognitive status that typically takes between 5 and 10 minutes to administer. Areas measured on the MMSE include orientation to time and place, immediate and delayed verbal recall memory, attention, concentration, naming, repetition, following a 3-step command, following a written command, sentence writing, and visual-motor copying. Performance on each of the tasks is numerically graded with a maximum score of 30, with scores lower than 23 being considered indicative of cognitive impairment. The MMSE may be used to identify patients with cognitive disturbance from those without such disturbance and is also applicable to measuring the changes in cognitive state upon treatment. This test as well as others described herein and known in the art may be used in combination with other tests to substantiate or correlate the results.

In some embodiments, the test for cognitive function is the Wechsler Intelligence Scale for Children or Adults. The test for adults has two sections, a verbal and a performance measurement. The verbal section has a general knowledge test, a digit span test in which subjects are given sets of digits to repeat initially forwards then backwards (auditory recall and short term memory), a vocabulary test to measure expressive word knowledge, an arithmetic tests that measures distractibility as well as numerical reasoning, a comprehension test that focuses on issues of social awareness, and a similarities test for measuring concept formation that asks subjects to specify how two seemingly dissimilar items might in fact be similar. The performance section involves picture completion test (small pictures that all have one vital detail missing) that measures attention to detail, picture arrangement test where the subject is required to arrange them into a logical sequence, a block design test that involves putting sets of blocks together to match pattern on cards, digit symbol test that involves copying a coding pattern, and object assembly test that involves solving jig-saw type puzzles. The scores on both sections are processed to arrive at a numerical intelligence quotient (IQ).

The Wechsler Intelligence Scale for Children is similar to the adult test, having a verbal section and a performance section. The verbal sections involve general knowledge test (oral, general information questions), a similarities test that requires explaining how two different things or concepts are similar, an arithmetic test that uses verbally framed math applications problems without paper, a vocabulary test that requires giving oral definitions of words, a comprehension test that measures social and practical understanding, and a digit span test that requires repeating dictated series of digits forwards and backwards. The performance section involves a picture completion test (identifying missing parts of pictures, coding A test (marking rows of shapes with different lines according to a code as quickly as possible), coding B test (transcribing a digit-symbol code as quickly as possible), a picture arrangement test (sequencing cartoon pictures to make sensible stories), a block design test (copying small geometric designs with four or nine larger plastic cubes), an object assembly test (puzzles of cut-apart silhouette objects with no outline pieces), symbol search test (deciding if target symbols appear in a row of symbols), and maze tests (no pencil lifting, points off for entering blind alleys). As with the adult version, full scale IQ is based on the tests in the verbal and performance scales.

Some embodiments for measuring cognitive function include, among others, Test of Nonverbal Intelligence and Comprehensive Test of Nonverbal Intelligence. Related tests may be used to assess specific brain areas as they relate to attention, executive function, language, memory and visual-spatial and visual-motor skills. Non-limiting examples of these types of tests include NEPSY: A Development Neuropsychological Assessment; Delis-Kaplan Executive Function System (D-KEFS); Comprehensive Test of Phonological Processing (CTOPP); Rey-Osterrieth Complex Figure Test; Children's Memory Scale, Wechsler Memory Scale—Third Edition (WMS-III); Woodcock-Johnson (WJIII) Tests of Cognitive Abilities; Beery-Buktenica Developmental Test of Visual Motor Integration; Wisconsin Card Sorting Test (WCST); Children's Category Test, Judgment of Line Orientation; Behavior Rating Inventory of Executive Function; and Wide Range Assessment of Memory and Learning (WRAML).

Some tests of cognitive function have been developed that are useful extrapolations to animal model systems. Many of these tests are based on operant and non-operant problem solving tasks. General tests include delayed matching sample to sample (short term memory), repeated acquisition (learning), temporal discrimination (timing ability), condition and position response, and progressive ratio (see Slikker et al., Toxicological Sciences 58:222-234 (2000)).

In some embodiments, the test for cognitive function in some animal model systems is a water maze test, generally known as the Morris water maze test, typically used to test learning and memory in small animals such as rats and mice. The Morris water maze consists of a round tank (pool) of water with a submerged hidden escape platform from the water. Extra-maze cues, to test spatial learning, may be placed around the tank at positions visible to the test animal. The ability of the test animal to find the submerged platform provides a measure of the learning and memory function. Malperformance in the Morris water maze test has been associated with impaired LTP.

In some embodiments, the cognitive test is a fear conditioning test, which allows for the assessment of learning and memory of aversive events. Fear conditioning typically relies on the ability of normal animals to learn to fear a previously neutral stimulus because of its temporal association with an aversive stimulus, such as an electric shock, noxious odor, or a startling noise. Typically, the test animal is placed in a conditioning chamber (context) before the onset of a discrete stimulus (the conditioned stimulus or CS), such as a discrete tone. The tone is followed by the aversive stimulus, such as an electrical shock to the foot. The task allows for the simultaneous assessment of learning about simple, unimodal cues and learning about complex, multimodal stimuli such as context. A related test is the startle test, which is used to measure a number of behaviors, including basic startle, pre-pulse inhibition, and fear potentiation of the startle response.

Another type of cognitive test for experimental systems is the Radial Arm Maze. An exemplary maze of this type has a number of arms (e.g., 8) that extend outward from a circular central arena. One or more of the arms is baited to contain a reward and the animal tested for their ability to consume the bait as a function of time. This cognitive test is used to measure spatial learning and memory. Some versions of the task can be used to examine both working and reference memory, such as by measuring the number of reference memory errors (entering an arm that does not contain the reward) and working memory errors (entering an arm containing the reward but previously entered). Like the water maze, this task is sensitive to hippocampal function.

In some embodiments, the cognitive test is a social recognition test that is used to measure social learning and memory. Animals are tested for their ability to remember conspecifics over various time intervals. This may test a variety of cognitive tasks, such as the ability to learn about the safety of food from its conspecifics by sampling those food odors on the breath of littermates. This test may also provide information on aggression and social interaction with non-littermate conspecifics. Memory components can be assessed by repeated exposures to the different stimulus at various frequencies.

In further embodiments, the cognitive test may be an open field test, which evaluates the subject for hyperactivity, exploratory activity, and stereotyped rotation in a test chamber. Additional behavior in this type of test includes, among others, time taken to move to the edges of the open field apparatus, total activity in the open field, and percentage of time spent in the periphery. Versions of the task are used to assess anxiety and memory for context.

In some embodiments, the cognitive test is the SHIRPA Primary Screen, as described in Rogers, D. C. et al., Mamm. Genome 8:711-713 (1997)). This test examines the behavioral and functional profile of the animal by an initial evaluation of the undisturbed behavior in a testing chamber and then under a series of manipulations to elicit a behavioral response from the animal. In the test, observations are made of gait or posture, motor control and co-ordination, changes in excitability and aggression, salivation, lacrimation, piloerection, defecation and muscle tone. In addition to these scored behaviors, the animal is evaluated for other types of stereotyped behavior including, convulsions, compulsive licking, self-destructive biting, retropulsion and indications of spatial disorientation. Initial observations are followed by a sequence of manipulations using tail suspension and the grid across the width of the arena. To complete the assessment, the animal is restrained in a supine position to record autonomic behaviors prior to measurement of the righting reflex. Throughout this procedure vocalization, urination and general fear, irritability or aggression are recorded.

Where a biochemical or molecular defect, such as a genetic abnormality is suspected, the cognitive tests may be used in conjunction with tests used to determined existence of the biochemical or genetic abnormality. Tests include analysis for gross chromosomal abnormalities (e.g., metaphase chromosome), and techniques for determining specific genetic defects, which include as non-limiting examples, polymerase chain reaction, nucleic acid sequencing, nucleic acid hybridization, restriction fragment length analysis (for RFLP), single stranded conformational polymorphism, and fluorescence in situ hybridization (FISH). For example, defects in NF-1 gene may be based on RFLP (Jorde, L. B. et al., Am J Hum Genet. 53(5):1038-50 (1993)); polymerase chain reaction (Abernathy, C. et al., Clin Genet. 45(6):313 (1994)); and single stranded conformational polymorphism (Gomez, L., Cancer Genet Cytogenet. 81(2):173-4 (1995)). Corresponding physiological (facial and limb features) and developmental characteristics may also be assessed to supplement the diagnosis.

In some embodiments, the test for the cognitive defect is an in vitro test that measures molecular correlates of the processes thought to be involved in cognitive function. In some embodiments, the test is an electrophysiology test for LTP (see, e.g., Bliss and Collingridge, Nature 361: 31-39 (1993)). In its basic format, slices of the hippocampus containing the CA1 region, or other suitable neural systems, are removed and a train of stimuli used to evoke action potentials in presynaptic neurons. With certain types of presynaptic stimulation, enhancement of the excitatory postsynaptic potentials (EPSPs) is observed that can last for day or weeks. Induction of LTP is dependent on $Ca^{2+}$ entry into the postsynaptic neuron triggered by N-methyl-D-aspartate receptor activation (see, e.g., Tsien, R. et al. Cell 87:1327-1338 (1996)). As discussed above, LTP may be generated in hippocampal cultures by stimulation of a single input pathway (i.e., homosynaptic) by a train of evoked potentials. Early phase or E-LTP may be induced by a single high-frequency tetanic stimuli while late phase or L-LTP is typically induced by multiples of such tetanic trains (see, e.g., Thomas, M. J. et al., J Neurosci. 18:7118-7126 (1998)). L-LTP may also be induced by paired stimulation of multiple input pathways (i.e., heterosynaptic), where activation of one afferent pathway is paired to a conditioning stimulus in another afferent pathway in the neural network (Huang, Y. Y. et al., Proc. Natl. Acad. Sci. USA 101(3):861-864 (2004)).

To determine whether the LTP is the early phase or the longer lasting phase, various pharmacological agents may be added to the cultures. These include as non-limiting examples, transcription inhibitors, protein synthesis inhibitors, and inhibitors of enzymes thought to be critical for establishment of LTP. Transcription inhibitors include, among others, alpha amanitin, actinomycin D, cordycepin, and 5,6-dichloro-1-D-ribofuranosylbenzimidazole. Protein synthesis inhibitors useful in these in vitro tests include anisomycin, cycloheximide, emetine, rapamycin (Cammalleri, M. et al., Proc Natl Acad Sci USA 100(24):14368-73 (2003)), and puromycin. Enzyme inhibitors may include enzymes involved in formation of LTP, including protein kinase A inhibitors (e.g., KT5720), protein kinase C inhibitors (e.g., chelerythrine); tyrosine kinase inhibitors (e.g., genistein); calmodulin kinase (CaMK) inhibitors (e.g., autocamtide-2-related inhibitory peptide (AIP). These compounds may be used in combination with the HMG CoA reductase inhibitors (or other modulators of the isoprenoid pathway) to determine the effect of inhibitors on LTP.

The following examples are intended to illustrate but not to limit the invention.

NS Mutant Mice Show Deficits in Spatial Learning and Memory

Figure 1:
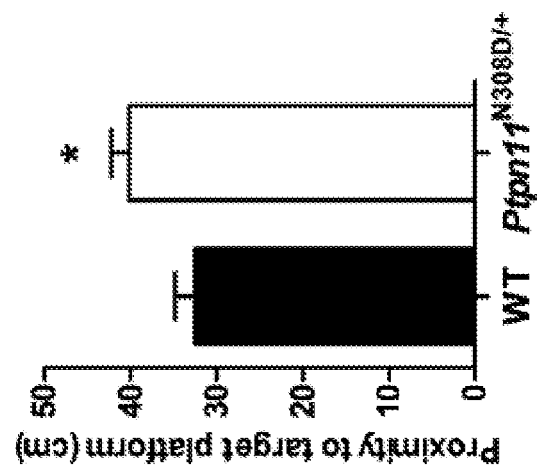
FIG. 1 provides figures showing that mice afflicted with Noonan Syndrome (NS mice) exhibit spatial memory deficits. Panel a) $Ptpn11^{N308D/+}$ (n=9) and wild-type (WT)
Figure 1:
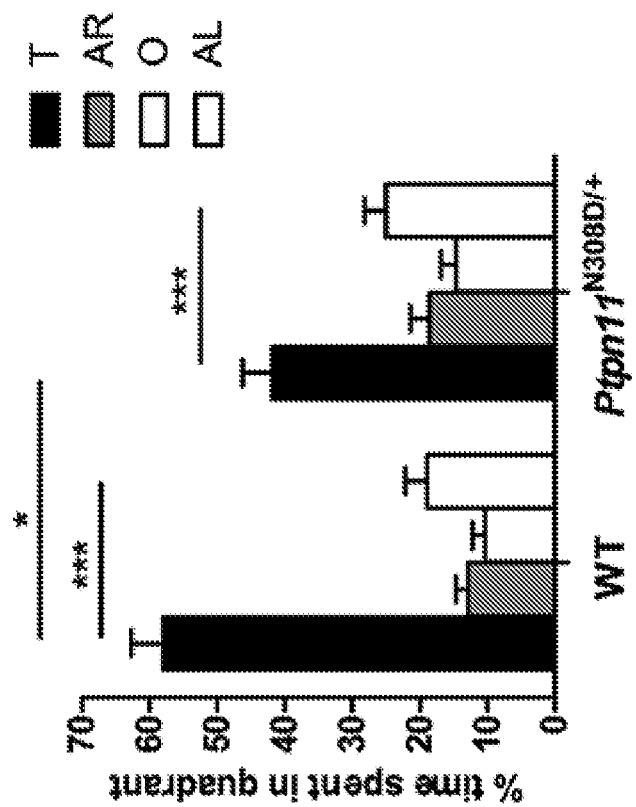
Figure 1:
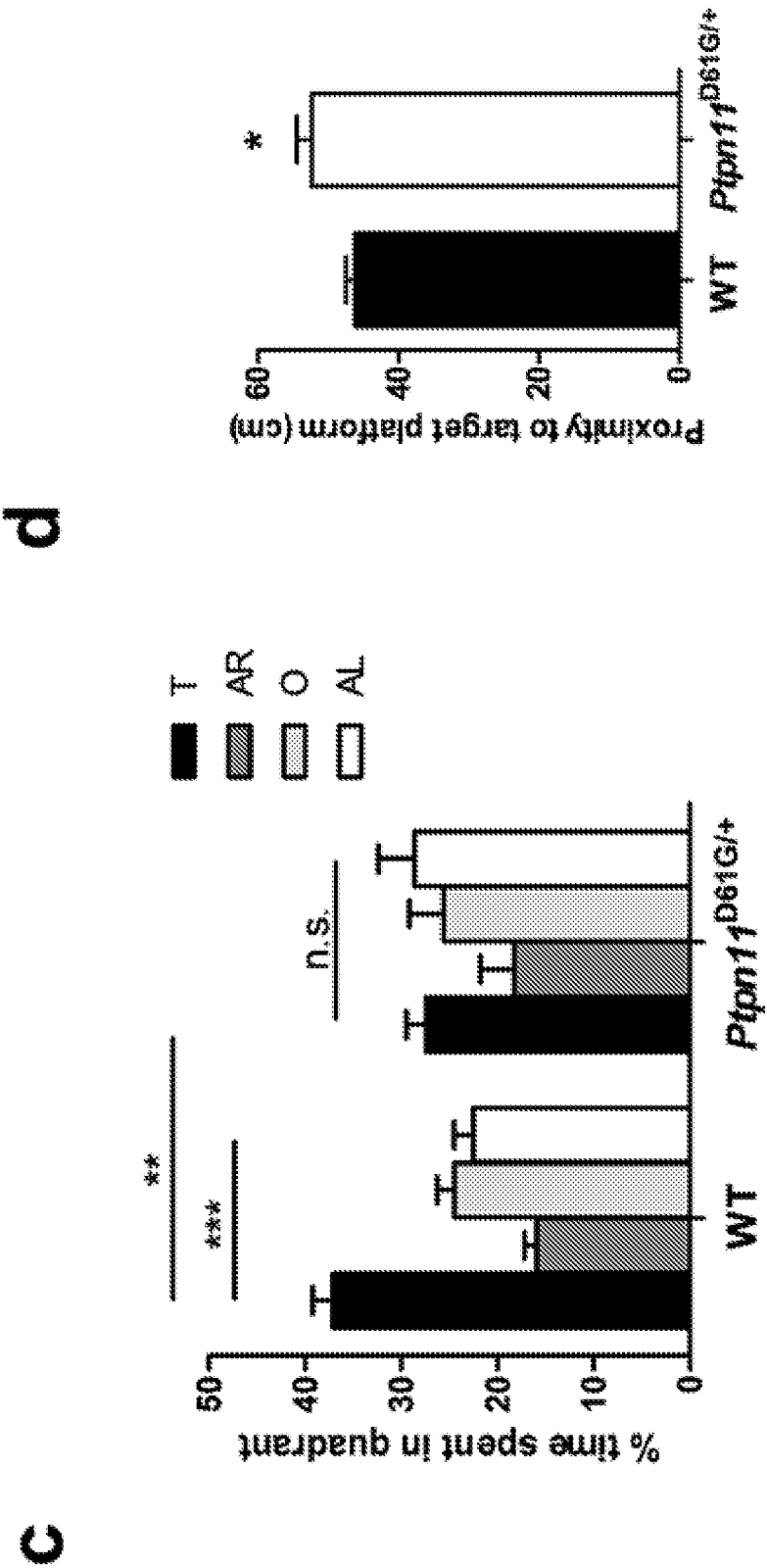

To investigate the underlying mechanism of the learning and memory deficits associated with NS, we studied two lines of heterozygous knock-in mice harboring gain-of-function mutations found in NS patients[14, 16]: $Ptpn11^{D61G/+}$ and $Ptpn11^{N308D/+}$. Previous studies showed that the $Ptpn11^{D61G/+}$ mutation has more severe phenotypes than the $Ptpn11^{N308D/+}$ mutation[14, 16]. As NS patients show deficits in spatial function and in memory tasks depend on hippocampus[4, 8, 9], we tested both Ptpn11 mutants in the hidden platform-version of Morris water maze[17], which allows assessment of both of these functions. In this task, mice learn to use spatial cues around a pool to find an escape platform hidden beneath the water surface. Following training, memory is assessed in probe trials wherein the mice search for 60 seconds with the platform removed from the pool. In probe trials, $Ptpn11^{N308D/+}$ mutants spent significantly less time than wild-type (WT) mice in the target quadrant where the platform was located during training (FIG. 1, panel a). Also, the searches of WT mice during the probe trials were closer to the target platform than those of the mutant (FIG. 1, panel b). Ptpn11$^{N308D/+}$ mutants showed comparable latencies to find the hidden platform to their WT controls during training, performed normally in the visible-platform version of the water maze, and showed normal swimming speeds and total swimming distances in probe trials (FIG. 7). These results suggest that the Ptpn11$^{N308D/+}$ mutation did not impair either visuo-motor function or motivation. After extended training, the Ptpn11$^{N308D/+}$ mutants reached a level of performance comparable to WT mice in probe trials, demonstrating that they can acquire spatial information, albeit at a slower rate than WT mice (FIG. 8). In addition, Ptpn11$^{N308D/+}$ mutants also showed deficits in contextual fear conditioning, another hippocampus-dependent task (FIG. 9).

In agreement with the greater severity of phenotypes in Ptpn11$^{D61G/+}$ mice[14, 16], Ptpn11$^{D61G/+}$ mice also had a more severe behavioral phenotype than Ptpn11$^{N308D/+}$ mice. In probe trials, Ptpn11$^{D61G/+}$ mice did not search selectively in the target quadrant and spent more time searching further from the former platform location than did WT littermates (FIG. 1, panels c, d). Even with additional training, Ptpn11$^{D61G/+}$ mice were unable to reach WT performance levels (FIG. 8). Furthermore, Ptpn11$^{D61G/+}$ mice took longer to reach the platform during training for both the hidden and the visible-platform versions of the Morris water maze (FIG. 7). Swimming speed also was slower in Ptpn11$^{D61G/+}$ mice (WT, 19.72±0.46 cm/s, n=15; Ptpn11$^{D61G/+}$, 11.98±1.27 cm/s, n=10; t-test, P<0.0001), which might have contributed to their longer latencies to reach the platform. Additional behavioral characterization in an open field test revealed that Ptpn11$^{D61G/+}$ mice were hypoactive (FIG. 7). These data demonstrate that the behavioral deficits of Ptpn11$^{D61G/+}$ mice go beyond spatial learning and memory abnormalities. Importantly, the phenotype of NS patients also is not limited to cognitive deficits and can include other neurologic abnormalities, such as a higher rates of motor delay, clumsiness and poor coordination[2].

NS Mutant Mice Show Deficits in Synaptic Plasticity

Hippocampal long-term potentiation (LTP) in the Schaffer collateral synapses of CA1 cells has a key role in spatial learning and memory[18]. To identify the mechanism responsible for the learning and memory deficits caused by the Ptpn11 mutations, we examined CA1 Schaffer collateral LTP in Ptpn11$^{N308D/+}$ and Ptpn11$^{D61G/+}$ mice by performing extracellular field recordings in acute hippocampal slices. Ptpn11$^{N308D/+}$ and WT slices showed no significant differences in basal synaptic transmission or paired-pulse facilitation (FIG. 10). However, LTP induced with theta-burst stimulation (TBS; 2 or 5 theta bursts) was significantly reduced in Ptpn11$^{N308D/+}$ mice (FIG. 2a and FIG. 11). If LTP deficits account for the learning impairment in Ptpn11 mutant mice, then LTP impairment in Ptpn11$^{D61G/+}$ mice should be more severe compared with Ptpn11$^{N308D/+}$ mice. Indeed, Ptpn11$^{D61G/+}$ mice showed more severe LTP deficits than those in Ptpn11$^{N308D/+}$ mice (FIG. 2, panel b). As in Ptpn11$^{N308D/+}$ mice, basal synaptic transmission and paired-pulse facilitation were normal in Ptpn11$^{D61G/+}$ mutants (FIG. 10).

Adult Expression of PTPN11$^{D61G}$ Increases Erk Activation and Impairs Synaptic Plasticity and Learning and Memory The mutations in Ptpn11 mice are present throughout development, affect the entire body and could disrupt the function of brain structures other than the hippocampus. Similarly, NS is a systemic developmental disorder, and it has been assumed that developmental defects are responsible for the cognitive deficits in these patients[19]. Viral vectors provide spatial and temporal regulation of gene expression critical for testing the specific role of Ptpn11 mutation in adult brain. Moreover, NS alleles compromise viability of mice[14], thus making it very difficult to obtain sufficient number of mutant mice for all studies envisioned (Supplementary table 1).

SUPPLEMENTARY TABLE 1

Progeny from NS mutant breeding

|  | WT | Heterozygote | Litter size (Average ± SEM) |
|---|---|---|---|
| Ptpn11$^{D61G/+}$ × WT | 158 | 71 | 4.3 ± 0.2 |
| Ptpn11$^{N308D/+}$ × WT | 501 | 181 | 5.7 ± 0.2 |

To test whether altered Shp2 signaling in the adult hippocampus can cause LTP and, consequently, learning deficits, we overexpressed mutant PTPN11$^{D61G}$ using recombinant adeno-associated virus (AAV-PTPN11$^{D61G}$) in the CA fields (CA1 CA2 and CA3) of the hippocampus of adult wild-type mice. PTPN11$^{D61G}$ overexpression in the hippocampus (FIG. 3, panel a, and FIG. 12) resulted in increased Erk activation as assessed by immunoblotting p-Erk, confirming that AAV is functional (FIG. 3, panel b). Although AAV-PTPN11$^{D61G}$ expression did not affect swimming speed or other performance variables during the acquisition phase of the water maze (FIG. 13), it impaired learning and memory performance in probe trials (FIG. 3, panels c, d). AAV-PTPN11$^{D61G}$-expressing mice spent significantly less time in the target quadrant than did WT controls (GFP/vehicle-injected) and showed significantly longer average proximity to the target platform location (FIG. 3, panels c, d). These data show that expressing SHP2$^{D61G}$ in the adult CA fields of the hippocampus is sufficient to disrupt memory, and demonstrate that SHP2 plays a critical role in adult brain function, in addition to its effect on development[19]. Notably, overexpressing wild-type PTPN11 did not affect basal p-Erk levels or spatial learning and memory (FIG. 14), demonstrating that the adverse impact on learning and memory is specific to the NS-related PTPN11 mutation.

To test whether reducing Erk activity could reverse the memory deficit in AAV-PTPN11$^{D61G}$-expressing mice, we treated these mice with the MEK inhibitor SL327 or vehicle daily, 30 min before training. SL327 treatment (32 mg/kg, intraperitoneal injection) decreased Erk activation in the hippocampus of control and AAV-PTPN11$^{D61G}$ mice (FIG. 15); SL327 also rescued the spatial learning deficits of the AAV-PTPN11$^{D61G}$ mice without affecting the performance of the AAV-GFP group (FIG. 3, panels c, d). These results demonstrate that increased Ras-Erk signaling in adult CA fields of the hippocampus contribute to the memory deficits in AAV-PTPN11$^{D61G}$-expressing mice.

Next, we asked whether AAV-PTPN11$^{D61G}$ expression in adults also impairs CA1 Schaffer collateral LTP. As in Ptpn11$^{D61G/+}$ mutant mice, hippocampal slices from AAV-PTPN11$^{D61G}$-infected mice showed significantly reduced LTP in response to a TBS tetanus (FIG. 3, panels e, f), demonstrating that manipulating Shp2 signaling specifically in the adult CA fields of the hippocampus is sufficient to impair LTP. In addition, TBS failed to further activate Erk in AAV-PTPN11$^{D61G}$-infected hippocampi (FIG. 3b). SL327 treatment also normalized CA1 LTP in hippocampal slices from the AAV-PTPN11$^{D61G}$-infected mice (FIG. 3, panels e, f). By contrast, basal synaptic transmission and paired-pulse facilitation were not affected either by AAV-PTPN11$^{D61G}$ expression or SL327 treatment (FIG. 13). Taken together, these results indicate that deregulated Erk activity causes CA1 LTP deficits, and these deficits are responsible for the spatial learning and memory impairments in mouse models of NS.

PTPN11$^{D61G}$ Overexpression Increases Excitatory Synaptic Function

We examined the electrophysiological mechanism underlying the LTP impairment in AAV-PTPN11$^{D61G}$-infected mice. Increases in Ras signaling are known to facilitate AMPA receptor trafficking to the surface membrane[20]. For example, expression of constitutively active Ras enhances AMPA receptor-mediated currents in hippocampal neurons and impairs LTP[20]. Hence, we asked whether the increases in activated Erk associated with PTPN11$^{D61G}$ expression affected AMPA currents. Whole-cell voltage clamp recordings revealed that the ratio of AMPA:NMDA currents was increased in AAV-PTPN11$^{D61G}$-infected hippocampi (FIG. 4, panels a, b). Moreover, SL327 treatment normalized the AMPA:NMDA ratio (FIG. 4, panels a, b). Whereas the paired-pulse facilitation (PPF) ratio, which is attributed to alternations in presynaptic function, was not affected (FIG. 4, panel c), we observed an increase in mEPSC frequency, but not amplitude in AAV-PTPN11$^{D61G}$-infected mice (FIG. 4, panel d). The increased excitation in PTPN11$^{D61G}$-infected mice was reversed by SL327 treatment (FIG. 4, panel d). We also examined whether Ptpn11$^{D61G/+}$ mutants show the same changes in the excitatory synaptic function. Consistently, mEPSC frequency, but not amplitude was significantly increased in pyramidal neurons of Ptpn11$^{D61G/+}$ mice compared with WT (FIG. 4, panel e). Moreover, mIPSC frequency and amplitude were unaffected in both PTPN11$^{D61G}$-infected mice and Ptpn11$^{D61G/+}$ mutants (FIG. 16). Importantly, the increased excitation in Ptpn11$^{D61G/+}$ mice was reversed by SL327 treatment, indicating that increased Ras-Erk signaling is responsible for the enhanced excitatory synaptic function associated with the Ptpn11$^{D61G}$ mutation (FIG. 4, panel e).

To test the hypothesis that the increased Erk activity, caused by the PTPN11$^{D61G}$ mutation, affected AMPA receptor trafficking, we transfected PTPN11$^{D61G}$ into cultured hippocampal neurons (21 days in vitro, DIV) and labeled the surface GluA1 AMPA receptor (FIG. 5, panels a, b). The number of surface GluA1 receptor clusters was significantly increased in PTPN11$^{D61G}$-infected neurons compared with GFP-infected neurons (FIG. 5, panel c). The size of GluA1 clusters was not affected by the PTPN11$^{D61G}$ expression (FIG. 5, panel d). These results indicate that post-synaptic changes in the AMAP receptor trafficking contribute to the increase in excitatory synaptic function caused by the PTPN11$^{D61G}$ mutation.

Lovastatin Treatment Rescued LTP and Learning Deficits in Ptpn11$^{D61G/+}$ Mice Previous studies showed that lovastatin, a blood-brain-barrier-permeable member of a widely used class of FDA-approved drugs (statins), decreases the levels of isoprenyl groups required for Ras membrane localization and biological activity[21, 22]. As in AAV-PTPN11$^{D61G}$-infected mice, p-Erk levels were increased in Ptpn11$^{D61G/+}$ hippocampi (FIG. 6, panel a). Lovastatin treatment normalized p-Erk levels in mutant hippocampi at concentrations that did not affect Erk activation in controls (FIG. 6, panel a). Importantly, lovastatin-treated Ptpn11$^{D61G/+}$ mice showed better performance (e.g., faster times to reach the hidden platform of the Morris maze) than vehicle-treated Ptpn11$^{D61G/+}$ mice (FIG. 6, panel b) although their swimming speeds were unchanged by the treatment (FIG. 6, panel c). These data suggest that the learning deficits in these animals are not due to their slower swimming speeds or other performance deficits. In probe trials, lovastatin-treated Ptpn11$^{D61G/+}$ mice, unlike vehicle-treated Ptpn11$^{D61G/+}$ mice, showed selective searching in the target quadrant. Also, during probe trials lovastatin-treated Ptpn11$^{D61G/+}$ mice also showed lower average proximity to the platform site (i.e., better performance) than vehicle-treated mutant mice, indicating that lovastatin treatment dramatically improved the performance of Ptpn11$^{D61G/+}$ mice in probe trials (FIG. 6, panels d, e). Importantly, the spatial learning performance of lovastatin-treated Ptpn11$^{D61G/+}$ mice was indistinguishable from controls (FIG. 6, panels d, e). Notably, at the concentration used, lovastatin had no effect on any measure of learning in WT animals (FIG. 6, panels d, e).

Consistent with the hypothesis that increased Ras-Erk activity leads to the LTP deficits responsible for spatial learning impairment in Ptpn11 mutant mice, the levels of 5 TBS-induced LTP in lovastatin-treated Ptpn11$^{D61G/+}$ mice were significantly higher than those in the vehicle-treated mutants and indistinguishable from those in WT control animals (FIG. 6, panels f, g). By contrast, lovastatin treatment had no effect on LTP in hippocampal slices from WT mice (FIG. 6, panels f, g). Thus, lovastatin treatment can normalize LTP deficits and spatial learning impairments even in adult Ptpn11$^{D61G/+}$ mice.

Discussion

Our study provides compelling evidence that the spatial learning and memory deficits in mouse models of NS are caused by enhanced Ras-Erk activation, which disrupts the balance between excitation and inhibition (E/I) and impairs hippocampal synaptic plasticity. Furthermore, our experiments with viral vectors demonstrate that Ptpn11 plays critical roles not only in regulating development[19, 23] but also in adult brain functions. Consistent with our findings, expression of the fly ortholog of SHP2 (Csw) bearing gain-of-function mutations impaired long-term memory in *Drosophila*[24].

It has been known that the activation of Ras-Erk signaling facilitates AMPA receptor trafficking during LTP[20] and that abnormal hyperactivation of postsynaptic Erk signaling impairs hippocampal LTP and learning[25, 26]. Accordingly, our data show that the NS-associated PTPN11$^{D61G}$ increases basal p-Erk levels, excitatory synaptic function, and subsequently impairs LTP. Interestingly, we found that PTPN11$^{D61G}$ expression increases mEPSC frequency, but has no effect on mEPSC amplitude. Changes in mEPSC frequency are commonly attributed to alterations in presynaptic function and are accompanied by changes in PPF ratio. However, PTPN11$^{D61G}$ expression did not affect PPF ratio. Moreover, PTPN11$^{D61G}$ expression increased the number of surface GluA1 clusters in cultured hippocampal neurons, suggesting that the enhancement in excitatory synaptic function caused by PTPN11$^{D61G}$ expression are mainly due to postsynaptic mechanisms. Similarly, deletion of another Ras-Erk regulator SynGAP has been reported to facilitate AMPAR trafficking, increase mEPSC frequency and impair LTP[25, 26].

Deregulation of Ras-Erk signaling has been associated with many genetic disorders such as neurofibromatosis type I (NF1), Costello syndrome, LEOPARD syndrome, CFC syndrome, and Legius syndrome[10, 27]. Among these, studies with the Nf1$^{+/-}$ mutant mouse, which is a model of NF1, demonstrated that increased Ras signaling results in increased GABA release (excitation is normal in these mice) that leads to deficits in LTP and, consequently, learning and memory impairments[28-31]. Altogether these findings demonstrate that similar behavioral (e.g., spatial learning deficits) and even electrophysiological phenotypes (LTP deficits) can be caused by different cellular mechanisms: increases in AMPAR in NS mice and increases in GABA release in NF1 mice. Homozygous deletion of the NF1 gene in mouse post-natal excitatory neurons does not affect either synaptic transmission or learning[30], whereas expression of the NS-mutation PTPN11$^{D61G}$ in post-natal excitatory neurons does disrupt both synaptic transmission and learning, a direct demonstration of the distinct roles of these two Ras signaling modulators.

In this study, we show that postnatal treatment with an FDA-approved drug, lovastatin, can reverse learning and memory as well as LTP deficits in an adult NS mouse model. A previous study showed that lovastatin treatment can rescue spatial learning problems, attention deficits and pre-pulse inhibition deficits in Nf1$^{+/-}$ mutant mice[21]. Thus, our studies suggest that this FDA-approved drug with a strong safety profile may also be useful for treatment of cognitive deficits associated with NS.

Methods

Mice

Ptpn11$^{D61G/+}$ mice were backcrossed to 12956/SvEv and Ptpn11$^{N308D/+}$ mice were backcrossed to C57Bl/6J mice at least 6 times before experiments. Three to six month-old mice were used. For AAV experiments, 3-4 month-old male C57Bl/6J mice (Jackson Laboratory) were used. All experiments used littermates as controls and were done with the experimenters blinded to genotype and treatment. All studies were approved by the Animal Research Committee at UCLA.

Drugs

SL327 (Tocris) was dissolved in DMSO (16 mg/ml) and was injected intraperitoneally once daily, 30 min before the water maze experiment at a dose of 32 mg/kg. The volume of a single injection was under 80 µl. Lovastatin (Mevinolin, Sigma) was prepared as previously described[21]. Briefly, lovastatin was dissolved in ethanol (final concentration of 8%) and 1N NaOH was added to convert mevinolin to the sodium salt. The pH of the final solution (4 mg/ml) was adjusted to 7.5 with HCl. The Vehicle solution was prepared with the same procedure. Lovastatin was administered daily (subcutaneous injection, 10 mg/kg) for 3 days before the first training day of the water maze and 6 hr before training every day thereafter.

AAV

The coding sequence of human PTPN11 with or without the D61G mutation was subcloned into the HindIII-NsiI site of the AAV expression vector pSOFF. The resultant vector expresses mutant PTPN11 under the synthetic CBA promoter (CMV enhancer and chicken beta-actin promoter). Recombinant virus (rAAV5) was purified as previously described[32]. Briefly, an iodixanol gradient purification was performed followed by ion exchange chromatography step which results in a 99% pure vector preparation as judged by silver stained-SDS acrylamide gel fractionation. After the chromatography, the buffer was exchanged and the virus was concentrated in Ringer's solution using a Biomax 100 K concentrator (Millipore). Vector titers were determined by Real Time PCR. Typical titers were 3.09×10$^{12}$ genome copies/ml. rAAV5-GFP expressing only GFP was used as a control. Virus was infused into two sites per hemisphere (1 µl per injection, AP=−2.5, Lat=+/−2, DV=−1.7; AP=−1.8, Lat=+/−1, DV=−1.6) over 5 min through a 30-gauge Hamilton microsyringe. After completion of infusion, the syringe was left in place for an additional 5 min. All the experiments were done three weeks after the infusion.

Behavior

In the hidden platform-version of Morris water maze, mice were trained with two blocks of 2 trials (ITI=1 min) spaced about 45 min apart. In each training trial, mice were released from a different starting position and then were allowed to search for the escape platform for 60 s. The platform was submerged 1 cm under the surface of the water. Once a mouse found the platform, it was left there for 15 s. If a mouse did not find the platform within 60 s, it was guided to the platform and remained on the platform for 15 s before being removed from the pool. Mice were trained for 5-7 consecutive days. Memory was assessed in probe trials that were given after completion of training as described in the main text. During the probe trial, the platform was removed and the mice were allowed to search for it for 60 s. Data were acquired and analyzed using WaterMaze software (Actimetrics).

Electrophysiology

For extracellular recordings of field excitatory postsynaptic potentials (fEPSP), sagittal slices (400 µm) were prepared with a vibratome (VT1000S, Leica) in ice-cold artificial cerebrospinal fluid (ACSF). Slices were recovered at room temperature for at least 90 min before recording in ACSF saturated with 95% O2 and 5% $CO_2$ contained the following (in mM): 120 NaCl, 3.5 KCl, 2.5 $CaCl_2$, 1.3 $MgSO_4$, 1.25 $NaH_2PO_4$, 20 $NaHCO_3$ and 10 D-glucose. Recording was performed in a submerged chamber perfused with ACSF (32° C.). fEPSPs were recorded with platinum-iridium electrodes placed in the CA1 stratum radiatum. Bipolar platinum stimulating electrodes were placed in Schaffer collaterals. Baseline responses were measured with stimulation (0.017 Hz, 0.1 ms pulse duration) at an intensity (typically 20-30 µA) that evoked a response that was approximately one third of the maximum evoked response. LTP was induced with theta burst stimulation (2 or 5 bursts, each burst consisting of four pulses at 100 Hz with a 200 ms interburst interval). Initial fEPSP slopes were measured and normalized to the average of baseline (Clampfit 10.2).

Whole-cell voltage clamp recordings were done with an Axopatch 200B amplifier (Axon Instrument) as previously described[29, 30]. Coronal slices (350 µm) were prepared in ice-cold slice cutting solution containing the following (in mM), 1402-hydroxy-N,N,N-trimethylethanaminium chloride (Choline Chloride), 3 Na-Pyruvate, 2.5, KCl, 1 $CaCl_2$, 7 $MgSO_4$, 26 $NaHCO_3$, 30 D-glucose, 1 kynurenic acid, 1.3 Na-ascorbate. Patch electrodes (3-6 MΩ when filled) were filled with a solution containing the following (in mM): 140 Cs-methanesulfonate, 7 NaCl, 10 HEPES, 0.2 EGTA, 4 Mg-ATP, 0.3 Na-GTP, 5 QX-314. For mEPSC recordings, voltage clamp recordings were performed at −60 mV in the presence of 100 µM picrotoxin and 1 µM TTX. mIPSCs were measured at +10 mV in the presence of 1 mM kynurenic acid and 1 µM TTX. Only recordings during which series resistance changed less than 20% throughout the experiment were analyzed. mPSCs were analyzed with an in-house analysis software (EVAN)[33]. For AMPA/NMDA currents ratio experiments, recordings were performed in ACSF containing 100 µM picrotoxin. Pyramidal neurons in CA1 were voltage-clamped at −65 mV, and AMPA-mediated EPSCs were evoked by stimulating with a bipolar platinum stimulating electrode at 0.1 Hz. After recording 15 responses, the holding potential was manually changed to +40 mV to record NMDA receptor-mediated EPSCs. The AMPA/NMDA ratio was calculated by dividing the mean value of 15 AMPA-mediated EPSC peak amplitudes by the mean value of 15 NMDA receptor-mediated EPSC amplitudes measured at 50 ms after the onset of stimulation (Clampfit 10.2). Experimenters were blinded to the virus or drug.

Western Blot and Immunohistochemistry

Dissected hippocampi were homogenized in protein lysis buffer (10 mM Tris-Cl pH 6.8, 1.6% SDS) containing protease and phosphatase inhibitor cocktails (Sigma). Supernatants were collected after centrifugation and the protein concentration was determined using a BCA assay kit (Thermo). Equal amounts of proteins (5 µg) were separated by electrophoresis on a 4%-12% SDS-PAGE (Invitrogen), and then transferred to nitrocellulose membranes. After blocking with 5% BSA in TBS-T (Tris-buffer saline containing 0.1% Tween-20) for 1 hr at room temperature, membranes were hybridized with a primary antibody overnight at 4° C. After washing with TBS-T, membranes were incubated with a secondary antibody in 5% non-fat milk/TBS-T for 1 hr at room temperature. Signals were visualized by ECL (Thermo) and exposure time was adjusted for the signals to be in a linear range. After detecting phospho-Erk, the membranes were stripped and re-probed with a total Erk antibody. The total Erk level was used to normalize each sample. The following primary antibodies were used: anti-phospho-Erk (Cell Signaling, 1:6000), anti-total Erk (Cell Signaling, 1:5000) and anti-SHP2 (Santa Cruz, 1:3000).

For immunohistochemistry of SHP2, rAAV5-PTPN11$^{D61G}$- or rAAV5-GFP-injected mice were perfused with ice-cold 4% paraformaldehyde and the brains were removed, followed by post-fixation in 4% paraformaldehyde overnight at 4° C. Coronal brain sections (30 µm thick) were mounted onto slide glasses and were treated with 0.3% $H_2O_2$ in methanol for 30 min to quench endogenous peroxidase activity. After blocking with 5% normal goat serum in TBS-T (0.1% Triton X-100), sections were incubated with anti-SHP2 antibody (1:100; Santa Cruz Biotechnology) for 48 hrs at 4° C. A biotinylated anti-rabbit antibody (1:50, 1 hr at room temperature; Vector laboratories) was used as a secondary, which was followed by avidin-biotin-peroxidase complex (Vector Laboratories) formation for 30 min. Signals were visualized by incubating sections in DAB substrate solution (Vector Laboratories). For fluorescent immunohistochemistry of SHP2 and Gad67, anti-SHP2 antibody (1:100, Santa Cruz Biotechnology) and anti-Gad67 antibody (1:500, Millipore) were used as primary antibodies and anti-rabbit Alexa-568 (1:250) and anti-mouse Alexa-647 (1:250) were used as secondary antibodies. Images were acquired by using a confocal microscope (Olympus).

Sindbis Viral Vector Construction and Immunocytochemistry

The coding sequence of human PTPN11 with or without the D61G mutation was subcloned into Sindbis viral expression vector pSinRep5 (Invitrogen) and GFP was inserted to 3' regions of the coding sequence along with an additional subgenomic promoter for bicistronic expression. Sindbis viruses were produced according to the manufacturer's protocol (Invitrogen) and directly added to the medium of cultured rat hippocampal neurons (DIV21). Twelve hours after infection, immunocytochemistry was performed with or without permeabilization by using anti-GluA1-N (Alomone labs) antibody and Cy3-conjugated anti-rabbit IgG antibody (Jackson ImmunoResearch Lab). Images were acquired by using confocal microscope (Zeiss LSM 710) and analyzed by using ImageJ (ver. 1.42q) in blind experiments.

Statistics

For water maze data, we used ANOVAs to analyze quadrant occupancy (% time spent in quadrant). After initial ANOVA analysis, specificity of searching within a genotype was determined by comparing target quadrant to other quadrants using Dunnett's Multiple Comparison Test. We also used two-way ANOVA to analyze the interaction between genotypes and pool quadrants. In addition, we compared target quadrant occupancy among different groups by using the Student's t-test. Proximity measures between two genotypes also were analyzed by Student's t-test. Effects of drug treatments on different genotypes were analyzed by using two-way ANOVA followed by appropriate post-hoc tests. LTP data were analyzed by using repeated-measures ANOVA on the responses after LTP induction and Student's t-test or Bonferroni test on the average of the last 10 min of recording. All the data are represented as mean±s.e.m.

REFERENCES

1. Tartaglia, M. & Gelb, B. D. Noonan syndrome and related disorders: genetics and pathogenesis. *Annu Rev Genomics Hum Genet* 6, 45-68 (2005).
2. Romano, A. A., et al. Noonan syndrome: clinical features, diagnosis, and management guidelines. *Pediatrics* 126, 746-759 (2010).
3. Lee, D. A., Portnoy, S., Hill, P., Gillberg, C. & Patton, M. A. Psychological profile of children with Noonan syndrome. *Dev Med Child Neurol* 47, 35-38 (2005).
4. van der Burgt, I., et al. Patterns of cognitive functioning in school-aged children with Noonan syndrome associated with variability in phenotypic expression. *J Pediatr* 135, 707-713 (1999).
5. Cesarini, L., et al. Cognitive profile of disorders associated with dysregulation of the RAS/MAPK signaling cascade. *Am J Med Genet A* 149A, 140-146 (2009).
6. Pierpont, E. I., et al. Genotype differences in cognitive functioning in Noonan syndrome. *Genes Brain Behav* 8, 275-282 (2009).
7. Verhoeven, W., Wingbermuhle, E., Egger, J., Van der Burgt, I. & Tuinier, S. Noonan syndrome: psychological and psychiatric aspects. *Am J Med Genet A* 146A, 191-196 (2008).
8. Alfieri, P., et al. Long term memory profile of disorders associated with dysregulation of the RAS-MAPK signaling cascade. *Behav Genet* 41, 423-429 (2011).
9. Pierpont, E. I., Tworog-Dube, E. & Roberts, A. E. Learning and memory in children with Noonan syndrome. *Am J Med Genet A* 161, 2250-2257 (2013).
10. Zenker, M. Clinical manifestations of mutations in RAS and related intracellular signal transduction factors. *Curr Opin Pediatr* 23, 443-451 (2011).
11. Neel, B. G., Gu, H. & Pao, L. The 'Shp'ing news: SH2 domain-containing tyrosine phosphatases in cell signaling. *Trends Biochem Sci* 28, 284-293 (2003).
12. Sweatt, J. D. The neuronal MAP kinase cascade: a biochemical signal integration system subserving synaptic plasticity and memory. *J Neurochem* 76, 1-10 (2001).
13. Fragale, A., Tartaglia, M., Wu, J. & Gelb, B. D. Noonan syndrome-associated SHP2/PTPN11 mutants cause EGF-dependent prolonged GAB1 binding and sustained ERK2/MAPK1 activation. *Hum Mutat* 23, 267-277 (2004).
14. Araki, T., et al. Mouse model of Noonan syndrome reveals cell type- and gene dosage-dependent effects of Ptpn11 mutation. *Nat Med* 10, 849-857 (2004).
15. Keilhack, H., David, F. S., McGregor, M., Cantley, L. C. & Neel, B. G. Diverse biochemical properties of Shp2 mutants. Implications for disease phenotypes. *J Biol Chem* 280, 30984-30993 (2005).

16. Araki, T., et al. Noonan syndrome cardiac defects are caused by PTPN11 acting in endocardium to enhance endocardial-mesenchymal transformation. *Proc Natl Acad Sci USA* 106, 4736-4741 (2009).
17. Morris, R. G., Garrud, P., Rawlins, J. N. & O'Keefe, J. Place navigation impaired in rats with hippocampal lesions. *Nature* 297, 681-683 (1982).
18. Lee, Y. S. & Silva, A. J. The molecular and cellular biology of enhanced cognition. *Nat Rev Neurosci* 10, 126-140 (2009).
19. Gauthier, A. S., et al. Control of CNS cell-fate decisions by SHP-2 and its dysregulation in Noonan syndrome. *Neuron* 54, 245-262 (2007).
20. Zhu, J. J., Qin, Y., Zhao, M., Van Aelst, L. & Malinow, R. Ras and Rap control AMPA receptor trafficking during synaptic plasticity. *Cell* 110, 443-455 (2002).
21. Li, W., et al. The HMG-CoA reductase inhibitor lovastatin reverses the learning and attention deficits in a mouse model of neurofibromatosis type 1. *Curr Biol* 15, 1961-1967 (2005).
22. Sebti, S. M., Tkalcevic, G. T. & Jani, J. P. Lovastatin, a cholesterol biosynthesis inhibitor, inhibits the growth of human H-ras oncogene transformed cells in nude mice. *Cancer Commun* 3, 141-147 (1991).
23. Lee, S. H., et al. Synapses are regulated by the cytoplasmic tyrosine kinase Fer in a pathway mediated by p120catenin, Fer, SHP-2, and beta-catenin. *J Cell Biol* 183, 893-908 (2008).
24. Pagani, M. R., Oishi, K., Gelb, B. D. & Zhong, Y. The phosphatase SHP2 regulates the spacing effect for long-term memory induction. *Cell* 139, 186-198 (2009).
25. Komiyama, N. H., et al. SynGAP regulates ERK/MAPK signaling, synaptic plasticity, and learning in the complex with postsynaptic density 95 and NMDA receptor. *J Neurosci* 22, 9721-9732 (2002).
26. Rumbaugh, G., Adams, J. P., Kim, J. H. & Huganir, R. L. SynGAP regulates synaptic strength and mitogen-activated protein kinases in cultured neurons. *Proc Natl Acad Sci USA* 103, 4344-4351 (2006).
27. Tidyman, W. E. & Rauen, K. A. The RASopathies: developmental syndromes of Ras/MAPK pathway dysregulation. *Curr Opin Genet Dev* 19, 230-236 (2009).
28. Shilyansky, C., Lee, Y. S. & Silva, A. J. Molecular and cellular mechanisms of learning disabilities: a focus on NF1. *Annu Rev Neurosci* 33, 221-243 (2010).
29. Shilyansky, C., et al. Neurofibromin regulates corticostriatal inhibitory networks during working memory performance. *Proc Natl Acad Sci USA* 107, 13141-13146 (2010).
30. Cui, Y., et al. Neurofibromin regulation of ERK signaling modulates GABA release and learning. *Cell* 135, 549-560 (2008).
31. Costa, R. M., et al. Mechanism for the learning deficits in a mouse model of neurofibromatosis type 1. *Nature* 415, 526-530 (2002).
32. Zolotukhin, S., et al. Production and purification of serotype 1, 2, and 5 recombinant adeno-associated viral vectors. *Methods* 28, 158-167 (2002).
33. Hajos, N., Nusser, Z., Rancz, E. A., Freund, T. F. & Mody, I. Cell type- and synapse-specific variability in synaptic GABAA receptor occupancy. *Eur J Neurosci* 12, 810-818 (2000).

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of treating a cognitive deficit in a subject having Noonan syndrome, comprising:
administering an effective amount of one or more hydroxymethylglutaryl CoA (HMG CoA) reductase inhibitors to a subject having the cognitive deficit and Noonan syndrome.

2. The method of claim 1, wherein the one or more HMG CoA inhibitors comprises a statin.

3. The method of claim 2, wherein the statin is selected from the group consisting of atorvastatin, cerivastatin, fluvastatin, lovastatin, pravastatin, pitavastatin, rovustatin, simvastatin, and mixtures thereof.

4. The method according to claim 1, wherein the effective amount does not significantly lower total serum cholesterol level in the subject.

5. The method according to claim 1, which further comprises administering a farnesyl transferase inhibitor, a geranylgeranyl transferase inhibitor, an inhibitor of γ-aminobutyric acid (GABA) mediated inhibition, an inhibitor of GABA receptor activity, and/or a modulator of Ras-ERK signaling.

6. The method according to claim 1, wherein the supplementary compound is administered before, during, and/or after the inhibitor.

7. The method according to claim 1, wherein the administering is by adjunctive administration.

8. The method of claim 7, wherein the adjunctive administration is simultaneous administration.

9. The method of claim 7, wherein the adjunctive administration is sequential administration.

10. The method of claim 1, wherein said subject has a normal cholesterol level.

11. The method of claim 1, which further comprises administering an effective amount of an inhibitor of MEK to the subject.

12. The method of claim 11, wherein the inhibitor of MEK is a specific inhibitor of MEK1 and/or MEK2.

13. The method of claim 11, wherein the inhibitor of MEK is α-(Amino((4-aminophenyl)thio)methylene)-2-(trifluoromethyl)benzeneacetonitrile (SL327).

14. The method of claim 11, wherein the one or more hydroxymethylglutaryl CoA (HMG CoA) reductase inhibitors are administered before, during, and/or after administration of the inhibitor of MEK.

15. A method of improving cognitive function of a subject having a cognitive deficit and Noonan syndrome, comprising:
administering an effective amount of one or more hydroxymethylglutaryl CoA (HMG CoA) reductase inhibitors to a subject having the cognitive deficit and Noonan syndrome.

* * * * *